US012625144B2

(12) United States Patent
Rai et al.

(10) Patent No.: US 12,625,144 B2
(45) Date of Patent: May 12, 2026

(54) CHEMOSELECTIVE SENSITIVITY BOOSTER FOR TAGGING A PEPTIDE, PEPTIDE CONJUGATE, OR SIMILAR REACTIVE MOLECULE

(71) Applicant: INDIAN INSTITUTE OF SCIENCE EDUCATION AND RESEARCH BHOPAL, Bhauri Bhopal (IN)

(72) Inventors: Vishal Rai, Bhauri Bhopal (IN); Rohith Singudas, Bhauri Bhopal (IN); Neelesh Chandrakant Reddy, Bhauri Bhopal (IN)

(73) Assignee: INDIAN INSTITUTE OF SCIENCE EDUCATION AND RESEARCH BHOPAL, Bhauri Bhopal (IN)

( * ) Notice: Subject to any disclaimer, the term of this patent is extended or adjusted under 35 U.S.C. 154(b) by 952 days.

(21) Appl. No.: 17/596,208

(22) PCT Filed: Jun. 4, 2020

(86) PCT No.: PCT/IN2020/050497
§ 371 (c)(1),
(2) Date: Dec. 6, 2021

(87) PCT Pub. No.: WO2020/245843
PCT Pub. Date: Dec. 10, 2020

(65) Prior Publication Data
US 2022/0299521 A1 Sep. 22, 2022

(30) Foreign Application Priority Data
Jun. 5, 2019 (IN) ............................ 201921022294

(51) Int. Cl.

| | |
|---|---|
| ***C07D 207/46*** | (2006.01) |
| ***A61K 47/68*** | (2017.01) |
| ***C07D 213/53*** | (2006.01) |
| ***C07D 213/68*** | (2006.01) |
| ***C07D 213/74*** | (2006.01) |
| ***C07D 213/81*** | (2006.01) |
| ***C07D 235/14*** | (2006.01) |
| ***C07D 401/04*** | (2006.01) |
| ***C07D 401/14*** | (2006.01) |
| ***G01N 33/68*** | (2006.01) |

(52) U.S. Cl.
CPC ...... *G01N 33/6848* (2013.01); *A61K 47/6811* (2017.08); *C07D 213/53* (2013.01); *C07D 213/68* (2013.01); *C07D 213/74* (2013.01); *C07D 213/81* (2013.01); *C07D 235/14* (2013.01); *C07D 401/04* (2013.01); *C07D 401/14* (2013.01); *G01N 2560/00* (2013.01)

(58) Field of Classification Search
CPC .............................. C07D 207/46; C07K 14/00
USPC ........................................................ 548/530
See application file for complete search history.

(56) References Cited

U.S. PATENT DOCUMENTS

2015/0072396 A1 3/2015 Gee et al.

FOREIGN PATENT DOCUMENTS

WO 2012/121973 A1 9/2012

OTHER PUBLICATIONS

Singudas, R. et al.: Sensitivity booster for mass detection enables unambiguous analysis of peptides, proteins, antibodies, and protein conjugates. Chem. Commun., vol. 55, pp. 9979-9982, 2019.*
E. M. Pelegri-O'Day, et al., "Therapeutic Protein-Polymer Conjugates: Advancing Beyond PEGylation", J. Am.Chem. Soc., vol. 136, pp. 14323-14332 (2014).
V. Chudasama et al., "Recent advances in the construction of antibody-drug conjugates", Nature Chemistry, vol. 8, pp. 114-119 (Feb. 2016).
A. J. Keefe et al., "Poly(zwitterionic)protein conjugates offer increased stability without sacrificing binding affinity or bioactivity", Nat. Chem., vol. 4, pp. 59-63 (Jan. 2012).
P. Agarwal et al., "Site-Specific Antibody-Drug Conjugates: The Nexus of Bioorthogonal Chemistry, Protein Engineering, and Drug Development", Bioconjugate Chemistry, vol. 26, pp. 176-192, (2015).
Ning et al., "Protein Modification by Strain-Promoted Alkyne-Nitrone Cycloaddition", Angew. Chem., Int. Ed., vol. 49, pp. 3065-3068 (2010).
S. R. Adusumalli et al., "Single-Site Labeling of Native Proteins Enabled by a Chemoselective and Site-Selective Chemical Technology", J. Am. Chem. Soc., vol. 140, pp. 15114-15123 (2018).
J. M. Antos et al., "Selective Tryptophan Modification with Rhodium Carbenoids in Aqueous Solution", J. Am. Chem. Soc., vol. 126, pp. 10256-10257 (2004).
D. Chen et al., "Selective N-terminal functionalization of native peptides and proteins", Chem. Sci., vol. 8, pp. 2717-2722 (2017).
C. D. Spicer et al., "Selective chemical protein modification", Nature Communications, vol. 5, No. 4740, pp. 1-14 (Sep. 5, 2014).
G. Chen et al., "Reactivity of Functional Groups on the Protein Surface: Development of Epoxide Probes for Protein Labeling", J. Am. Chem. Soc., vol. 125, pp. 8130-8133 (2003).
Y. Takaoka, "One-Pot and Sequential Organic Chemistry on an Enzyme Surface to Tether a Fluorescent Probe at the Proximity of the Active Site with Restoring Enzyme Activity", J. Am. Chem. Soc., vol. 128, pp. 3273-3280 (2006).

(Continued)

*Primary Examiner* — Charanjit Aulakh
(74) *Attorney, Agent, or Firm* — HSML P.C.

(57) ABSTRACT

The invention pertains to chemoselective sensitivity booster for tagging a peptide, peptide conjugate, or similar reactive molecule for analysis of a peptide, protein, antibody, protein bioconjugate, antibody bioconjugate, and similar analytes. The sensitivity booster comprises of sp2 or sp3 nitrogen centers in combination with hydrophobic carbon chains linked with an electrophile or nucleophile for attachment with a peptide, peptide conjugate, or molecules with similar reactivity.

8 Claims, 6 Drawing Sheets

Figure 1:
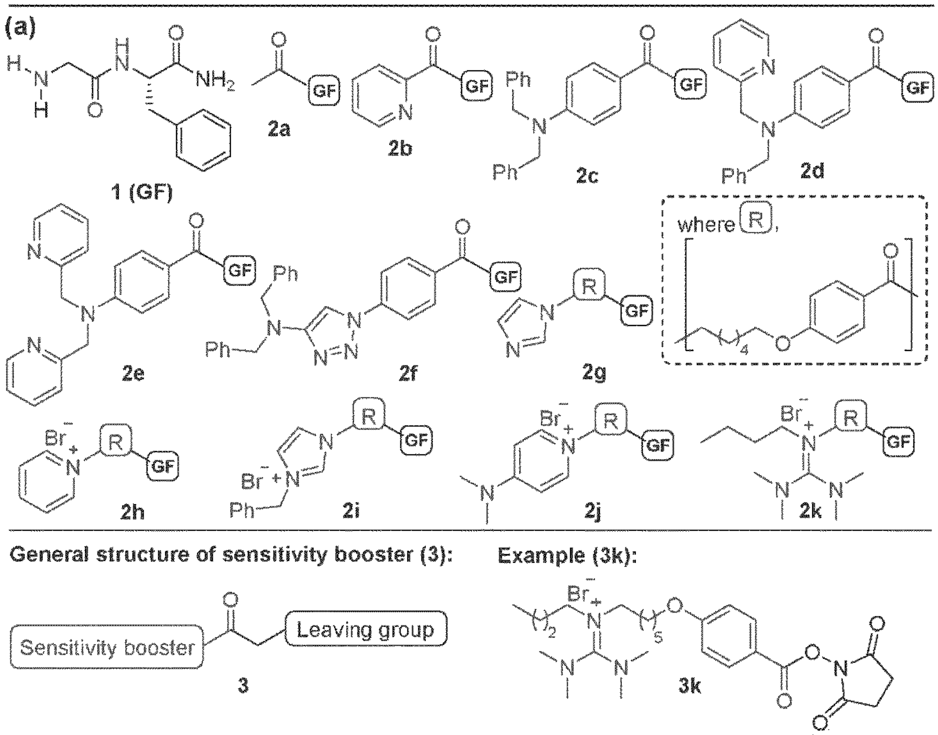
Figure 1:
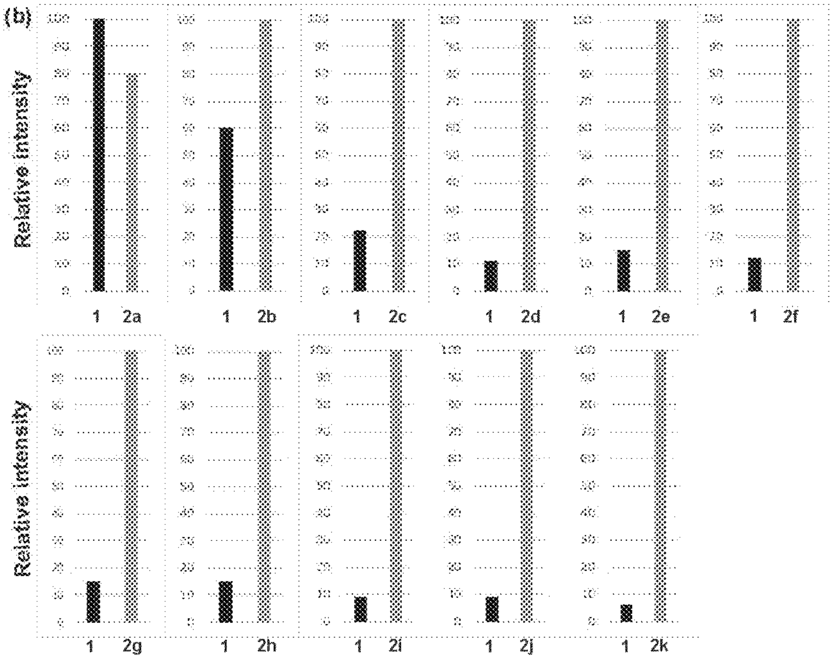

Specification includes a Sequence Listing.

(56) References Cited

OTHER PUBLICATIONS

M. J. Matos et al., "Chemo- and Regioselective Lysine Modification on Native Proteins", J. Am. Chem. Soc., vol. 140, pp. 4004-4017 (2018).
R. Aebersold et al., "Mass spectrometry-based proteomics", Nature, vol. 422, pp. 198-207 (Mar. 13, 2003).
Q. Hu et al., "The Orbitrap: a new mass spectrometer", J. Mass Spectrom., vol. 40, pp. 430-443 (2005).
H. López-Fernández et al., "Mass-Up: an all-in-one open software application for MALDI-TOF mass spectrometry knowledge discovery", BMC Bioinformatics, vol. 16, No. 318, pp. 1-12 (2015).
P. Stefanowicz et al., "Derivatization of peptides for improved detection by mass spectrometryy", Amino Acids, Pept. Proteins, vol. 40, pp. 36-74 (2016).
M. R. Wilkins et al., "Detailed peptide characterization using PEPTIDEMASS—a World-Wide-Web-accessible tool", Electrophoresis, vol. 18, pp. 403-408 (1997).
A. R. Ramya et al., "Synthesis, Crystal Structure, and Photoluminescence of Homodinuclear Lanthanide 4-(Dibenzylamino)benzoate Complexes", Inorg. Chem., vol. 49, No. 5, pp. 2407-2415 (2010).
A. V. Pestov et al., "Complexes of Mono- and Bis(2-carboxyethyl)-2-picolylamine: Synthesis and Crystal and Molecular Structures", Rus. J. Cor. Chem., vol. 36, No. 10, pp. 769-777 (2010).
Y. Liu et al., "An efficient oxygen evolving catalyst based on a u O diiron coordination complex", Chem. Commun., vol. 50, pp. 12779-12782 (2014).
C. K. Sams et al., "Coordination chemistry of transition metal complexes of a novel pentadentate ligand", Inorganica Chimica Acta, vol. 318, pp. 45-52 (2001).
S. Raiguel et al., "Multi-Gram Scale Synthesis of 1,2,3-Triazolium lonic Liquids and Assay of Their Resistance towards Bases", Eur. J. Org. Chem., pp. 4850-4856 (2018).
M. Xu et al., "A Novel Approach to 1-Monosubstituted 1,2,3-Triazoles by a Click Cycloaddition/Decarboxylation Process", Synthesis, No. 2, pp. 223-228 (2011).
L. Purushottam et al., "Chemoselective and site-selective peptide and native protein modification enabled by aldehyde autooxidation", Chem. Commun., vol. 53, pp. 959-962 (2017).
L. Huang et al., "Synthesis, biological evaluation, and molecular modeling of berberine derivatives as potent acetylcholinesterase inhibitors", Bioorg. Med. Chem., vol. 18, pp. 1244-1251 (2010).
Srinivasa Rao Adusumalli et al., "Aldehydes can switch the chemoselectivity of electrophiles in protein labeling", Org. Biomol. Chem., 2018, vol. 16, pp. 9377-9381 (2018).
A. J. Barrett et al., Handbook of Proteolytic Enzymes, 2nd Ed., vol. 1; Academic Press: San Diego, CA, 1998 (1361 pages).
International Search Report and Written Opinion, PCT/IN2020/050497, Oct. 9, 2020 (7 pages).

* cited by examiner (a)

1 (GF), 2a, 2b, 2c, 2d, 2e, 2f, 2g, where R, 2h, 2i, 2j, 2k

General structure of sensitivity booster (3):

Sensitivity booster, Leaving group

3

Example (3k):

3k

CHEMOSELECTIVE SENSITIVITY BOOSTER FOR TAGGING A PEPTIDE, PEPTIDE CONJUGATE, OR SIMILAR REACTIVE MOLECULE

SEQUENCE LISTING

The present application is being filed with a Sequence Listing in electronic format. The Sequence Listing is provided as a file entitled "Sequence Listing_0001.txt" created on Feb. 2, 2026, which is 20,281 bytes in size. The information in the electronic format of the Sequence Listing is incorporated herein by reference in its entirety.

FIELD OF INVENTION

The invention pertains to the field of protein chemistry and specifically to chemoselective sensitivity booster for tagging a peptide, peptide conjugate, or similar reactive molecule for analysis of a peptide, protein, antibody, protein bioconjugate, antibody bioconjugate, and similar analyte.

BACKGROUND OF INVENTION

Protein bioconjugation caters to the diverse requirements of biophysical chemistry, biochemistry, protein-targeted, and protein-based therapeutics. In recent years, the chemical technologies for precise labelling of native proteins has witnessed remarkable growth. However, the unambiguous characterization of protein bioconjugates poses several challenges and has been responsible for slowing the developments.

Mass spectrometry (MS) has become the first choice for analysis of protein bioconjugates due to the superior sensitivity and excellent ability to provide structural information. Here, the first step involves the estimation of their mass to charge ratio (m/z). Subsequently, the protein is digested by a proteolytic enzyme, and the m/z of peptides is recorded for their mapping. The peptide(s) with a label is selected and taken forward for the fragmentation and sequenced by tandem mass spectrometry (MS-MS). The latter allows the identification of the site of labelling in a protein bioconjugate. The sensitivity and accuracy of peptide mapping and its MS plays a defining role in the success of such protein sequencing. In this perspective, there have been efforts to improve the technologies associated with hardware, software, and chemical derivatization. In the attempts of single-site chemical modification, the protein with an additional mass of one label is assumed to be modified at a single residue. Further, the validation comes from the identification of a single peptide with the label. Unfortunately, the MS-MS does not map a considerable part of the peptides due to the partial digestion, limited ionization, or suppression from other ions. Hence, the absence of labelled peptide in a digested protein bioconjugate is common and adds to the analytical challenges. The limitations of the existing knowledge in the art is that, even if we identify a single labelled peptide, the confirmation of homogeneity comes with an assumption that the un-detected peptides are not labelled. Besides, the MS-MS does not map all the ions even for the detected labelled peptide. Hence, it becomes essential to develop tools that can enhance the detection of peptides and its subsequent fragments.

OBJECT OF THE INVENTION

An object of the invention is for a chemo-selective sensitivity booster for tagging a peptide, peptide conjugate, or similar reactive molecule for analysis of a peptide, protein, protein bioconjugate, antibody, and similar analyte, for enhancing the sensitivity of peptide detection up to attomolar concentration by mass spectrometry.

An object of the invention is for a sensitivity booster which comprises of sp2 or sp3 nitrogen centers in combination with hydrophobic carbon chains linked with an electrophile or nucleophile for attachment with a peptide, peptide conjugate, or molecules with similar reactivity.

Another object of the invention is to enhance the primary sequence coverage during the peptide mapping by mass spectrometry.

Another object of the invention is for a method to simplify and enhance the MS-MS fragmentation pattern enabling the unambiguous sequencing of peptides, proteins, antibodies and protein bioconjugates.

DESCRIPTION OF DRAWINGS AND FIGURES

FIG. 1*a* represents a few of the potential sensitivity boosters of the invention conjugated with model peptide Gly-Phe (GF, 1) 2a-2k. 1*b* represents the relative intensity of the dipeptide and the sensitivity boosters of the invention conjugated with model peptide (2a-2k) in ESI-MS.

FIG. 2*a* represents improvement in the detection peptides for tryptic digest of cytochrome C by tagging with the sensitivity booster. FIG. 2*b* represent simplification and improvement in the MS-MS fragmentation pattern for cytochrome C.

Figure 3:
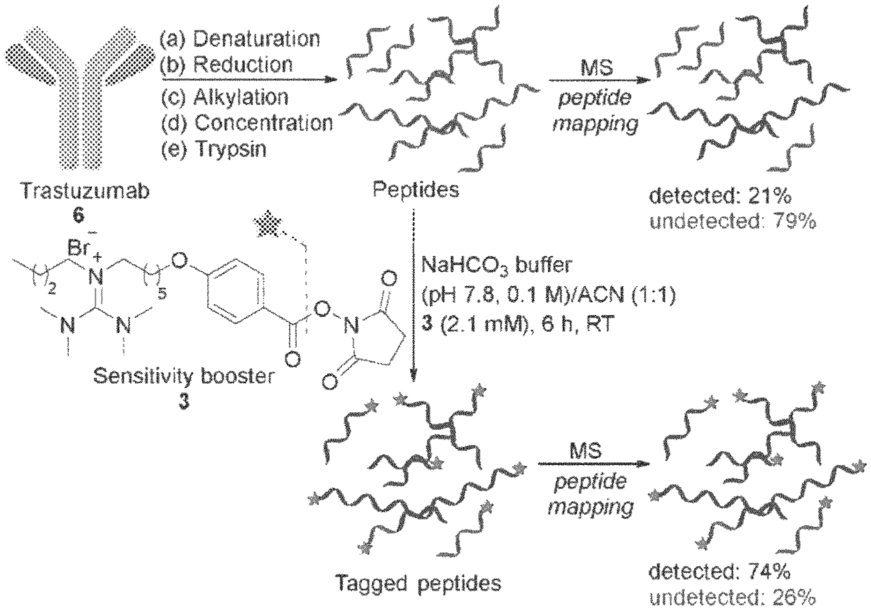

FIG. 3 depicts that the sensitivity booster improves the peptide mapping of trastuzumab, a monoclonal antibody for directed cancer chemotherapeutics.

FIG. 4*a* depicts the tagging with sensitivity booster improves the detection of heterogeneity in the bioconjugation of a protein. FIG. 4*b* depicts selective enhancement of the peptides with the modified sites by sensitivity booster (9).

Figure 5:
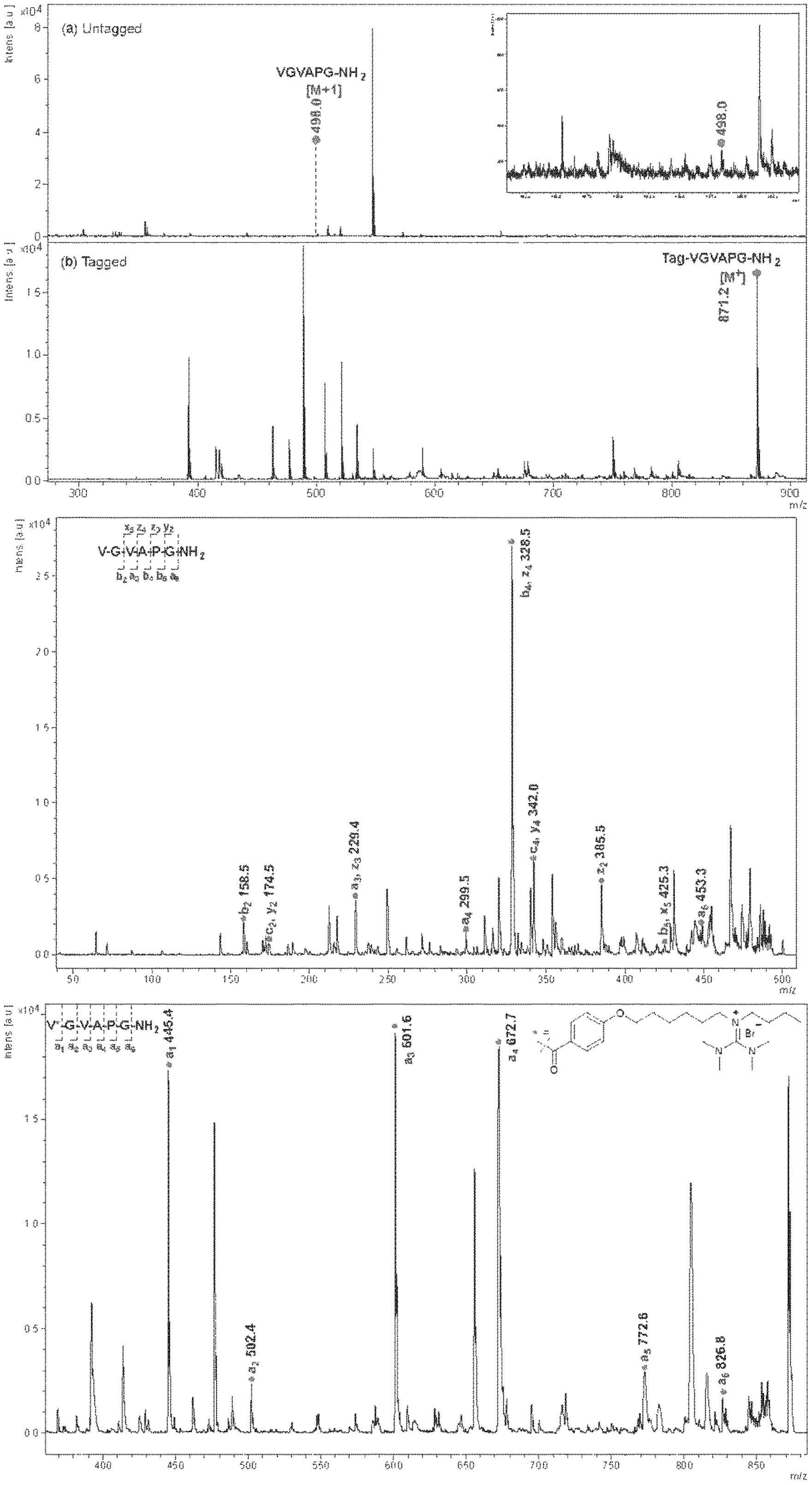

FIG. 5: (a) MS of VGVAPG-$NH_2$(SEQ ID NO: 1), (b) MS of Tag-VGVAPG-$NH_2$ (SEQ ID NO: 1), (c) MS-MS of VGVAPG-$NH_2$ (SEQ ID NO: 1), (d) MS-MS of Tag-VGVAPG-$NH_2$ (SEQ ID NO: 1).

Figure 6:
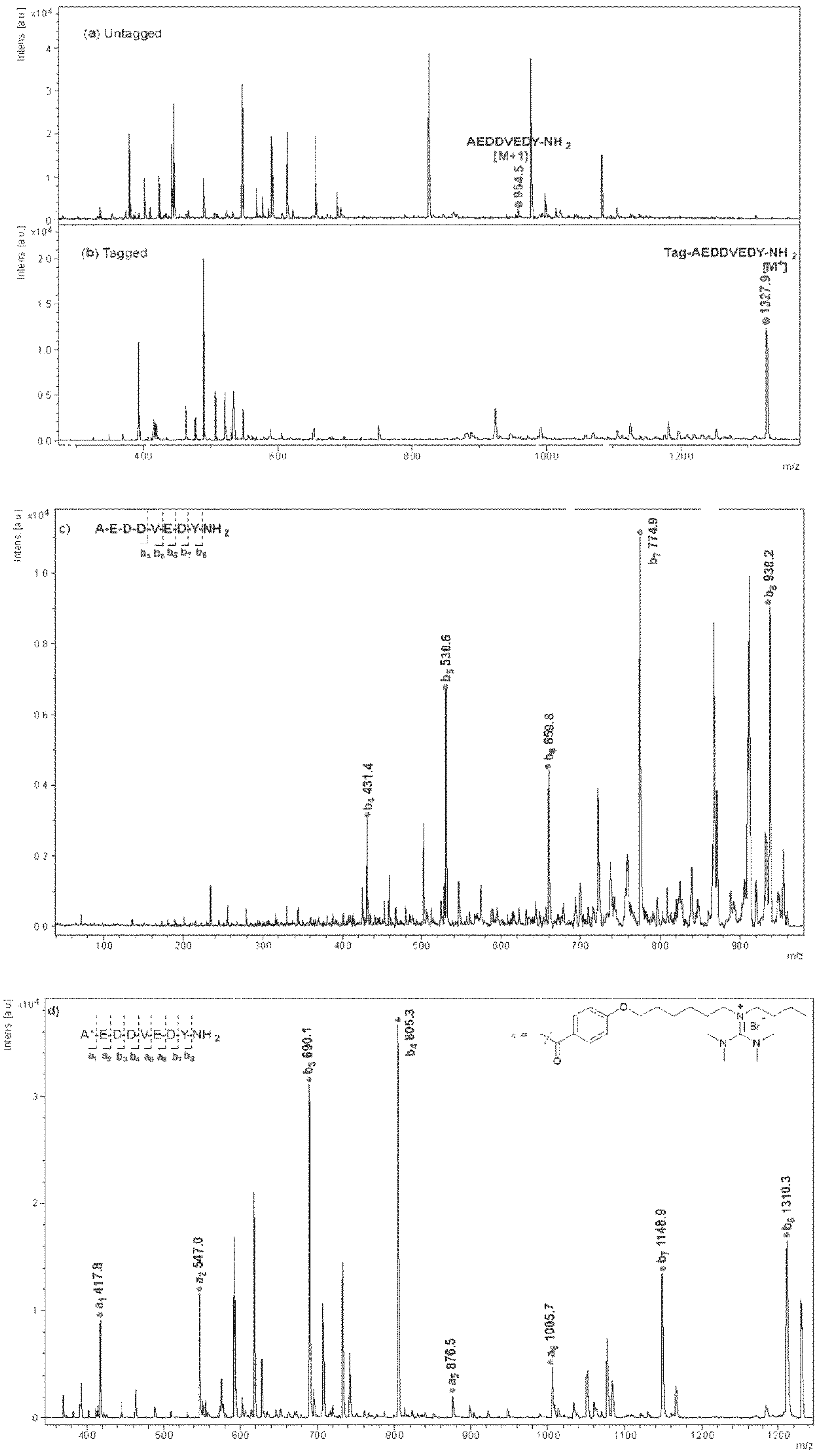

FIG. 6: (a) MS of AEDDVEDY-$NH_2$ (SEQ ID NO: 2), (b) MS of Tag-AEDDVEDY-$NH_2$ (SEQ ID NO: 2), (c) MS-MS of AEDDVEDY-$NH_2$ (SEQ ID NO: 2), (d) MS-MS of Tag-AEDDVEDY-$NH_2$ (SEQ ID NO: 2).

DEFINITIONS

The term conjugation and tagging are interchangeably used and refers to the conjugation of the chemoselective sensitivity booster to the peptides.

The conjugated or tagged peptides refer to the peptides attached with the chemoselective sensitivity booster of the invention.

The electrophile is a functional group that can accept a pair of electrons and the nucleophile is a functional group that can donate a pair of electrons.

The term chemoselective refers to the capability of a reagent to differentiate one functional group from others.

Abbreviations for the reagents used are what is commonly known and abbreviations o specific terms are provided.

DETAILED DESCRIPTION

Accordingly, the invention is for a chemoselective sensitivity booster for tagging a peptide, peptide conjugate, or similar reactive molecule for analysis of a peptide, protein, protein bioconjugate, antibody, and similar analyte, for enhancing the sensitivity of peptide detection up to attomolar concentration by mass spectrometry.

The chemoselective sensitivity booster comprises of sp2 or sp3 nitrogen centers in combination with hydrophobic carbon chains linked with an electrophile or nucleophile for attachment with a peptide, peptide conjugate, or molecules with similar reactivity.

The chemoselective sensitivity booster is selected from pyridine, multiple nitrogen, triazole, diazole, pyridinium ion, the imidazolium ion, 4-(dimethylamino) pyridinium ion and the guanidinium ion.

In an aspect the chemoselective sensitivity booster, is selected from one of

- 2,5-dioxopyrrolidin-1-yl picolinate,
- 2,5-dioxopyrrolidin-1-yl 4-(dibenzylamino)benzoate,
- 2,5-dioxopyrrolidin-1-yl 3-(benzyl(pyridin-2-ylmethyl)amino)propanoate,
- 2,5-dioxopyrrolidin-1-yl 3-(bis(pyridin-2-ylmethyl)amino)propanoate,
- 2,5-dioxopyrrolidin-1-yl 4-(4-((dibenzylamino)methyl)-11H-1,2,3-triazol-1-yl)benzoate,
- 2,5-dioxopyrrolidin-1-yl-4-((6-(1H-imidazol-1-yl)hexyl)oxy)benzoate,
- 1-(6-(4-(((2,5-dioxopyrrolidin-1-yl)oxy)carbonyl)phenoxy)hexyl)pyridin-1-ium bromide,
- 1-benzyl-3-(6-(4-(((2,5-dioxopyrrolidin-1-yl)oxy)carbonyl)phenoxy)hexyl)-1H-imidazol-3-ium bromide,
- 4-(dimethylamino)-1-(6-(4-(((2,5-dioxopyrrolidin-1-yl)oxy)carbonyl)phenoxy) hexyl)pyridin-1-ium bromide,
- N-(bis(dimethylamino)methylene)-N-butyl-6-(4-(((2,5-dioxopyrrolidin-1-yl)oxy)carbonyl)phenoxy)hexan-1-aminium bromide,
- 6-(aminooxy)-N-(bis(dimethylamino)methylene)-N-(6-phenoxyhexyl)hexan-1-aminium bromide.

The structure is as provided in the following

S53

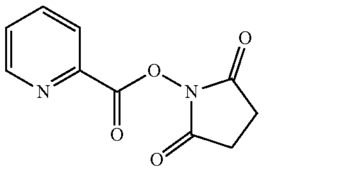

S6

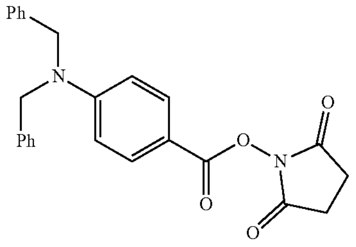

S54

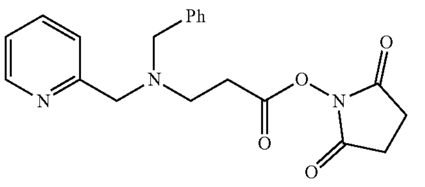

-continued

S55

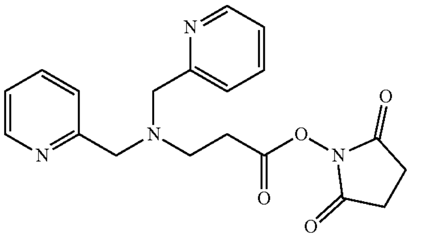

S56

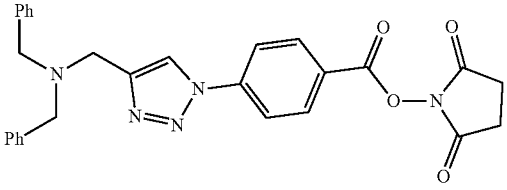

S27

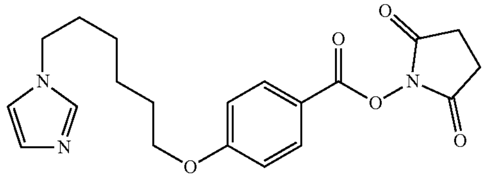

S57

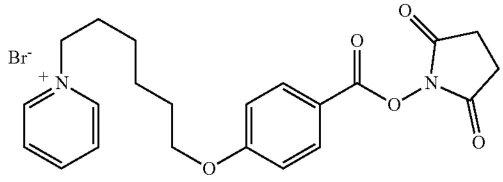

S58

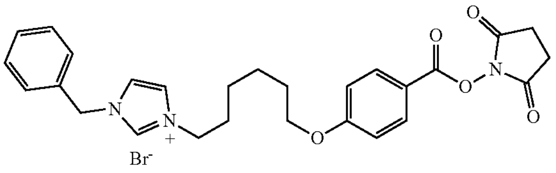

S59

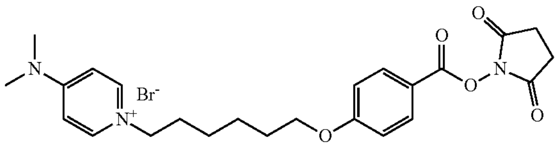

3

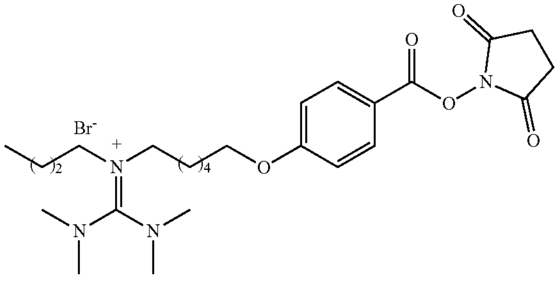

-continued

9

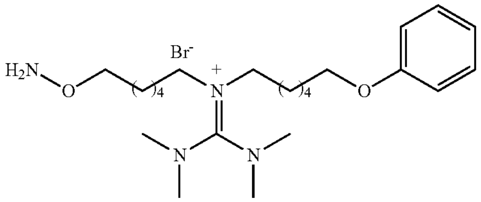

In one embodiment, the invention discloses that tagging of the peptides with the chemoselective sensitivity booster, is at either to a polar or non-polar peptide.

In another embodiment, the conjugation of sensitivity booster enhances the signal of the tagged peptides and has a mass shift of Δm=374 Da with the conjugation of sensitivity booster. It renders a signal well separated from the matrix in mass spectrometry.

In an aspect the sensitivity of tagged peptide detection is up to attomolar concentration in the mass spectrometry (MS).

In an aspect the conjugation of the chemoselective sensitivity booster is at ε-amine of C terminus Lys in a peptide or with the N-terminus α-amine.

In an aspect the sequence coverage of tagged peptides by mass spectrometry is 75-100%.

The conjugation of sensitivity booster is for peptide detection in proteins, antibodies including monoclonal antibody (mAb), and their bioconjugates.

The chemoselective sensitivity booster is for peptide mapping or peptide like reactive molecules and analysis of proteins, antibodies, protein bioconjugates, and antibody bioconjugates by MS-MS spectrum.

In an aspect conjugation of a non-polar hexapeptide, VGVAPG (SEQ ID NO: 1) with the sensitivity booster (3) for 2 h resulted in signal enhancement while suppressing the matrix peaks. It resulted in the mass shift of Δm=374 Da and renders a signal well separated from the matrix. The reaction of sensitivity booster occurs chemoselectively at the N-terminus α-amine and the MS-MS gives a simplified spectrum predominantly reflecting the a, b, c type ions only. A polar octapeptide AEDDVEDY (SEQ ID NO: 2) with the sensitivity booster (3) for 2 h resulted in signal enhancement while suppressing the matrix peaks. It resulted in the mass shift of Δm=374 Da and renders a signal well separated from the matrix. The reaction of sensitivity booster occurs chemoselectively at the N-terminus α-amine and the MS-MS gives a simplified spectrum predominantly reflecting the a, b, c type ions only.

In an aspect conjugation of a tetrapeptide, GFHK (SEQ ID NO: 3), with the sensitivity booster (3), resulted in enhanced detection and simplified MS-MS and resulted in a mono-labeled peptide is formed with chemo selective labeling of C-terminus Lys. MS-MS analysis of the peptide fragmentation shows "y ions" predominantly. The suppression of "b ions" simplifies the sequencing. Further, the chemoselectivity and enhanced sensitivity are the same with a pentapeptide GGPRK (SEQ ID NO: 4).

In an aspect, the conjugation of the chemoselective booster is with peptides of variable length.

The process of tagging the peptides with the chemoselective sensitivity booster includes preferential labelling of s-amine of C terminus Lys in a peptide. The peptide fragmentation by MS-MS shows "x, y, z type ions" predominantly. In the absence of C-terminus Lys, the chemoselective labelling occurs at the N-terminus α-amine and MS-MS shows "a, b, c ions" predominantly.

In another embodiment the invention discloses a process for analysis and identification of bioconjugates tagged with the chemoselective sensitivity boosters.

In an aspect the chemoselective sensitivity booster is for tagging a peptide or molecule with peptide like reactivity of natural and synthetic origin utilizing the nucleophile-electrophile reaction.

The peptide coverage can be enhanced from <21% with untagged peptides to >74% with the tagged peptides, in mass spectrometry.

The sensitivity booster provides for the MS detection of a peptide up to attomolar concentration. Further enables enhancement in the detection of peptides from a protein digest. The reagent exhibits excellent chemoselectivity in the labelling of the mixture of peptides and results in a mass change of 374 Da for one type of sensitivity booster. Its reaction with C-terminus lysine outcompetes all the other side reactions. In the absence of C-Lys, it exclusively reacts with the N-terminus α-amine. Besides, it ensures excellent coverage of fragments in the MS-MS and renders a simplified spectrum with either y or b ions.

Figure 2:
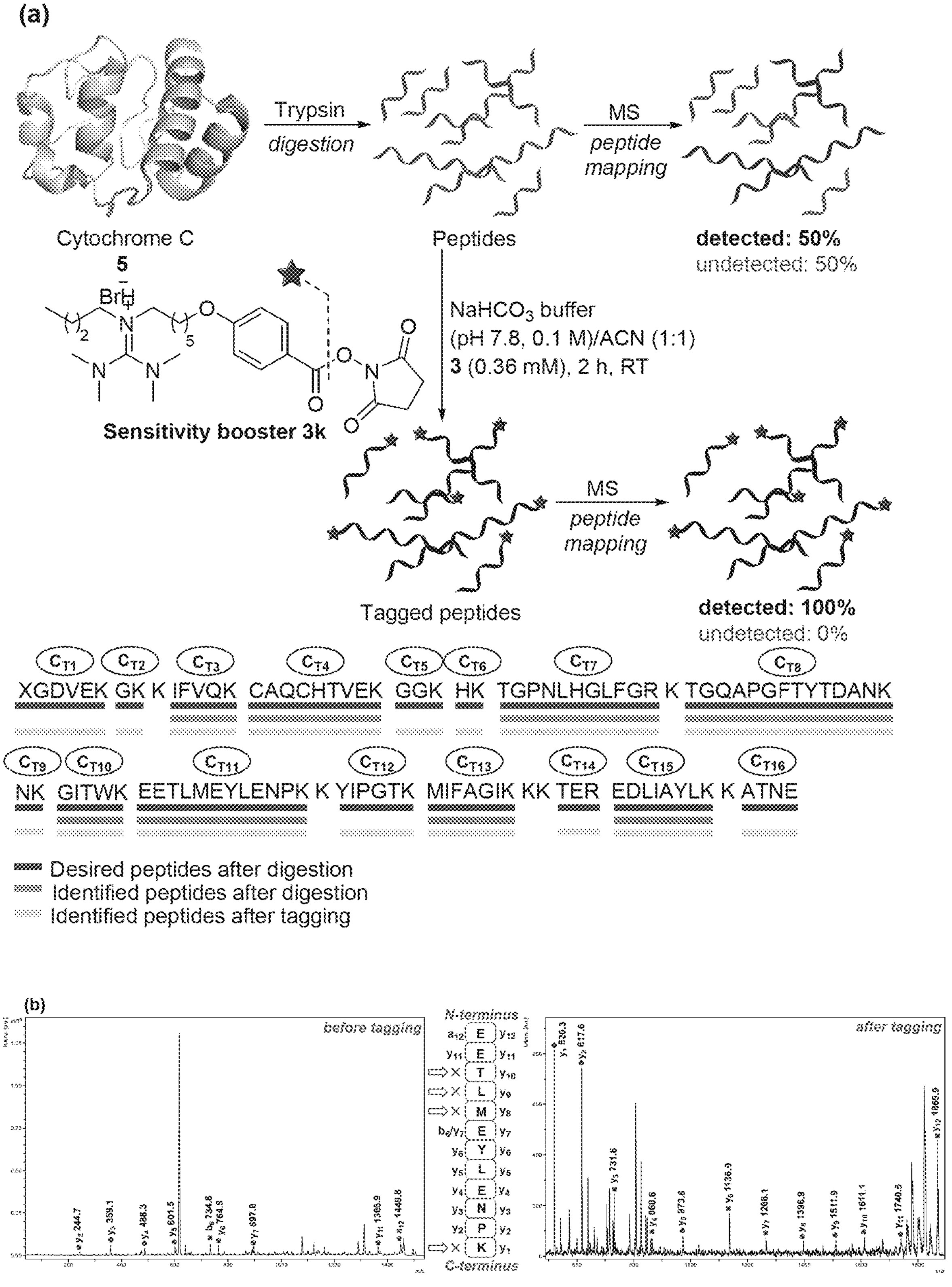

In an aspect, the sensitivity of the booster in detection was estimated with Cytochrome C (5) (SEQ ID NO: 5). The protein (5) was digested with trypsin and subjected the mixture of peptides to MALDI-MS (FIG. 2). The possible tryptic fragments $C_{T1}$-$C_{T16}$ are shown ($C_{T1}$: SEQ ID NO: 58, $C_{T3}$: SEQ ID NO: 59, $C_{T4}$: SEQ ID NO: 60, $C_{T7}$: SEQ ID NO: 61, $C_{T8}$: SEQ ID NO. 62, $C_{T10}$: SEQ ID NO: 63, $C_{T11}$: SEQ ID NO: 64, $C_{T12}$: SEQ ID NO: 65, $C_{T13}$: SEQ ID NO: 66, $C_{T15}$: SEQ ID NO: 67, $C_{T16}$: SEQ ID NO: 68). Eight out of sixteen peptides are not detected due to suppression by other peptides or matrix (peptides $C_{T1}$, $C_{T2}$, $C_{T5}$, $C_{T6}$, $C_{T9}$, $C_{T12}$, $C_{T14}$ and $C_{T16}$ (FIG. 2). Further in parallel, the protein (5) digested with trypsin containing mixture of peptides was vortexed with the sensitivity booster reagent (3, 2.5 equivalent per peptide). After 2 h, the reaction mixture was analysed without any further treatment or purification. The peaks for all sixteen peptides were observed ($C_{T1}$-$C_{T16}$, FIG. 2 *b*). The peptide EETLMEYLENPK ($C_{T11}$, SEQ ID NO: 64) was further subjected to MS-MS. The untagged form gives a combination of fragments from both N- and C-terminus (FIGS. 2*a* and 2*b*). Besides, four fragments remain undetected. For the tagged peptide, all the fragments are observed in the form of "y ions" in a simplified spectrum (FIGS. 2 and 2*b*).

Figure 4:
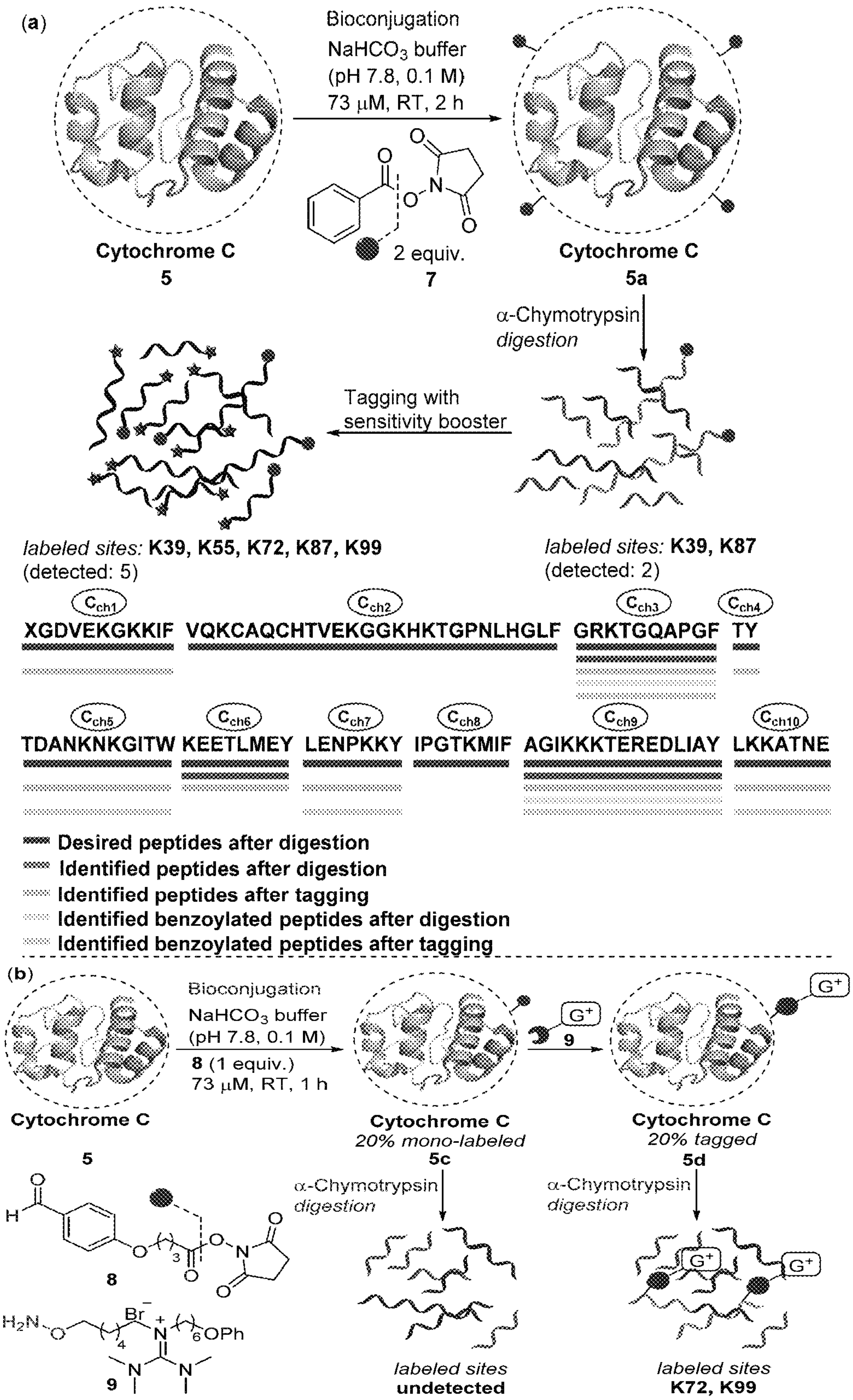

In an aspect, the sensitivity booster detects the heterogeneity of mono-labeled Cytochrome C bioconjugate (FIG. 4).

In an aspect for analysis of an antibody, trastuzumab (6, FIG. 3), was denatured to reduce the disulfide bonds to separate the heavy and light chains and alkylated to prevent the re-bridging. This mixture was treated with trypsin and the peptide mapping was performed with MALDI-MS. Only 21% of the peptides in the spectrum was observed (FIG. 3). In parallel, the mAb digest was mixed with the sensitivity booster (3, 5 equivalents per peptide, 6 h). It resulted in improvement in sensitivity of tagged peptides and allowed the detection of 74% of the peptides as provided in Table 1-3.

Heavy Chain of Antibody Sequences as Mentioned Below:

(SEQ ID NO: 6)

EVQLVESGGGLVQPGGSLRLSCAASGFNIKDTYIHWVRQAPGKGL

EWVARIYPTNGYTRYADSVKGRFTISADTSKNTAYLQMNSLRAED

TAVYYCSRWGGDGFYAMDYWGQGTLVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYNSTYRVVSVLTVLHQD

WLNGKEYKCKVSNKALPAPIEKTISKAKGQPREPQVYTLPPSREE

-continued

MTKNQVSLTCLVKGFYPSDIAVEWESNGQPENNYKTTPPVLDSDG

SFFLYSKLTVDKSRWQQGNVFSCSVMHEALHNHYTQKSLSLSPG

Light Chain of Antibody Sequences as Mentioned Below:

(SEQ ID NO: 7)

DIQMTQSPSSLSASVGDRVTITCRASQDVNTAVAWYQQKPGKAPK

LLIYSASFLYSGVPSRFSGSRSGTDFTLTISSLQPEDFATYYCQQ

HYTTPPTFGQGTKVEIKRTVAAPSVFIFPPSDEQLKSGTASVVCL

LNNFYPREAKVQWKVDNALQSGNSQESVTEQDSKDSTYSLSSTLT

LSKADYEKHKVYACEVTHQGLSSPVTKSFNRGEC

TABLE 1

Sequencing of Heavy chain fragment of antibody.
Position Native Tagged

| Entry | Heavy chain peptide sequence | Position | Native | Tagged |
|---|---|---|---|---|
| HC1 | EVQLVESGGGLVQPGGSLR (SEQ ID NO: 8) | 1-19 | + | − |
| HC2 | LSCAASGFNIK (SEQ ID NO: 9) | 20-30 | + | + |
| HC3 | DTYIHWVR (SEQ ID NO: 10) | 31-38 | − | − |
| HC4 | QAPGK (SEQ ID NO: 11) | 39-43 | − | + |
| HC5 | GLEWVAR (SEQ ID NO: 12) | 44-50 | + | − |
| HC6 | IYPTNGYTR (SEQ ID NO: 13) | 51-59 | + | − |
| HC7 | YADSVK (SEQ ID NO: 14) | 60-65 | − | + |
| HC8 | GR | 66-67 | + | + |
| HC9 | FTISADTSK (SEQ ID NO: 15) | 68-76 | − | − |
| HC10 | NTAYLQMNSLR (SEQ ID NO: 16) | 77-87 | + | + |
| HC11 | AEDTAVYYCSR (SEQ ID NO: 17) | 88-98 | − | − |
| HC12 | WGGDGFYAMDYWGQGTLVTVSSASTK (SEQ ID NO: 18) | 99-124 | − | + |
| HC13 | GPSVFPLAPSSK (SEQ ID NO: 19) | 125-136 | − | + |
| HC14 | STSGGTAALGCLVK (SEQ ID NO: 20) | 137-150 | − | + |
| HC15 | DYFPEPVTVSWNSGALTSGVHTFPAVL QSSGLYSLSSVVTVPSSSLGTQTYICN VNHKPSNTK (SEQ ID NO: 21) | 151-213 | − | − |
| HC16 | VDK | 214-216 | − | − |
| HC17 | VEPK (SEQ ID NO: 22) | 218-221 | − | − |
| HC18 | SCDK (SEQ ID NO: 23) | 222-225 | − | − |
| HC19 | THTCPPCPAPELLGGPSVFLFPPKPK (SEQ ID NO: 24) | 226-251 | − | + |
| HC20 | DTLMISR (SEQ ID NO: 25) | 252-258 | − | + |
| HC21 | TPEVTCVVVDVSHEDPEVK (SEQ ID NO: 26) | 259-277 | − | + |
| HC22 | FNWYVDGVEVHNAK (SEQ ID NO: 27) | 278-291 | − | + |
| HC23 | TKPR (SEQ ID NO: 28) | 292-295 | − | + |
| HC24 | EEQYNSTYR (SEQ ID NO: 29) | 296-304 | − | − |
| HC25 | VVSVLTVLHQDWLNGK (SEQ ID NO: 30) | 305-320 | − | + |

TABLE 1-continued

| Sequencing of Heavy chain fragment of antibody. Position Native Tagged | | | | |
|---|---|---|---|---|
| Entry | Heavy chain peptide sequence | Position | Native | Tagged |
| HC26 | EYK | 321-323 | + | + |
| HC27 | CK | 324-325 | − | + |
| HC28 | VSNK (SEQ ID NO: 31) | 326-329 | − | + |
| HC29 | ALPAPIEK (SEQ ID NO: 32) | 330-337 | − | + |
| HC30 | TISK (SEQ ID NO: 33) | 338-341 | − | + |
| HC31 | AK | 342-343 | − | + |
| HC32 | GQPR (SEQ ID NO: 34) | 344-347 | − | − |
| HC33 | EPQVYTLPPSR (SEQ ID NO: 35) | 348-358 | − | + |
| HC34 | EEMTK (SEQ ID NO: 36) | 359-363 | + | + |
| HC35 | NQVSLTCLVK (SEQ ID NO: 37) | 364-373 | + | + |
| HC36 | GFYPSDIAVEWESNGQPENNYK (SEQ ID NO: 38) | 374-395 | − | + |
| HC37 | TTPPVLDSDGSFFLYSK (SEQ ID NO: 39) | 396-412 | − | + |
| HC38 | LTVDK (SEQ ID NO: 40) | 413-417 | − | + |
| HC39 | SR | 418-419 | − | + |
| HC40 | WQQGNVFSCSVMHEALHNHYTQK (SEQ ID NO: 41) | 420-442 | − | + |
| HC41 | SLSLSPG (SEQ ID NO: 42) | 443-449 | + | + |

| Entry | Light chain peptide sequence | Position | Native | Tagged |
|---|---|---|---|---|
| LC1 | DIQMTQSPSSLSASVGDR (SEQ ID NO: 43) | 01-18 | + | + |
| LC2 | VTITCR (SEQ ID NO: 44) | 19-24 | - | + |
| LC3 | ASQDVNTAVAWYQQKPGK (SEQ ID NO: 45) | 25-42 | - | + |
| LC4 | APK | 43-45 | - | - |
| LC5 | LLIYSASFLYSGVSR (SEQ ID NO: 46) | 46-61 | + | - |
| LC6 | FSGSR (SEQ ID NO: 47) | 62-66 | - | - |
| LC7 | SGTDFTLTISSLQPEDFATYYCQQHYTTPPTFGQGTK (SEQ ID NO: 48) | 67-103 | - | + |
| LC8 | VEIK (SEQ ID NO: 49) | 104-108 | - | + |
| LC9 | TVAAPSVFIFPPSDELK (SEQ ID NO: 50) | 109-126 | + | + |
| LC10 | SGTASVVCLLNNFYPR (SEQ ID NO: 51) | 127-142 | - | + |
| LC11 | EAK | 143-145 | - | + |

-continued

| Entry | Light chain peptide sequence | Position | Native | Tagged |
|---|---|---|---|---|
| LC12 | VQWK (SEQ ID NO: 52) | 146-149 | - | + |
| LC13 | VDNALQSGNSQESVTEQDSK (SEQ ID NO: 53) | 150-169 | - | + |
| LC14 | DSTYSLSSTLTLSK (SEQ ID NO: 54) | 170-183 | - | + |
| LC15 | ADYEK (SEQ ID NO: 55) | 184-188 | - | + |
| LC16 | HK | 189-190 | - | + |
| LC17 | VYACBVTHQGLSSPVTK (SEQ ID NO: 56) | 191-207 | - | + |
| LC18 | SFNR (SEQ ID NO: 57) | 208-211 | - | - |
| LC19 | GEC | 212-214 | - | + |

TABLE 3

| Antibody - total coverage from sequencing. | | | | |
|---|---|---|---|---|
| Entry | Heavy chain | Light chain | Total | % Coverage |
| Native | 10/41 | 03/19 | 13/60 | 21% |
| Tagged | 30/41 | 14/19 | 44/60 | 74% |
| Unmatched | 3 | 1 | 48/60 | 80% |

Overall, 80% detection of the peptides combining the results from untagged and tagged samples.

In one embodiment the sensitivity of the chemoselective sensitivity booster was tested with a protein bioconjugate. Cytochrome C (5) was treated with benzoic acid N-hydroxysuccinimide ester (NHS) (7, 2 equiv.) at room temperature for 2 h. The MALDI-MS confirms the heterogeneous labeling and formation of mono-, bis-, tris-, and tetra-labelled cytochrome C (5a, FIG. 4). As NHS ester (7) is chemoselective for the Lys residues, α-chymotrypsin was taken for the digestion of 5a. The possible chymotryptic fragments $C_{ch1}$-$C_{ch10}$ are shown ($C_{ch1}$: SEQ ID NO. 69, $C_{ch2}$: SEQ ID NO: 70, $C_{ch3}$: SEQ ID NO: 71, $C_{ch5}$: SEQ ID NO: 72, $C_{ch6}$: SEQ ID NO: 73, $C_{ch7}$: SEQ ID NO: 74, $C_{ch8}$: SEQ ID NO: 75, $C_{ch9}$: SEQ ID NO: 76, $C_{ch10}$: SEQ ID NO: 77). Two labelled peptides were detected in the MS spectrum. Subsequently, the MS-MS confirmed K39 and K87 as the sites of labelling (FIG. 4). In parallel, sensitivity booster (3) was mixed with the protein digest. This resulted in five sites of labelling (K39, K55, K72, K87, and K99) after MS and MS-MS (FIG. 4). Further the sensitivity booster tagged peptides show all the fragments and allow unambiguous identification of the labelled sites.

Further, an aldehyde functionalized N-hydroxysuccinimide ester derivative (8) and alkoxy-amine derivative of the sensitivity booster (9) was tested for the sensitivity. The electrophile (8) was missed with cytochrome C (5) at 25° C. for 1 h. The MALDI-MS confirmed the formation of mono-labeled cytochrome C (5c, FIG. 4). The cytochrome C 5c was digested with α-chymotrypsin and the peptide mixture was analysed by MS. The labeled peptide is not observed, and the overall sequence coverage remained poor (30% FIG. 4). Further, the sensitivity booster (9) was mixed to the modified protein (5c) at 25° C. and incubated for 4 h. The reaction resulted in 100% conversion of 5c to the oxime (5d). The samples further digested for peptide mapping. There is selective enhancement of sensitivity for the tagged peptides and two lysine residues, K72 and K99, are modified in the mono-labeled cytochrome C (FIG. 4).

The method of tagging the peptides with the sensitivity boosters promotes the identification of sites of modification with higher efficiency than the classical method.

EXAMPLES

The invention is described in detail in the above figures and description, and the following examples below are provided as an illustration and are not intended to restrict the scope of the invention in any manner. Any embodiments that may be apparent to a person skilled in the art are deemed to fall within the scope of the present invention.

Materials and General Information:

The reagents, proteins, and enzymes were purchased from Sigma-Aldrich. Aqueous buffers were prepared freshly using Millipore Grade I water (Resistivity>5 MΩ cm, Conductivity<0.2 ρS/cm, TOC<30 ppb). The final pH was adjusted using pH meter Mettler Toledo (FE20). All the solvents used in synthesis were reagent grade. The reaction mixture was stirred for small molecules (Heidolph, 500-600 rpm), whereas it was vortexed in incubator shaker Thermo Scientific MaxQ 8000 (350 rpm) for proteins. UV spectra were recorded on Shimadzu UV-1800 UV-Vis spectrophotometer. Merck Amicon centrifugal spin concentrators (MWCO, 3 kD) were used for removal of small molecules and salts. Samples were lyophilized using CHRiST ALPHA 2-4 LD plus lyophilizer. Peptide was synthesized by SPPS using Fmoc chemistry on Biotage Syro I parallel peptide synthesis system.

Chromatography: A few samples containing non-polar solvent impurities were triturated with pentane. For reactions where chromatography was involved, flash column chromatography was carried out on Combiflash Rf 200 using 230-400 mesh silica gel. Thin-layer chromatography (TLC) was performed on Merck (TLC Silica gel 60 $F_{254}$) and visualized using a UV lamp (254 nm) and stains such as iodine, ninhydrin, cerium sulfate (yellow dip). Agilent Technologies 1200 series reverse phase preparative HPLC paired to a PDA and single-quad 6130 mass detector was used for purification of 2d, 2e, 2 h, 2i, 2j, and 2k.

Nuclear magnetic resonance: $^{1}H$, $^{13}C$ NMR spectra were recorded on Bruker Avance III 400 MHz and 500 MHz NMR spectrometer. $^{1}H$ NMR spectra were referenced to TMS (0 ppm), $^{13}C$ NMR spectra were referenced to $CDCl_3$ (77.16 ppm), $D_2O$ (4.79 ppm) and DMSO-$d_6$ (39.52 ppm). Peak multiplicities are designated by the following abbreviations: s, singlet; d, doublet; t, triplet; q, quartet; m, multiplet; dd, doublet of doublets. Spectra were recorded at 298 K.

Mass spectrometry: Low resolution mass spectra (ESI) were collected on an Agilent Technologies 1200 series HPLC paired to a single-quad 6130 mass spectrometer. Bruker Daltonics MicroTOF-Q-II with electron spray ionization (ESI) was used for the HRMS data. Matrix assisted laser desorption/ionisation time of flight mass spectrometry was performed with Bruker Daltonics UltrafleXtreme and Flex control version 3.4 software. Sinapinic acid and α-cyano-4-hydroxycinnamic acid (HCCA) matrix were used. Peptide mass' and fragment ion calculator were used for peptide mapping and sequencing.

Example 1

1.1. Procedure for Dipeptide Labeling: 2a

Gly-Phe-$NH_2$ 1 (2.21 mg, 0.01 mmol) was taken in a clean and dry 5 ml vial charged with magnetic stir bar containing 0.1 ml solution of acetic anhydride. The reaction was allowed to stir at room temperature for 2 h. The reaction mixture was concentrated under the reduced pressure. The trituration with ether (1 ml) resulted in the title compound (S)-2-(2-acetamidoacetamido)-3-phenylpropanamide 2a.

1.2. Procedure for Dipeptide Labeling: 2b, 2d-2f, 2h-2j

N-hydroxysuccinimide S2 (23.0 mg, 0.2 mmol) and N-ethyl-N'-(3-dimethylaminopropyl)carbodiimide hydrochloride (38.3 mg, 0.2 mmol) were taken in a clean and dry vial (5 ml) charged with magnetic stir bar and dichloromethane (1 ml). The respective acid (S1, S11, 514, S19, 530, S33, and S36; 0.05 mmol) was added and allowed to stir at room temperature for 2 h. The reaction was followed by thin layer chromatography. The reaction mixture was diluted with dichloromethane (9 ml) and extracted (2×8 ml) with water.

The organic layer was dried over $Na_2SO_4$, concentrated under reduced pressure, and the crude reagent was transferred into a vial (5 ml) charged with magnetic stir bar. The mixture was resuspended in acetonitrile (200 μl) and Gly-Phe-$NH_2$ 1 (4.42 mg, 0.02 mmol) and triethyl amine (2.76 μl, 0.02 mmol) were added. The reaction mixture was allowed to stir at room temperature for 2 h. Further, it was diluted to 500 μl by the addition of acetonitrile and purified by preparative HPLC to render tagged Gly-Phe-$NH_2$ (2b, 2d-2f, 2h-2j).

1.3. Procedure for Dipeptide Labeling: 2c, 2g, 2k

The peptide Gly-Phe-$NH_2$ 1 (4.42 mg, 0.02 mmol) was taken in a clean and dry vial (5 ml) charged with magnetic stir bar and acetonitrile (0.2 ml). The N-hydroxysuccinimide esters of respective reagents S6, S27 and 3 (0.05 mmol) and triethylamine (2.76 gl, 0.02 mmol) were added through micropipette and allowed to stir at room temperature for 2 h. The reaction mixture was diluted to 500 μl by the addition of acetonitrile and subjected to purification by prep-HPLC to render the tagged Gly-Phe-$NH_2$ (2c, 2g, 2k).

Example 2

2.1 Procedure for Checking Intensity Ratios of Native and Tagged Peptides

The peptide Gly-Phe-$NH_2$ 1 (1.105 mg, 0.005 mmol) was taken in a clean and dry Eppendorf tube containing acetonitrile (1 ml). The tagged Gly-Phe-$NH_2$ 2 (0.005 mmol) was taken in another clean and dry Eppendorf tube containing acetonitrile (1 ml). Equal volume (1 μl) of each solution were taken from the stock solution and re-diluted with acetonitrile (1 ml) in another Eppendorf. The mixture was vortexed, and 0.5 ml was transferred to the HPLC vial (3 ml) for ESI-MS. Subsequently, the intensity ratios were analyzed (ESI FIG. 1*b*).

2.2. Procedure for Polar and Non-Polar Peptide Labeling

The respective peptide 4 (9 nmol) was dissolved in $NaHCO_3$ buffer (0.1 M, pH 7.8, 25 μl) and was taken into Eppendorf tube (1.5 ml). To this reaction mixture, the sensitivity booster 3 (2.5 equiv. per peptide i.e. 12.8 μg, 22.5 nmol) dissolved in acetonitrile (25 μl) was added. The reaction mixture was incubated at room temperature for 2 h. Subsequently, the sample was subjected to MALDI-ToF-MS and MS-MS using α-cyano-4-hydroxycinnamic acid solution as a matrix.

Example 3

3.1. Procedure for in-Solution Digestion of Protein: (FIG. 2)

All solutions were made immediately prior to use.

1. Denaturation: Cytochrome C 5 solution (10 μl) containing cytochrome C (0.1 mg) in 6 M urea, 100 mM tris and 10 mM $CaCl_2$ (pH 7.8), was taken in 1.5 ml Eppendorf tube and incubated at 37° C. for 1 h.
2. Spin concentration: The mixture was diluted to 500 μl with grade I water, and the volume was reduced to 200 μl through spin concentration.
3. Digestion: The trypsin solution (10 μl; trypsin in 1 mM HCl dissolved in 0.1 M tris and 0.01 M $CaCl_2$) containing 1 μg of trypsin (trypsin/cytochrome C, 1:100) was added to the reaction mixture. It was incubated at 37° C. for 18 h, and the pH of digested solution was adjusted to <6 (verified by pH paper) by adding 0.5% trifluoroacetic acid. Subsequently, the sample was used for MS and MS-MS.

3.2. Procedure for Labeling the Digested Protein: (FIG. 2)

The cytochrome C 5 digest from previous step was lyophilized and re-dissolved in 50 μl of $NaHCO_3$ buffer (0.1 M, pH 7.8) in an Eppendorf tube covered with aluminium foil. From this stock solution, 12.5 μl of cytochrome C digest (0.023 mg, 1.825 nmol) taken into another 1.5 ml Eppendorf tube covered with aluminium foil. To this reaction mixture, the sensitivity booster 3 [2.5 equiv. for each peptide (0.041 mg, 73 nmol)], dissolved in 12.5 μl of acetonitrile solution, was added. The reaction mixture was incubated at room temperature for 2 h. Reaction was subjected to MALDI-ToF-MS using α-cyano-4-hydroxycinnamic acid solution as a matrix. Reaction was analyzed and subsequently, the sample was used to MALDI MS/MS investigations.

Example 4

4.1. Procedure for in-Solution Digestion of Antibody: (FIG. 3)

All solutions were made immediately prior to use.

1. Denaturation: Trastuzumab (6) solution (100 μl) containing trastuzumab 6 (1 mg) and 6 M guanidinium hydrochloride salt (155 μl), was taken in a 1.5 ml Eppendorf tube.
2. Disulfide reduction: To this solution, 10 μl of reducing agent (0.2 M DTT, 0.1 M tris, and 0.01 M $CaCl_2$)) was added and sample was vortexed for 1 h at 100° C.
3. Sulfhydryl alkylation: To this solution, 20 μl of alkylating agent (0.2 M iodoacetamide, 0.1 M tris, and 0.01 M $CaCl_2$)) was added and incubated (in dark) for 1 h at 25° C.
4. Spin concentration: The digestion mixture was diluted to 500 μl with grade I water, desalted with centrifugal spin concentration while reducing the volume to 200 μl.
5. Trypsin: The trypsin solution (10 μl; trypsin in 1 mM HCl dissolved in 0.1 M tris and 0.01 M $CaCl_2$)) containing 100 μg of trypsin (trypsin/antibody, 1:10 w/w) was added to the above solution. The reaction mixture was incubated at 37° C. for 18 h. The pH of digested solution was adjusted to <6 (verified by pH paper) by adding 0.5% trifluoroacetic acid. Subsequently, the hydrolysis at C-termini of Lys and Arg resulted in the digest. The sample was used for MS.

4.2. Procedure for Labeling the Antibody Digest (FIG. 3)

The antibody digest from previous step was lyophilized and re-dissolved in 67 μl of $NaHCO_3$ buffer (0.1 M, pH 7.8) in an Eppendorf tube covered with aluminium foil. From this stock solution, 10 μl of antibody digest containing (0.15 mg, 1 nmol) taken into a 1.5 ml Eppendorf tube covered with aluminium foil. The sensitivity booster 3 (0.24 mg, 420 nmol; i.e. 5 equivalents per peptide) dissolved in 10 μl of acetonitrile solution was added to the reaction mixture. The reaction mixture was incubated at room temperature for 6 h.

The sample was subjected to MALDI-ToF-MS using α-cyano-4-hydroxycinnamic acid as a matrix.

Example 5

5.1. Procedure for Protein Labeling: (FIG. 4*a*)

Cytochrome C 5 (0.092 mg, 7.3 nmol) was dissolved in 80 μl of phosphate buffer (0.1 M, pH 7.0) and taken into a 1.5 ml Eppendorf tube covered with aluminium foil. 2,5-Dioxopyrrolidin-1-yl benzoate 7 (0.0032 mg, 14.6 nmol) was dissolved in acetonitrile (20 g1) and added to the reaction mixture. It was incubated at room temperature for 2 h and the reaction was followed by MALDI-ToF-MS using sinapinic acid as matrix. After 2 h, the reaction mixture was further diluted with water (0.4 ml) and lyophilized after centrifugal spin concentration to remove the unreacted reagent and salts. The sample was further utilized for digestion and sequencing.

5.2. Procedure for in-Solution Digestion of Protein: (FIG. 4*a*)

All solutions were made immediately prior to use.

1. Denaturation: Cytochrome C 5a solution (10 1) containing cytochrome C 5a (0.092 mg) in 6 M urea, 100 mM tris and 10 mM $CaCl_2$ (pH 7.8), was taken in 1.5 ml Eppendorf tube and incubated at 37° C. for 1 h.
2. Spin concentration: The mixture was diluted to 500 μl with grade I water, then subjected to centrifugal spin concentration for desalting of the sample. A fraction of 200 μl of digestion mixture was collected for the next step.
3. α-Chymotrypsin: The α-chymotrypsin solution (10 μl; α-chymotrypsin in 1 mM HCl dissolved in 0.1 M tris and 0.01 M $CaCl_2$)) containing 1 μg of trypsin (α-chymotrypsin/cytochrome C, 1:100) was added to the reaction mixture. It was incubated at 37° C. for 18 h, and the pH of digested solution was adjusted to <6 (verified by pH paper) by adding 0.5% trifluoroacetic acid. Subsequently, the hydrolysis at C-termini of Tyr, Phe, and Trp (partial hydrolysis with Leu and Met) resulted in the digest. Next, the sample was used for MS investigations.

5.3. Procedure for Labeling the Protein Digest (FIG. 4*a*)

The cytochrome C 5a digest from previous step was lyophilized and re-dissolved in 50 1 of $NaHCO_3$ buffer (0.1 M, pH 7.8) in an Eppendorf tube covered with aluminium foil. From this stock solution, 12.5 μl of cytochrome C digest (0.023 mg, 1.825 nmol) taken into another 1.5 ml Eppendorf tube covered with aluminium foil. To this reaction mixture, the sensitivity booster 3 [2.5 equiv. for each peptide (0.026 mg, 45 nmol)], dissolved in 12.5 μl of acetonitrile solution, was added. The reaction mixture was incubated at room temperature for 2 h. Reaction was subjected to MALDI-ToF-MS using α-cyano-4-hydroxycinnamic acid solution as a matrix. Reaction was analyzed and subsequently, the sample was used to MALDI MS/MS investigations.

5.4. Procedure for Protein Labeling: 5c (FIG. 4*a*)

Under minimized light, Cytochrome C 5 (0.092 mg, 7.3 nmol) was dissolved in 80 μl of phosphate buffer (0.1 M, pH 7.0) and taken into aluminium foil covered 1.5 ml Eppendorf tube. 2,5-Dioxopyrrolidin-1-yl 4-(4-formylphenoxy)butanoate 8 (0.0022 mg, 7.3 nmol), dissolved in 20 μl of acetonitrile solution, was added to reaction mixture. Reaction mixture was incubated at room temperature for 1 h and was further diluted with water (0.4 ml). The buffer and unreacted reagent was subjected to spin concentration for desalting and concentrated by lyophilization. The sample was further utilized for digestion and sequencing.

5.5. Procedure for Protein Labeling: 5d (FIG. 4*b*)

Under minimized light, Cytochrome C 5 (0.092 mg, 7.3 nmol) dissolved in 80 μl of phosphate buffer (0.1 M, pH 7.0) and taken into aluminium foil covered 1.5 ml Eppendorf tube. 2,5-Dioxopyrrolidin-1-yl-4-(4-formylphenoxy)butanoate 8 (0.0022 mg, 7.3 nmol), dissolved in 20 μl of acetonitrile solution, was added to reaction mixture. Reaction mixture was incubated at room temperature for 1 h. 6-(aminooxy)-N-(bis(dimethylamino)methylene)-N-(6-phenoxyhexyl)hexan-1-aminium bromide 9 (0.71 mg, 14.6 μmol), dissolved in 100 μl of (1:1) acetonitrile and phosphate buffer (0.1 M, pH 7.0), was added and allowed to incubate at room temperature for 4 h. Reaction mixture was further diluted with water (0.4 ml). The buffer and unreacted reagent was subjected to spin concentration for desalting and concentrated by lyophilization. The sample was further utilized for digestion and sequencing.

Example 6

Procedure for Synthesis of Reagents

6.1 Procedure for Synthesis of Gly-Phe 1

Solid phase peptide synthesis (Biotage Syro I peptide synthesizer with standard Fmoc-protecting group strategy was used for generating the required pool of peptides. Rink amide resin (loading capacity: 0.78 mmol/g) was used for synthesis of all the peptides. All Fmoc amino acids were activated by in situ HBTU/DIPEA activation procedure. The cleavage from the solid support and the simultaneous deprotection of all side chain residues were performed by suspending the fully protected compound resin in TFA:$H_2O$:TIS (95:2.5:2.5) for 3 h. The analytically pure peptides were isolated by precipitation in cold diethyl ether or by reverse phase preparative HPLC.

6.2 Procedure for Synthesis of (S)-2-(2-Acetamidoacetamido)-3-Phenylpropanamide 2a

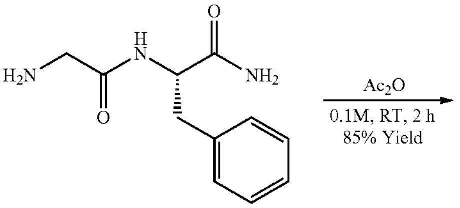

1

-continued

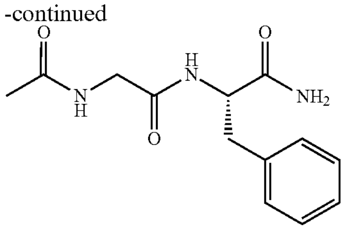

2a

Gly-Phe-$NH_2$ 1 (2.21 mg, 0.01 mmol) was taken in a clean and dry 5 ml vial charged with magnetic rice bead containing the 100 µl solution of acetic anhydride. Reaction mixture was allowed to stir at room temperature for 2 h and concentrated. 1 ml of ether was added to this crude reaction mixture and triturated to give the title compound (S)-2-(2-acetamidoacetamido)-3-phenylpropanamide 2a (2.23 mg, 85% yield) as a white solid. $^1H$ NMR (500 MHz, $D_2O$) δ: 7.40 (m, 2H), 7.34 (t, J=7.4 Hz, 1H), 7.30 (d, J=7.0 Hz, 2H), 4.63 (dd, J=9.0, 5.7 Hz, 1H), 3.82 (m, 2H), 3.22 (dd, J=14.0, 5.7 Hz, 1H), 3.01 (dd, J=14.0, 9.0 Hz, 1H), 2.02 (s, 3H) ppm. $^{13}C$ NMR (126 MHz, $D_2O$) δ 175.8, 174.7, 171.5, 136.4, 129.1, 128.7, 127.1, 54.5, 42.4, 36.9, 21.6 ppm. HRMS (ESI) $[M+Na]^+$ calcd. for $C_{13}H_{17}N_3O_3$ 286.1162, found 286.1136.

6.3 Procedure for Synthesis of Sensitivity Booster 2,5-dioxopyrrolidin-1-yl picolinate (S53) and (S)—N-(2-((1-amino-1-oxo-3-phenylpropan-2-yl)amino)-2-oxoethyl)picolinamide 2b

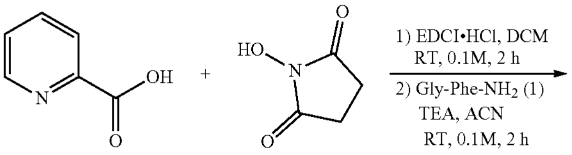

S1 S2

-continued

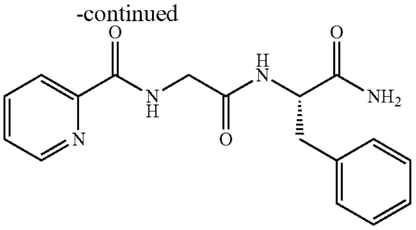

2b

N-Hydroxysuccinimide S2 (23.0 mg, 0.2 mmol) and N-ethyl-N'-(3-dimethylaminopropyl)carbodiimide hydrochloride (38.3 mg, 0.2 mmol) was taken in a clean and dry 5 ml vial charged with magnetic stir bar containing the 1 ml solution of dichloromethane. Picolinic acid S1 (12.3 mg, 0.1 mmol) was added and allowed to stir at room temperature for 2 h to give the sensitivity booster S53. Reaction was followed by thin layer chromatography. The reaction mixture was diluted with 9 ml of dichloromethane and extracted with water (2×8 ml). The organic layer was dried over $Na_2SO_4$, concentrated and crude reagent was transferred into 5 ml vial charged with magnetic stir bar. 0.2 ml of acetonitrile solution was added to this crude reagent contained in the above vial. Gly-Phe-$NH_2$ 1 (4.42 mg, 0.02 mmol) and triethylamine (2.76 1, 0.02 mmol) was added through micro pipette and allowed to stir at room temperature for 2 h. Reaction mixture was concentrated under reduced pressure. 0.5 ml of dichloromethane was added twice to this and triturated to give the title compound (S)—N-(2-((1-amino-1-oxo-3-phenylpropan-2-yl)amino)-2-oxoethyl)picolinamide 2b (0.9 mg, 30% yield) as pale yellow solid. $^1H$ NMR (500 MHz, $CD_3OD$) δ 8.54 (d, J=4.6 Hz, 1H), 7.99 (d, J=7.8 Hz, 1H), 7.87 (td, J=7.7, 1.7 Hz, 1H), 7.47 (m, 1H), 7.14-7.08 (m, 4H), 7.07-7.02 (m, 1H), 4.55 (dd, J=8.8, 5.4 Hz, 1H), 3.94 (m, 2H), 3.08 (dd, J=13.9, 5.4 Hz, 1H), 2.83 (dd, J=13.9, 8.9 Hz, 1H) ppm. $^{13}C$ NMR (126 MHz, $CD_3OD$) δ 174.6, 169.8, 165.9, 149.2, 148.5, 137.3, 136.9, 128.9, 128.0, 126.5, 126.3, 121.8, 54.3, 42.2, 37.3 ppm. HRMS (ESI) $[M+Na]^+$ calcd. for $C_{13}H_{18}N_4O_3$ 349.1271, found 349.1296.

6.4 Synthesis of Sensitivity Booster 2,5-dioxopyrrolidin-1-yl 4-(dibenzylamino)benzoate (S6) and (S)—N-(2-((1-amino-1-oxo-3-phenylpropan-2-yl)amino)-2-oxoethyl)-4-(dibenzylamino)benzamide 2c

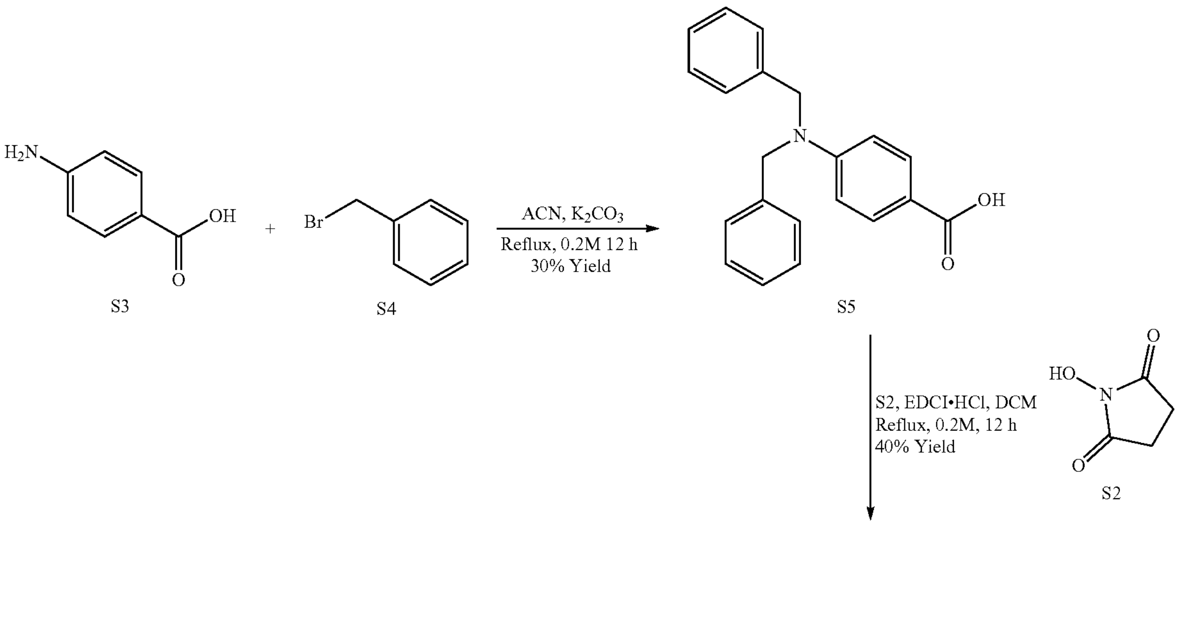

S3 S4 S5 S2

-continued

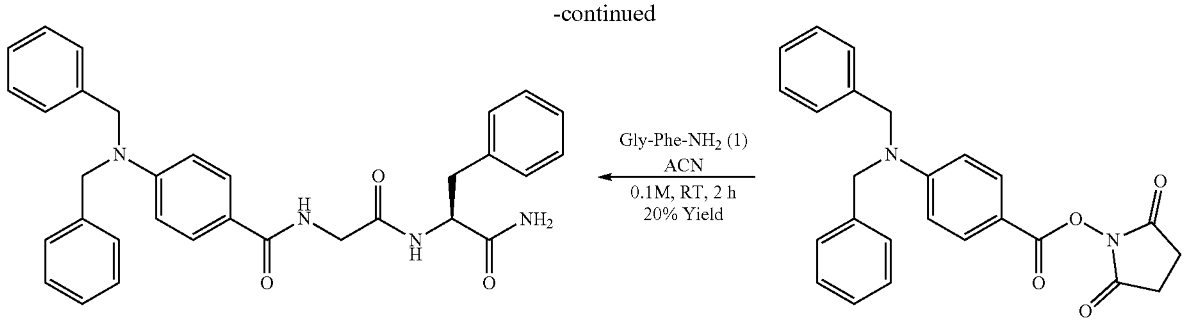

2c S6

Synthesis of 4-(Dibenzylamino)benzoic Acid S5[2]

4-Amino benzoic acid S3 (274 mg, 2 mmol) and potassium carbonate (680 mg, 4.92 mmol) were taken in a clean and dry 100 ml round bottom flask charged with magnetic stir bar containing 10 ml solution of acetonitrile. The resulting reaction mixture was refluxed for 30 min, followed by the addition of benzyl bromide S4 (470 μl, 4 mmol). The reaction mixture was refluxed at 78° C. for 24 h. The reaction mixture was then poured into water, and the resulting precipitate was filtered off, washed with water, and dried. The resulting residue was purified by silica gel column chromatography (hexane/EtOAC, 95:5, $R_f$ 0.25), thereby affording the desired product as a white solid 4-(dibenzylamino)benzoic Acid S5 (0.28 g, 36% Yield). $^1$H NMR (500 MHz, $CDCl_3$): δ 7.91 (m, 2H), 7.34 (m, 4H), 7.28 (t, J=7.3 Hz, 2H), 7.22 (d, J=7.7 Hz, 4H), 6.73 (m, 2H), 4.72 (s, 4H) ppm. $^{13}$C NMR (126 MHz, $CDCl_3$): δ 172.0, 153.2, 137.2, 132.2, 128.8, 127.3, 126.4, 116.2, 111.3, 54.0 ppm. HRMS (ESI) $[M+H]^+$ calcd. for $C_{21}H_{19}NO_2$ 318.1489, found 318.1484.

Synthesis of 2,5-dioxopyrrolidin-1-yl 4-(dibenzylamino)benzoate S6

Gly-Phe-$NH_2$ 1 (4.42 mg, 0.02 mmol) was taken in a clean and dry 5 ml vial charged with magnetic stir bar containing 200 μl solution of acetonitrile. To this 2,5-dioxopyrrolidin-1-yl-4-(dibenzylamino)benzoate S6 (16.56 mg, 0.04 mmol) and triethyl amine (2.76 μl, 0.02 mmol) were added and resulting reaction mixture was allowed to stir at room temperature for 2 h. Reaction was followed by thin layer chromatography. Reaction mixture was concentrated under reduced pressure, the resulting residue was purified via flash column chromatography on silica (DCM/MeOH, 97:2, $R_f$ 0.1) as the eluent, thereby affording the title compound (S)—N-(2-((1-amino-1-oxo-3-phenylpropan-2-yl)amino)-2-oxoethyl)-4-(dibenzylamino)benzamide 2c (3.8 mg, 35% yield) as white solid. $^1$H NMR (500 MHz, $CDCl_3$) δ 7.57 (d, J=8.5 Hz, 2H), 7.34 (m, 4H), 7.29 (d, J=7.1 Hz, 2H), 7.20 (m, 4H), 7.17 (m, 4H), 7.13 (m, 11H), 6.72 (d, J=8.5 Hz, 2H), 4.72 (s, 4H), 4.67 (dd, J=14.4, 7.1 Hz, 1H), 3.98 (m, 2H), 3.11 (m, 2H) ppm. $^{13}$C NMR (126 MHz, $CDCl_3$) δ 173.0, 169.6, 168.1, 151.9, 137.4, 136.4, 129.2, 129.0, 128.9, 128.7, 127.3, 127.0, 126.4, 120.4, 111.6, 54.1, 44.1, 37.5, 29.7 ppm. HRMS (ESI) $[M+Na]^+$ calcd. for $C_{32}H_{32}N_4O_3$ 543.2367, found 543.2371.

6.5 Procedure for Synthesis of Sensitivity Booster 2,5-dioxopyrrolidin-1-yl 3-(benzyl(pyridin-2-ylmethyl)amino)propanoate (S54) and (S)—N-(2-((1-amino-1-oxo-3-phenylpropan-2-yl)amino)-2-oxoethyl)-3-(benzyl(pyridin-2-ylmethyl)amino)propanamide 2d

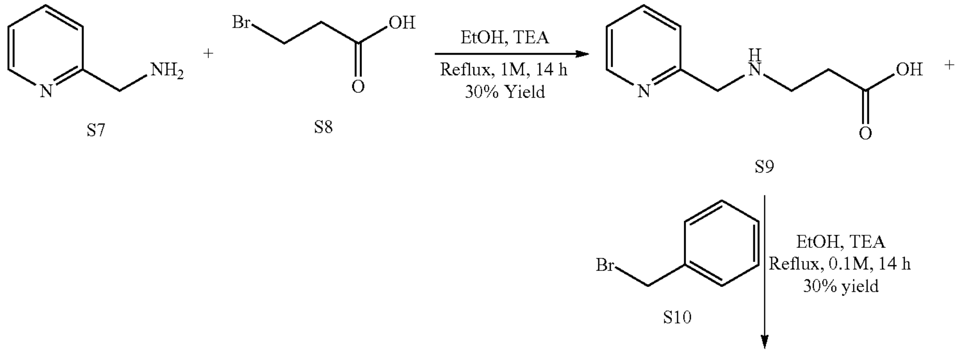

S7 S8 S9 S10

-continued

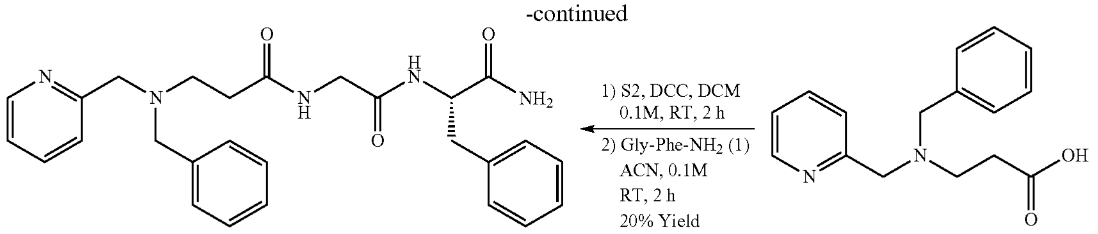

2d S11

3-((pyridin-2-ylmethyl)amino)propanoic acid S9[3]

2-Aminomethylpyridine S7 (510 μl, 5 mmol) and triethyl amine (690 μl, 5 mmol) were taken in a clean and dry 25 ml round bottom flask charged with magnetic stir bar containing the 5 ml solution of EtOH. 3-bromo propionic acid S8 (760 mg, 5 mmol) was added and refluxed at 80° C. for 24 h. On cooling, the resulting precipitate was filtered off, washed with small portions of acetonitrile, and dried in reduced pressure to afford 3-((pyridin-2-ylmethyl)amino) propanoic acid S9 (360 mg, 40% yield) as colourless needles. $^{1}H$ NMR (500 MHz, $D_2O$): δ 8.59 (d, J=4.6 Hz, 1H), 7.91 (m, 1H), 7.52 (d, J=7.8 Hz, 1H), 7.47 (m, 1H), 4.38 (s, 2H), 3.30 (t, J=6.6 Hz, 2H), 2.60 (t, J=6.6 Hz, 2H) ppm. $^{13}C$ NMR (126 MHz, $D_2O$): δ 180.5, 152.7, 152.0, 141.0, 127.0, 126.6, 53.5, 46.9, 34.8 ppm. MS (ESI) $[M+H]^+$ calcd. for $C_9H_{12}N_2O_2$ 181.2, found 181.2.

3-(benzyl(2-(pyridin-2-yl)ethyl)amino)propanoic acid S11[3]

3-((pyridin-2-ylmethyl)amino)propanoic acid S9 (180 mg, 1 mmol) and triethyl amine (130 μl, 1 mmol) were taken in a clean and dry 25 ml vial charged with magnetic stir bar containing 10 ml solution of EtOH. Benzyl bromide S10 (118 μl, 1 mmol) was added and refluxed at 80° C. for 24 h. On cooling, the resulting precipitate was filtered off, resulting residue was purified via flash column chromatography on silica using (DCM/MeOH, 97:5, $R_f$ 0.1) as the eluent, thereby affording the title product 3-(benzyl(pyridin-2-ylmethyl)amino)propanoic acid S11 (108 mg, 40% yield) as white solid. $^{1}H$ NMR (500 MHz, $CDCl_3$): δ 8.59 (m, 1H), 7.68 (m, 1H), 7.36-7.27 (m, 5H), 7.24-7.22 (m, 2H), 3.85 (s, 2H), 3.80 (s, 2H), 2.96 (t, J=6.2 Hz, 2H), 2.60 (t, J=6.2 Hz, 2H) ppm. $^{13}C$ NMR (126 MHz, $CDCl_3$) δ 173.5, 156.4, 149.2, 137.1, 135.7, 129.5, 128.8, 128.1, 123.6, 122.8, 58.0 (unresolved doublet), 49.2, 31.1 ppm. LRMS (ESI) $[M+H]^+$ calcd. for $C_{15}H_{17}N_3O_2$ 271.3, found 271.4.

(S)—N-(2-((1-amino-1-oxo-3-phenylpropan-2-yl) amino)-2-oxoethyl)-3-(benzyl(pyridin-2-ylmethyl) amino)propanamide 2d N-Hydroxysuccinimide S2 (23.0 mg, 0.2 mmol) and N-ethyl-N'-(3-dimethylaminopropyl) carbodiimide hydrochloride (38.3 mg, 0.2 mmol) were taken in a clean and dry 5 ml vial charged with magnetic stir bar containing 1 ml solution of dichloromethane. 3-(benzyl(pyridin-2-ylmethyl) amino)propanoic acid S11 (27 mg, 0.1 mmol) was added and allowed to stir at room temperature for 2 h to give 554. The reaction was followed by thin layer chromatography. The reaction mixture was diluted with dichloromethane (9 ml) and extracted (2×8 ml) with water. The organic layer was dried over $Na_2SO_4$, concentrated under reduced pressure, and the remaining crude reagent was transferred into 5 ml vial charged with magnetic stir bar. After addition of acetonitrile (0.2 ml), Gly-Phe-$NH_2$ 1 (4.42 mg, 0.02 mmol) and triethylamine (2.76 μl, 0.02 mmol) were added through micropipette. The reaction mixture was stirred at room temperature for 2 h and followed by ESI-MS. The reaction was diluted to 500 μl with acetonitrile and subjected to prep-HPLC for the purification to isolate (S)—N-(2-((1-amino-1-oxo-3-phenylpropan-2-yl)amino)-2-oxoethyl)-3-(benzyl(pyridin-2-ylmethyl)amino)propanamide 2d (2.82 mg, 30% yield). $^{1}H$ NMR (500 MHz, $CDCl_3$) δ 8.55 (m, 1H), 7.65 (m, 1H), 7.33-7.25 (m, 4H), 7.24-7.17 (m, 6H), 7.12-7.09 (m, 2H), 4.70 (m, 1H), 3.88-3.78 (m, 2H), 3.73 (m, 2H), 3.64 (m, 2H), 3.17 (dd, J=14.1, 6.7 Hz, 1H), 3.04 (dd, J=14.1, 5.9 Hz, 1H), 2.75 (m, 2H), 2.49-2.27 (m, 2H) ppm. $^{13}C$ NMR (126 MHz, $CDCl_3$) δ 173.7, 173.7, 169.8, 157.7, 149.3, 137.1, 136.9, 136.4, 129.2, 128.6, 128.6, 127.7, 126.9, 123.7, 122.8, 122.6, 58.8, 58.1, 53.7, 49.2, 43.9, 36.9, 32.5 ppm. HRMS (ESI) $[M+H]^+$ calcd. for $C_{27}H_{31}N_5O_3$ 474.2500, found 474.2526.

6.6 Procedure for Synthesis of Sensitivity Booster 2,5-dioxopyrrolidin-1-yl 3-(bis(pyridin-2-ylmethyl) amino)propanoate (S55) and (S)—N-(2-((1-amino-1-oxo-3-phenylpropan-2-yl)amino)-2-oxoethyl)-3-(bis(pyridin-2-ylmethyl)amino)propanamide 2e

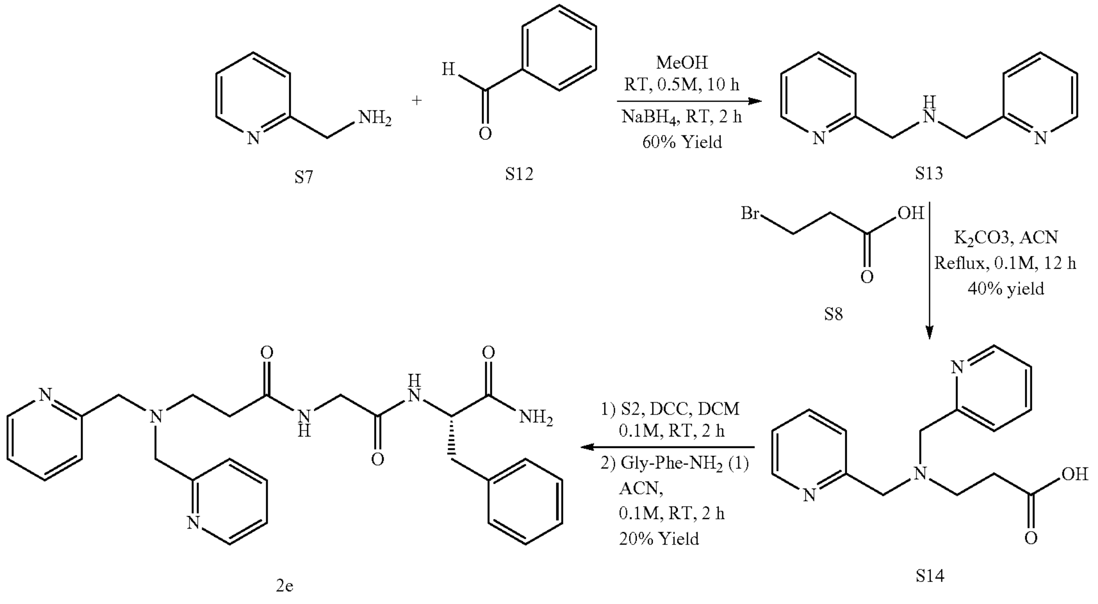

S7 S12 S13 S8 S14 2e

Synthesis of di-(2-picolyl)amine S13[4]

To a suspension of 2-pyridinecarboxaldehyde S12 (0.951 ml, 10 mmol) in ethanol (2 ml), a solution of 2-(aminomethyl)-pyridine S7 (1.03 ml, 10 mmol) in ethanol (18 ml) was added dropwise at 0° C. After 4 h, sodium borohydride (726 mg, 19.2 mmol) was added in small portions while maintaining the temperature at 0° C. The reaction was stirred for 12 h at room temperature. Next, aqueous hydrochloric acid (5 M, 24 ml) was added dropwise and it was stirred for another 1 h. A 2 M aqueous solution of sodium hydroxide was then added until a pH of 11 was reached. The mixture was extracted with methylene chloride (6×100 ml), dried over sodium sulfate, and then filtered. Removal of volatiles afforded an analytically pure di-(2-picolyl)amine S13 (1.71 g 89% yield) as a brown oil. $^{1}H$ NMR (500 MHz, $CDCl_3$): δ 8.56 (d, J=4.7 Hz, 2H), 7.64 (m, 2H), 7.36 (d, J=7.7 Hz, 2H), 7.16 (dd, J=6.9, 5.4 Hz, 2H), 3.99 (s, 4H) ppm. $^{13}C$ NMR (126 MHz, $CDCl_3$): δ 159.6, 149.3, 136.5, 122.3, 122.0, 54.7 ppm. LRMS (ESI) $[M+H]^+$ calcd. for $C_{12}H_{13}N_3$ 200.1, found 200.2.

Synthesis of 3-(bis(pyridin-2-ylmethyl)amino)propanoic acid S14[5]

Di-(2-picolyl)amine S13 (190 mg, 1 mmol) and triethyl amine (138 μl, 1 mmol) were taken in a clean and dry 25 ml vial charged with magnetic stir bar containing 10 ml solution of EtOH. Next, 3-bromopropionic acid S8 (152 mg, 1 mmol) was added and the reaction mixture was refluxed at 80° C. for 24 h. The cooling to room temperature results in the formation of precipitate. It is filtered, washed with small portions of acetonitrile, and dried in vacuo to afford 3-(bis(pyridin-2-ylmethyl)amino)propanoic acid S14 (108 mg, 40% yield) as colourless needles. 1H NMR (500 MHz, $CDCl_3$): δ 8.53 (d, J=4.3 Hz, 2H), 7.62 (m, 2H), 7.34 (m, 2H), 7.17 (m, 2H), 3.92 (s, 4H), 3.00 (t, J=6.4 Hz, 2H), 2.60 (t, J=6.4 Hz, 2H) ppm. $^{13}C$ NMR (126 MHz, $CDCl_3$): 174.2, 157.3, 148.9, 137.1, 123.6, 122.6, 59.2, 49.9, 32.4 ppm. LRMS (ESI) $[M+H]^+$ calcd. for $C_{15}H_{17}N_3O_2$ 272.1, found 272.1.

(S)—N-(2-((1-amino-1-oxo-3-phenylpropan-2-yl) amino)-2-oxoethyl)-3-(bis(pyridin-2-ylmethyl) amino)propanamide 2e N-Hydroxysuccinimide S2 (23.0 mg, 0.2 mmol) and N-ethyl-N'-(3-dimethylaminopropyl) carbodiimide hydrochloride (38.3 mg, 0.2 mmol) were taken in a clean and dry 5 ml vial charged with magnetic stir bar containing 1 ml solution of dichloromethane. Next, 3-(bis(pyridin-2-ylmethyl)amino)propanoic acid S14 (27.4 mg, 0.1 mmol) was added and allowed to stir at room temperature for 2 h to give sensitivity booster S55. The progress of reaction was followed by thin layer chromatography. The reaction mixture was diluted with dichloromethane (9 ml) and extracted with water (2×8 ml). The organic layer was dried over $Na_2SO_4$, concentrated under reduced pressure, and the remaining crude reagent was transferred into 5 ml vial charged with magnetic stir bar. It was diluted with acetonitrile (0.2 ml) and Gly-Phe-$NH_2$ 1 (4.42 mg, 0.02 mmol) and triethyl amine (2.76 μl, 0.02 mmol) were added through micropipette. The reaction mixture was allowed to stir at room temperature for 2 h. Subsequently, it was diluted to 500 μl with acetonitrile and subjected to prep-HPLC to isolate (S)—N-(2-((1-amino-1-oxo-3-phenylpropan-2-yl)amino)-2-oxoethyl)-3-(bis(pyridin-2-ylmethyl)amino)propanamide 2e (2.82 mg, 30% yield). $^{1}H$ NMR (500 MHz, $CDCl_3$) δ 8.50 (d, J=4.2 Hz, 2H), 7.62 (m, 2H), 7.22 (m, 2H), 7.20-7.15 (m, 5H), 7.11 (m, 2H), 4.70 (m, 1H), 3.88 (m, 2H), 3.80 (m, 4H), 3.15 (dd, J=14.1, 7.2 Hz, 1H), 3.07 (dd, J=14.3, 5.7 Hz, 1H), 2.79 (t, J=5.8 Hz, 2H), 2.44-2.25 (m, 2H) ppm. $^{13}C$ NMR (126

MHz, $CDCl_3$) δ 173.7, 170.2, 170.1, 157.9, 149.5, 136.8, 136.6, 129.2, 128.6, 126.9, 123.4, 122.6, 59.6, 53.7, 49.7, 44.2, 36.7, 32.8 ppm. MS (ESI) $[M+H]^+$ calcd. for $C_{26}H_{30}N_6O_3$ 475.2452, found 475.2478.

6.7 Procedure for Synthesis of Sensitivity Booster 2,5-dioxopyrrolidin-1-yl 4-(4-((dibenzylamino) methyl)-1H-1,2,3-triazol-1-yl)benzoate (S56) and (S)—N-(2-((1-amino-1-oxo-3-phenylpropan-2-yl) amino)-2-oxoethyl)-4-(4-((dibenzylamino)methyl)-1H-1,2,3-triazol-1-yl)benzamide 2f

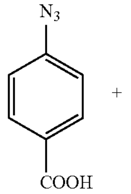

S16

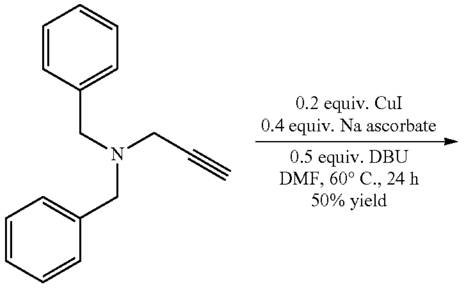

S18

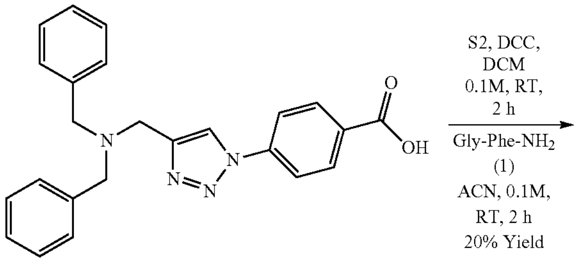

S19

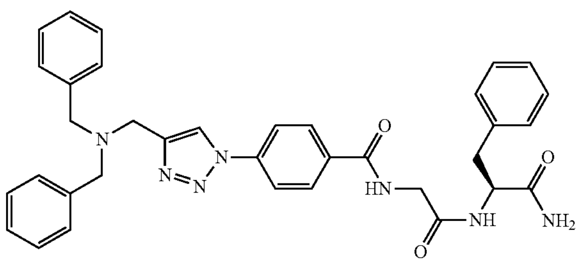

2f (a) Synthesis of 4-azidobenzoic acid S16

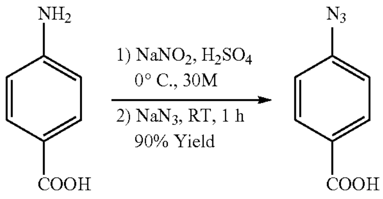

S15 S16

(b) Synthesis of N, N-Dibenzylpropargylamine S18

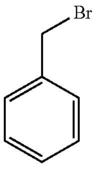

+

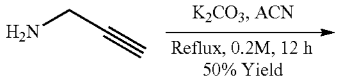

S10 S17

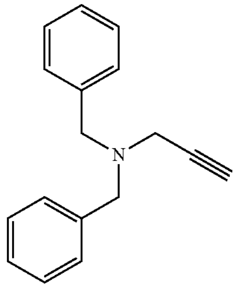

S18

Synthesis of 4-azidobenzoic acid S16[6]

To an ice-cold suspension of 4-aminobenzoic acid S15 (137 mg, 1.0 mmol) in 6 N $H_2SO_4$ (2 ml), an aqueous solution of sodium nitrite (83 mg, 1.2 mmol) was added dropwise over 10 min. The resulting mixture was stirred at 0° C. for additional 30 min. An aqueous solution of sodium azide (98 mg, 1.5 mmol) was added dropwise to the above mixture. The reaction was then carried out at room temperature for 1 h. The reaction mixture was extracted with EtOAc (3x30 ml). The combined EtOAc phase was washed with water, brine and dried over $Na_2SO_4$. After removal of $Na_2SO_4$ via filtration, the filtrate was concentrated to dryness to afford the desired azidobenzoic acid S16 (163 mg, 98% yield) as a white solid. $^1H$ NMR (500 MHz, $CDCl_3$): δ 8.11 (d, J=8.4 Hz, 2H), 7.11 (d, J=8.4 Hz, 2H) ppm. $^{13}C$ NMR (126 MHz, $CDCl_3$): δ 170.8, 145.8, 132.1, 125.6, 119.0 ppm.

Synthesis of N,N-Dibenzylpropargylamine S18

A mixture of benzyl bromide S10 (0.69 ml, 0.58 mmol), propargylamine 817 (0.2 ml, 3 mmol), and potassium carbonate (1.232 g, 1.2 mol) were vigorously stirred in acetonitrile (15 ml) in a 100 ml round bottom flask charged with a magnetic stir bar. The reaction was refluxed for 4 h at 78° C.

and the solvent was removed under the reduced pressure. It was further re-diluted with 20 ml water and extracted with dichloromethane (3×15 ml). The combined organic extracts were dried over $Na_2SO_4$ and concentrated. The resulting residue was purified via flash column chromatography on silica (hexane/EtOAC 97:3, $R_f$0.25), thereby affording N,N-dibenzylpropargylamine S18 (0.502 g, 71% yield) as yellow liquid. $^1$H NMR (500 MHz, $CDCl_3$) δ 7.39 (m, 4H), 7.34-7.28 (m, 4H), 7.24 (m, 2H), 3.68 (s, 4H), 3.25 (d, J=2.4 Hz, 2H), 2.26 (t, J=2.4 Hz, 1H) ppm. $^{13}$C NMR (126 MHz, $CDCl_3$) δ 138.9, 129.1, 128.4, 127.2, 78.6, 73.4, 57.5, 41.2 ppm. HRMS (ESI) $[M+H]^+$ calcd. for $C_{17}H_{17}N$ 236.1434, found 236.1457.

Synthesis of 4-(4-((dibenzylamino)methyl)-1H-1,2,3-triazol-1-yl)benzoic acid S197

A mixture of CuI (1.9 mg, 0.01 mmol, 0.01 equiv.), DIPEA (2.6 mg, 0.02 mmol, 0.02 equiv.), and AcOH (1.2 mg, 0.02 mmol, 0.02 equiv.) in DMF (5 ml) was taken in a clean and dry 5 ml vial charged with magnetic stir bar. Next, N,N-dibenzylpropargyl amine S18 (235 mg, 1 mmol) and benzyl azide S16 (175 mg, 1.05 mmol) were added and the reaction mixture was allowed to stir at room temperature until the alkyne disappeared (~24 h). The reaction mixture was purified by a short chromatography column (DCM/MeOH, 95:5, Rr 0.2) to give 4-(4-((dibenzylamino)methyl)-1H-1,2,3-triazol-1-yl)benzoic acid S19 (199 mg, 50% yield) as a white solid. $^1$H NMR (500 MHz, $CDCl_3$) δ 8.27 (d, J=8.8 Hz, 2H), 8.00 (s, 1H), 7.86 (d, J=8.8 Hz, 2H), 7.45 (m, 4H), 7.35 (m, 4H), 7.30-7.25 (m, 2H), 3.95 (s, 2H), 3.78 (s, 4H) ppm. $^{13}$C NMR ($CDCl_3$, 126 MHz): δ 169.9, 146.2, 140.4, 138.1, 138.0, 131.9, 129.1, 128.5, 127.4, 120.9, 119.9, 57.7, 47.9 ppm. HRMS (ESI) $[M+H]^+$ calcd. for $C_{24}H_{22}N_4O_2$ 399.1816, found 399.1829.

Synthesis of (S)—N-(2-((1-amino-1-oxo-3-phenylpropan-2-yl)amino)-2-oxoethyl)-4-(4((dibenzylamino)methyl)-1H-1,2,3-triazol-1-yl)benzamide 2f N-Hydroxysuccinimide S2 (23.0 mg, 0.2 mmol) and N-ethyl-N'-(3-dimethylaminopropyl) carbodiimide hydrochloride (38.3 mg, 0.2 mmol) were taken in a clean and dry 5 ml vial charged with magnetic stir bar containing dichloromethane (1 ml). The 4-(4-((dibenzylamino)methyl)-1H-1,2,3-triazol-1-yl)benzoic acid S19 (20.0 mg, 0.05 mmol) was added and the reaction mixture was stirred at room temperature for 2 h to prepare sensitivity booster S56. The reaction was followed by thin layer chromatography. Next, it was diluted with dichloromethane (9 ml) and extracted with water (2×8 ml). The organic layer was dried over $Na_2SO_4$, concentrated under reduced pressure, and crude reagent was transferred into 5 ml vial charged containing acetonitrile (0.2 ml) and magnetic stir bar. Next, Gly-Phe-$NH_2$ 1 (4.42 mg, 0.02 mmol) and triethyl amine (2.76 μl, 0.02 mmol) were added through micropipette and the reaction mixture was stirred at room temperature for 2 h. It was further diluted to 500 μl by addition of acetonitrile and subjected to prep-HPLC to isolate pure N-(2-((1-amino-1-oxo-3-phenylpropan-2-yl)amino)-2-oxoethyl)-4-(4((dibenzylamino)methyl)-1H-1,2,3-triazol-1-yl)benzamide 2f (3.6 mg, 30% yield). $^1$H NMR (500 MHz, $CDCl_3$) δ 7.92 (d, J=7.9 Hz, 2H), 7.88 (s, 1H), 7.75 (d, J=7.9 Hz, 2H), 7.41 (m, 4H), 7.32 (m, 4H), 7.24 (m, 2H), 7.22-7.11 (m, 5H), 4.71 (dd, J=16.0, 10.2 Hz, 1H), 4.08 (m, 2H), 3.83 (s, 2H), 3.67 (s, 4H), 3.08 (m, 2H) ppm. $^{13}$C NMR (126 MHz, $CDCl_3$) δ 173.4, 169.3, 166.7, 139.4, 138.9 (two peaks), 136.3, 133.1, 129.8, 129.2, 129.0, 128.8, 128.7, 128.4, 127.1, 120.5, 120.1, 57.9, 54.5, 48.2, 43.8, 38.0 ppm. HRMS (ESI) $[M+H]^+$ calcd. for $C_{35}H_{35}N_7O_3$ 602.2874, found 602.2884.

6.8 Synthesis of (S)-4-((6-(1H-imidazol-1-yl)hexyl)oxy)-N-(2-((1-amino-1-oxo-3-phenylpropan-2-yl)amino)-2-oxoethyl)benzamide 2g

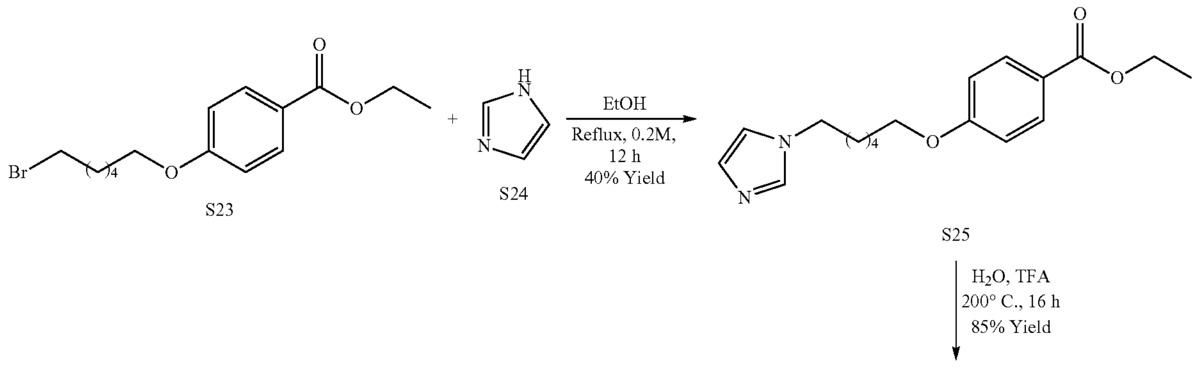

S23 S24 S25

-continued

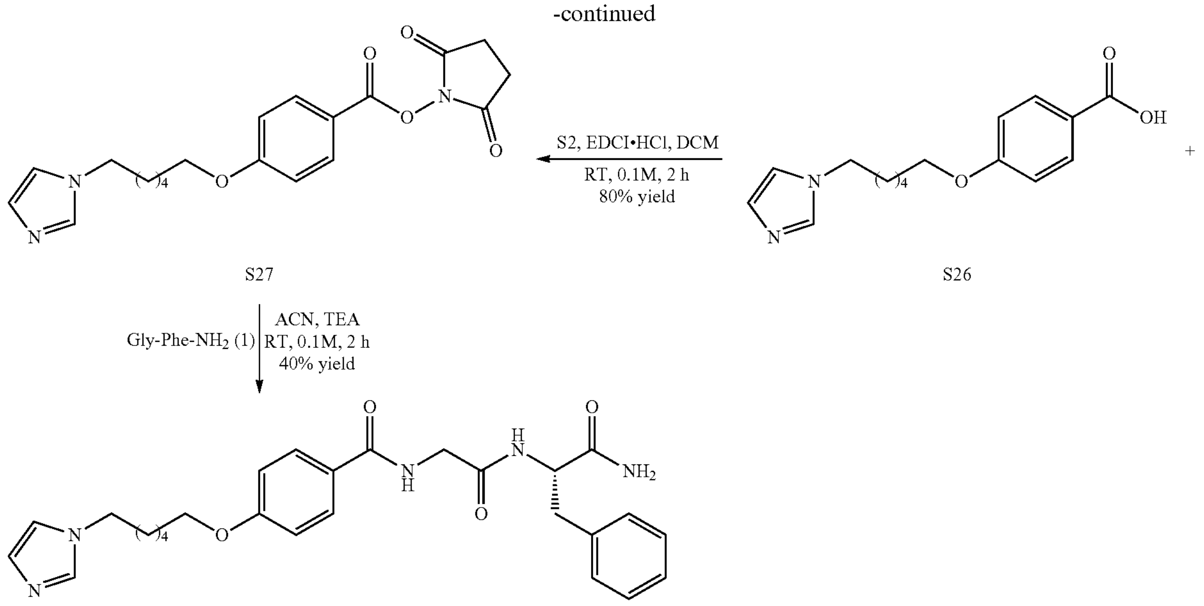

S27 S26 2g a) Synthesis of ethyl 4-hydroxybenzoate S23

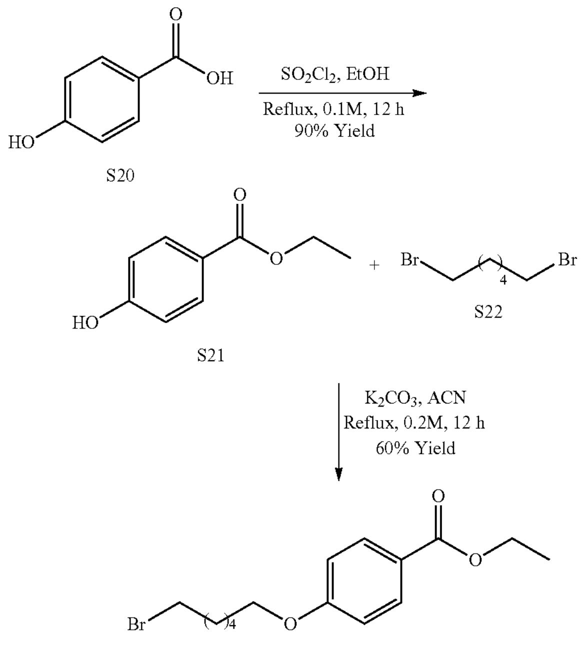

S20 S21 S22 S23

Synthesis of ethyl 4-hydroxybenzoate S21

4-Hydroxybenzoic acid S20 (138 mg, 1 mmol) was taken in a 25 ml round bottom flask containing EtOH (10 ml) and Teflon-coated magnetic stir bar. The flask was placed in an ice-water bath followed by slow addition of thionyl chloride (0.29 ml, 4 mmol). After the addition, flask was moved from ice-water bath to oil-bath and sealed by condenser having $CaCl_2$) guard tube. The reaction mixture was refluxed for 6 h before bringing it back to the room temperature. The reaction mixture was concentrated under reduced pressure to give the product ethyl 4-hydroxybenzoate S21 (157 mg, 95% yield) as white precipitate. $^1H$ NMR (500 MHz, $CDCl_3$) δ 7.95 (d, J=8.6 Hz, 2H), 6.90 (m, 2H), 4.36 (q, J=7.0 Hz, 2H), 1.38 (t, J=7.1 Hz, 3H) ppm. $^{13}C$ NMR (126 MHz, $CDCl_3$) δ 166.8, 160.0, 131.9, 122.9, 115.2, 60.9, 14.4 ppm. HRMS (ESI) $[M+Na]^+$ calcd. for $C_9H_{10}O_3$ 189.0522, found 189.0536.

Synthesis of ethyl 4-((6-bromohexyl)oxy)benzoate S23

4-Hydroxyethylbenzoate S21 (165 mg, 1 mmol) and potassium carbonate (276 mg, 1 mmol) were taken in a 25 ml round bottom flask with Teflon-coated magnetic stir bar and acetonitrile (5 ml). Next, 1,6-dibromohexane S22 (0.307 ml, 2 mmol) was added and flask was sealed with condenser. The reaction mixture was refluxed for 16 h, cooled to room temperature, and the white solid (waste of potassium carbonate) was filtered through celite. The filtrate was dried under reduced pressure to get yellow oil that was purified flash column chromatography. The desired product was eluted using (n-hexane/ethyl acetate, 98:2, Rf=0.1) to obtain ethyl 4-(6-bromohexyloxy)benzoate S23 (171 mg, 60% yield) as a pale-yellow oil. $^1H$ NMR (500 MHz, $CDCl_3$) δ 7.99 (d, J=8.9 Hz, 2H), 6.90 (d, J=8.9 Hz, 2H), 4.34 (q, J=7.1 Hz, 2H), 4.01 (t, J=6.4 Hz, 2H), 3.43 (t, J=6.8 Hz, 2H), 1.94-1.87 (m, 2H), 1.87-1.77 (m, 2H), 1.55-1.47 (m, 4H), 1.38 (t, J=7.1 Hz, 3H) ppm. $^{13}C$ NMR (126 MHz, $CDCl_3$): δ 166.4, 162.8, 131.5, 122.8, 114.0, 67.9, 60.6, 33.7, 32.6, 29.0, 27.9, 25.3, 14.4 ppm. HRMS (ESI) $[M+H]^+$ calcd. for $C_{15}H_{21}BrO_3$ 329.0747, found 329.0712.

Synthesis of ethyl 4-((6-(1H-imidazol-1-yl)hexyl)oxy)benzoate S25

Imidazole S24 (204 mg, 3 mmol) was taken in a 25 ml round bottom flask charged with Teflon-coated magnetic stir bar containing 5 ml solution of EtOH. Ethyl 4-(6-bromohexyloxy)benzoate S23 (329 mg, 1 mmol) was added and allowed to refluxed for 12 h. The resultant mixture was concentrated under reduced pressure and purified by a short chromatograph column [DCM/MeOH, 95:5, $R_f$0.5] to afford of ethyl 4-((6-(1H-imidazol-1-yl)hexyl)oxy)benzoate S25 (158.5 mg, 50% yield) as a viscous liquid. $^1$H NMR (500 MHz, $CDCl_3$) δ 7.98 (d, J=8.9 Hz, 2H)), 7.47 (s, 1H), 7.06 (m, 1H), 6.90 (m, 1H), 6.88 (d, J=8.9 Hz, 2H), 4.34 (q, J=7.1 Hz, 2H), 3.99 (t, J=6.3 Hz, 2H), 3.95 (t, J=7.1 Hz, 2H), 1.86-1.75 (m, 4H), 1.55-1.47 (m, 2H), 1.41-1.34 (m, 5H) ppm. $^{13}$C NMR ($CDCl_3$, 126 MHz) δ 166.4, 162.7, 137.1, 131.5, 129.5, 122.8, 118.7, 114.0, 67.8, 60.6, 46.9, 31.0, 28.9, 26.3, 25.6, 14.4 ppm. HRMS (ESI) $[M+H]^+$ calcd. for $C_{18}H_{24}N_2O_3$ 317.1860, found 317.1860.

4-((6-(1H-imidazol-1-yl)hexyl)oxy)benzoic acid S26 ethyl 4-((6-(1H-imidazol-1-yl)hexyl)oxy)benzoate S25 (316 mg, 1 mmol) was taken in a 5 ml round bottom flask charged with Teflon-coated magnetic stir bar containing 2 ml of water. Subsequently, TFA (0.918 ml, 12 mmol) was added slowly and the flask was sealed with condenser. The reaction mixture was refluxed (bath temperature of 200° C.) for 24 h. Next, it was cooled to room temperature and the solvent was concentrated under reduced pressure to give a yellow oil. To this, diethyl ether (3×3 ml) was mixed and stirred for overall 30 min at room temperature. It crashes the product as a white precipitate that is isolated and dried under reduced pressure to obtain 4-((6-(1H-imidazol-1-yl)hexyl)oxy)benzoic acid S26 (241 mg, 84% yield). $^1$H NMR (500 MHz, $CD_3OD$) δ 8.96 (s, 1H), 7.95 (d, J=8.9 Hz, 2H), 7.72-7.63 (m, 1H), 7.62-7.51 (m, 1H), 6.95 (d, J=8.9 Hz, 2H), 4.27 (t, J=7.3 Hz, 2H), 4.04 (t, J=6.3 Hz, 2H), 1.94 (m, 2H), 1.81 (m, 2H), 1.56 (m, 2H), 1.42 (m, 2H) ppm. $^{13}$C NMR (126 MHz, $CD_3OD$): δ 168.4, 163.0, 134.9, 131.4, 122.5, 121.8, 119.8, 113.7, 67.6, 49.1, 29.7, 28.5, 25.6, 25.1 ppm. HRMS (ESI) $[M+H]^+$ calcd. for $C_{16}H_{20}N_2O_3$ 289.1547, found 289.1543.

2,5-dioxopyrrolidin-1-yl-4-((6-(1H-imidazol-1-yl) hexyl)oxy)benzoate S27

N-Hydroxysuccinimide S2 (23.0 mg, 0.2 mmol) and N-ethyl-N'-(3-dimethylaminopropyl) carbodiimide hydrochloride (38.3 mg, 0.2 mmol) were taken in a clean and dry 5 ml vial containing magnetic stir bar and dichloromethane (1 ml). Next, 4-((6-(1H-Imidazol-1-yl)hexyl)oxy)benzoic acid S26 (0.028 g, 0.1 mmol) was added and reaction mixture was stirred at room temperature for 2 h. The progress of reaction was followed by thin layer chromatography. The reaction mixture was diluted dichloromethane (9 ml) and extracted by water (2×8 ml). The organic layer was dried over $Na_2SO_4$ and concentrated under the reduced pressure. The resulting residue was triturated with ether and pentane (2 ml each) to yield 2,5-dioxopyrrolidin-1-yl 4-((6-(1H-imidazol-1-yl)hexyl)oxy)benzoate S27 (0.023 g, yield 60%) as white solid. $^1$H NMR (500 MHz, $CDCl_3$) δ 8.09 (d, J=8.9 Hz, 2H), 7.53 (s, 1H), 7.07 (m, 1H), 6.94 (d, J=9.0 Hz, 2H), 6.92 (m, 1H), 4.02 (t, J=6.3 Hz, 2H), 3.96 (t, J=7.1 Hz, 2H), 2.89 (s, 4H), 1.87-1.76 (m, 4H), 1.51 (m, 2H), 1.37 (m, 2H) ppm. $^{13}$C NMR (126 MHz, $CDCl_3$): δ 169.5, 164.4, 161.5, 137.1, 132.9, 129.2, 118.9, 117.0, 114.62, 68.2, 47.0, 31.0, 28.8, 26.3, 25.7, 25.5 ppm. HRMS (ESI) $[M+H]^+$ calcd. for $C_{20}H_{23}N_3O_5$ 386.1710, found 386.1700.

(S)-4-((6-(1H-imidazol-1-yl)hexyl)oxy)-N-(2-((1-amino-1-oxo-3-phenylpropan-2-yl)amino)-2-oxoethyl)benzamide 2g Gly-Phe-$NH_2$ 1 (4.42 mg, 0.02 mmol) was taken in a clean and dry 5 ml vial charged with magnetic stir bar containing 200 μl solution of acetonitrile. To this, 2,5-dioxopyrrolidin-1-yl 4-((6-(1H-imidazol-1-yl)hexyl)oxy) benzoate S27 (15.4 mg, 0.02 mmol) and triethyl amine (2.76 μl, 0.01 mmol) were added and the resulting reaction mixture was stirred at room temperature for 2 h. The reaction was followed by thin layer chromatography and concentrated under reduced pressure. The resulting residue was purified by flash column chromatography on silica (DCM/MeOH, 95:5, $R_f$ 0.1), affording the title compound (S)-4-((6-(1H-imidazol-1-yl)hexyl)oxy)-N-(2-((1-amino-1-oxo-3-phenylpropan-2-yl)amino)-2-oxoethyl)benzamide 2g (1.9 mg, 35% yield) as yellowish white solid. $^1$H NMR (500 MHz, $CDCl_3$) δ 7.73 (d, J=8.7 Hz, 2H), 7.49 (s, 1H), 7.23-7.16 (m, 5H), 7.05 (m, 1H), 6.90 (m, 1H), 6.87 (d, J=8.7 Hz, 2H), 4.69 (dd, J=14.4, 6.9 Hz, 1H), 4.03 (m, 2H), 3.98 (t, J=6.3 Hz, 2H), 3.95 (t, J=7.1 Hz, 2H), 3.10 (m, 2H), 1.82-1.75 (m, 4H), 1.50 (m, 2H), 1.36 (m, 2H) ppm. $^{13}$C NMR (126 MHz, $CDCl_3$) δ 173.0, 169.4, 167.7, 162.0, 137.0, 136.4, 129.3, 129.2, 129.1, 128.7, 127.1, 125.4, 118.8, 114.3, 67.8, 54.2, 47.0, 43.9, 37.7, 30.9, 28.8, 26.2, 25.5 ppm. HRMS (ESI) $[M+H]^+$ calcd. for $C_{27}H_{33}N_5O_4$ 492.2605, found 492.2622.

6.9 Procedure for Synthesis of Sensitivity Booster 1-(6-(4-(((2,5-dioxopyrrolidin-1-yl)oxy)carbonyl) phenoxy)hexyl)pyridin-1-ium bromide (S57) and (S)-1-(6-(4-((2-((1-amino-1-oxo-3-phenylpropan-2-yl)amino)-2-oxoethyl)carbamoyl)phenoxy)hexyl) pyridin-1-ium bromide 2h

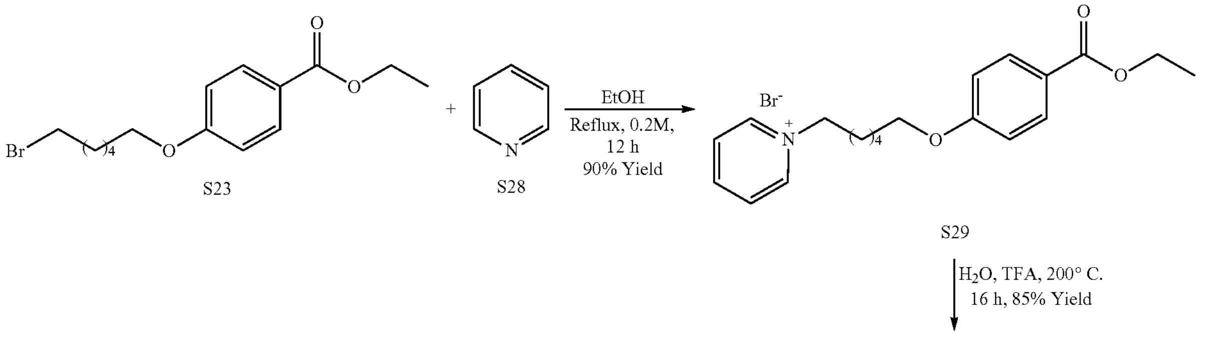

S23 S28 S29

-continued

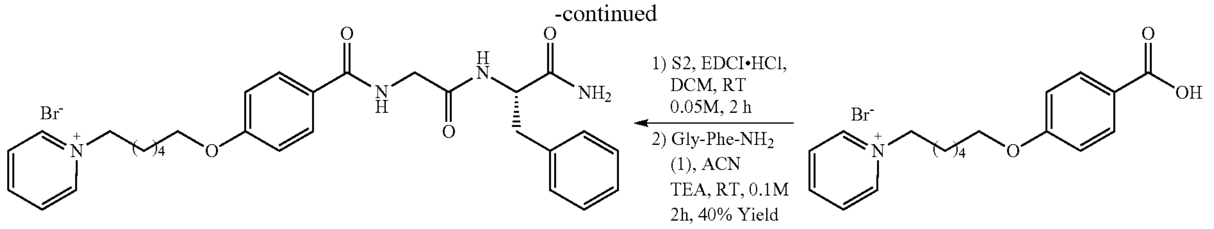

2h S30

Synthesis of 1-(6-(4-(ethoxycarbonyl)phenoxy) hexyl)pyridin-1-ium bromide S29

Pyridine S28 (0.161 ml, 2 mmol) was taken in a 10 ml round bottom flask charged with Teflon-coated magnetic stir bar containing 5 ml of EtOH. Next, ethyl 4-((6-bromohexyl) oxy)benzoate S23 (329 mg, 1 mmol) was added and flask was sealed with a condenser. The reaction mixture was refluxed for 12 h and concentrated under reduced pressure. The resulting residue was triturated with ether (5 ml) to give the title compound 1-(6-(4-(ethoxycarbonyl)phenoxy)hexyl) pyridin-1-ium bromide S29 as a white solid (325 mg, 80% yield). $^{1}$H NMR (500 MHz, $CDCl_3$) δ 9.57 (d, J=5.6 Hz, 2H), 8.49 (t, J=7.8 Hz, 1H), 8.11 (t, J=6.9 Hz, 1H), 7.96 (d, J=8.7 Hz, 2H), 6.88 (d, J=8.8 Hz, 2H), 5.08 (t, J=7.3 Hz, 2H), 4.34 (q, J=7.1 Hz, 2H), 3.99 (t, J=6.2 Hz, 2H), 2.10 (m, 2H), 1.79 (m, 2H), 1.61-1.46 (m, 4H), 1.37 (t, J=7.1 Hz, 3H) ppm. $^{13}$C NMR (126 MHz, $MeOD_4$) δ 162.5, 158.7, 141.3, 141.1, 127.6, 124.4, 118.8, 110.1, 63.8, 57.9, 56.7, 28.0, 24.8, 21.7, 21.5, 10.5 ppm. HRMS (ESI) $[M]^+$ calcd. for $C_{20}H_{26}NO_3$ 328.1907, found 328.1888.

Synthesis of 1-(6-(4-carboxyphenoxy)hexyl)pyridin-1-ium bromide S30

1-(6-(4-(Ethoxycarbonyl)phenoxy)hexyl)pyridin-1-ium bromide S29 (407 mg, 1 mmol) was taken with water (2 ml) in a 5 ml round bottom flask charged with Teflon-coated magnetic stir bar. After slow addition of trifluoroacetic acid (0.918 ml, 12 mmol), the flask was sealed with condenser. The reaction mixture was refluxed (bath temperature 200° C.) for 24 h and cooled to room temperature. The solvent was concentrated under reduced pressure delivering a yellow oil. To this, diethyl ether was added (3×3 ml) and stirred for overall 30 min at room temperature. The product crashes out as white precipitate which upon drying under reduced pressure delivers 1-(6-(4-carboxyphenoxy)hexyl)pyridin-1-ium bromide S30 (265.5 mg, 81% yield) as a white precipitate. $^{1}$H NMR (500 MHz, $CD_3OD$) δ 9.02 (d, J=5.5 Hz, 2H), 8.60 (m, J=7.8, 1.3 Hz, 1H), 8.12 (m, 2H), 7.95 (d, J=8.9 Hz, 2H), 6.95 (d, J=8.9 Hz, 2H), 4.67 (t, J=7.3 Hz, 2H), 4.06 (t, J=6.3 Hz, 2H), 2.08 (m, 2H), 1.83 (m, 2H), 1.59 (m, 2H), 1.49 (m, 2H) ppm. $^{13}$C NMR (126 MHz, $CD_3OD$) δ 168.4, 163.0, 145.5, 144.6, 131.4, 128.1, 122.6, 113.7, 67.5, 61.6, 31.0, 28.5, 25.4, 25.2 ppm. HRMS (ESI) $[M]^+$ calcd. for $C_{18}H_{22}NO_3$ 300.1607, found 300.1637.

Synthesis of (S)-1-(6-(4-((2-((1-amino-1-oxo-3-phenylpropan-2-yl)amino)-2-oxoethyl) carbamoyl) phenoxy)hexyl)pyridin-1-ium bromide 2h N-Hydroxysuccinimide S2 (23.0 mg, 0.2 mmol), N-ethyl-N'-(3-dimethylaminopropyl) carbodiimide hydrochloride (38.3 mg, 0.2 mmol), and dichloromethane (1 ml) were taken in a clean and dry 5 ml vial charged with magnetic stir bar. Next, 1-(6-(4-carboxyphenoxy) hexyl)pyridin-1-ium bromide S30 (19.0 mg, 0.05 mmol) was added to the reaction mixture and stirred at room temperature for 2 h to result sensitivity booster S57. The progress of reaction was followed by thin layer chromatography. The reaction mixture was diluted with dichloromethane (9 ml) and extracted with water (2×8 ml). The organic layer was dried over $Na_2SO_4$, concentrated, and the crude reagent was transferred into 5 ml vial charged with magnetic stir bar. After re-diluting it in acetonitrile (0.2 ml), Gly-Phe-$NH_2$ 1 (4.42 mg, 0.02 mmol) and triethylamine (2.76 μl, 0.02 mmol) were added through micropipette. The reaction mixture was stirred at room temperature for 2 h and followed by ESI-MS. It was further diluted to 500 μl by addition of acetonitrile and subjected to preparative HPLC to render pure (S)-1-(6-(4-((2-((1-amino-1-oxo-3-phenylpropan-2-yl)amino)-2-oxoethyl) carbamoyl)phenoxy)hexyl)pyridin-1-ium bromide 2h (3.0 mg, 30% yield) as white solid. $^{1}$H NMR (500 MHz, $D_2O$) δ 8.82 (d, J=5.8 Hz, 2H), 8.51 (t, J=7.8 Hz, 1H), 8.02 (m, 2H), 7.96 (d, J=8.7 Hz, 2H), 7.41 (m, 2H), 7.36 (m, 1H), 7.33 (m, 2H), 7.04 (d, J=8.7 Hz, 2H), 4.66 (dd, J=8.8, 6.3 Hz, 1H), 4.62 (t, J=7.2 Hz, 2H), 4.14 (t, J=6.3 Hz, 2H), 3.83-3.74 (m, 2H), 3.20 (dd, J=14.0, 6.5 Hz, 1H), 3.03 (dd, J=14.0, 8.9 Hz, 1H), 2.04 (m, 2H), 1.80 (m, 2H), 1.53 (m, 2H), 1.39 (m, 2H) ppm. $^{13}$C NMR ($D_2O$, 126 MHz) δ 175.8, 171.7, 171.3, 165.1, 145.4, 144.1, 136.1, 129.4, 129.2, 129.1, 128.7, 128.1, 127.1, 114.7, 68.3, 61.7, 54.3, 43.0, 36.8, 30.3, 27.7, 24.7, 24.5 ppm. HRMS (ESI) $[M]^+$ calcd. for $C_{29}H_{35}N_4O_4$ 503.2653, found 503.2632.

6.10 Procedure for Synthesis of Sensitivity Booster 1-benzyl-3-(6-(4-(((2,5-dioxopyrrolidin-1-yl)oxy)carbonyl)phenoxy)hexyl)-1H-imidazol-3-ium bromide (S58) and (S)-1-(6-(4-((2-((1-amino-1-oxo-3-phenylpropan-2-yl)amino)-2-oxoethyl)carbamoyl)phenoxy)hexyl)-3-benzyl-1H-imidazol-3-ium bromide 2i 129.0, 128.3, 127.3, 119.9, 50.8 ppm. HRMS (ESI) [M+H]$^+$ calcd. for $C_{10}H_{10}N_2$ 159.0917, found 159.0908.

Synthesis of 1-benzyl-3-(6-(4-(ethoxycarbonyl)phenoxy)hexyl)-1H-imidazol-3-ium bromide S32

In a 10 ml round bottom flask charged with Teflon-coated magnetic stir bar, 1-benzyl-1H-imidazole S31 (0.158 g, 1

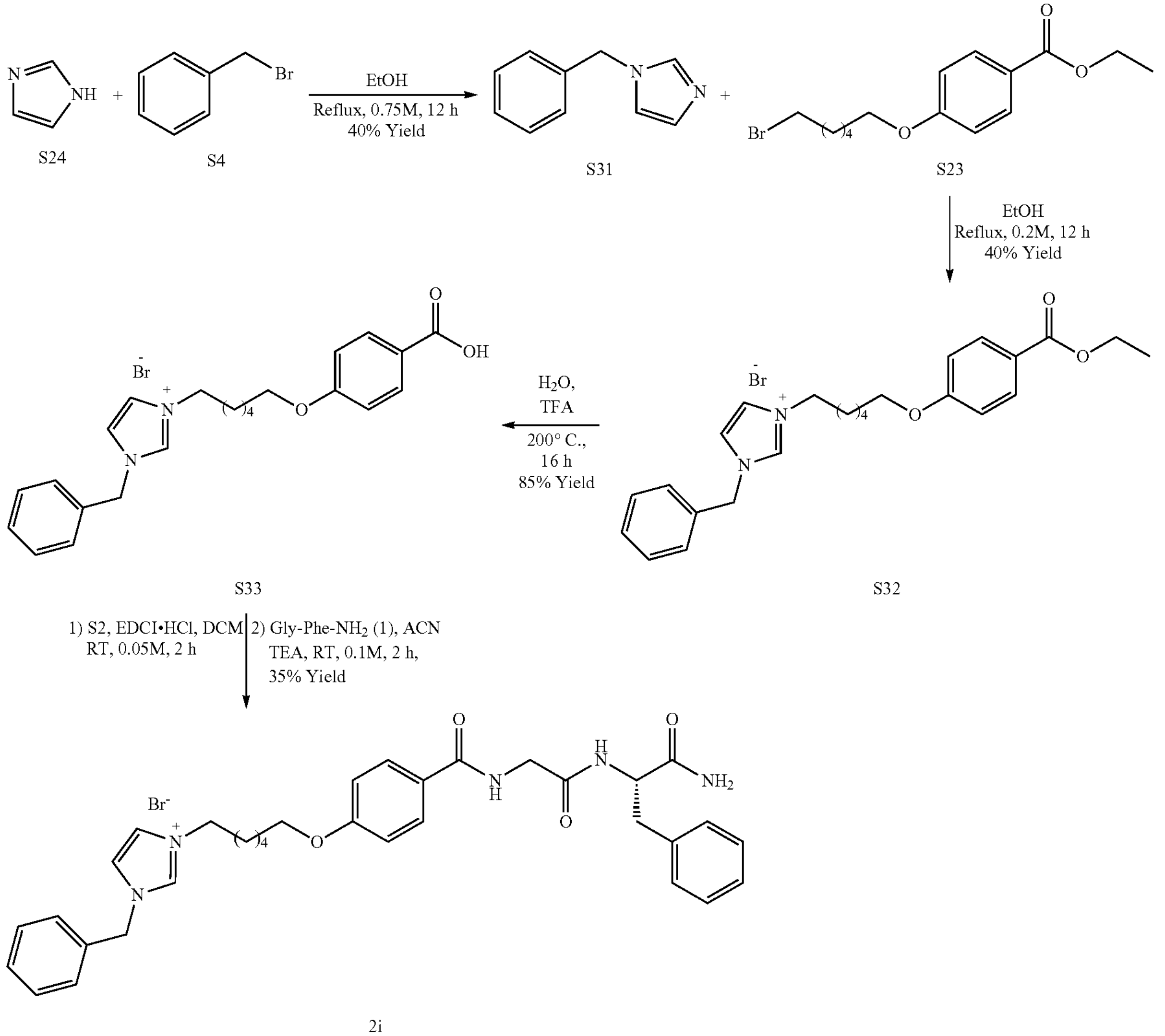

S24 S4 S31 S23 S33 S32 2i

Synthesis of 1-benzyl-1H-imidazole S31

Imidazole S24 (100 mg, 1.5 mmol), potassium carbonate (250 mg, 1.8 mmol), and ethanol (2 ml) were taken in 5 ml round bottom flask charged with Teflon-coated magnetic stir bar. Next, benzyl bromide S4 (0.20 ml, 1.8 mmol) was added and the reaction mixture was refluxed for 12 h. Subsequently, it was concentrated under reduced pressure and purified by a short chromatography column [DCM/MeOH, 95:5, Rr 0.5] to give the title compound 1-benzyl-1H-imidazole S31 (98.4 mg, 60% yield) as greenish solid. $^1$H NMR (500 MHz, $CDCl_3$) δ 7.54 (s, 1H), 7.39-7.30 (m, 3H), 7.18-7.14 (m, 2H), 7.09 (m, 1H), 6.90 (m, 1H), 5.11 (s, 2H) ppm. $^{13}$C NMR (126 MHz, $CDCl_3$) δ 137.5, 136.2, 129.8, mmol) was taken in 5 ml of ethanol. Next, ethyl 4-((6-bromohexyl)oxy)benzoate S23 (329 mg, 1 mmol) was added and the flask was sealed with a condenser. The reaction mixture was refluxed for 12 h and concentrated under reduced pressure. The residue was triturated with ether (5 ml) to give the title compound 1-benzyl-3-(6-(4-(ethoxycarbonyl)phenoxy)hexyl)-1H-imidazol-3-ium bromide S32 (388 mg, 80% yield) as a white solid. $^1$H NMR (500 MHz, $CDCl_3$) δ 10.83 (s, 1H), 7.97 (d, J=8.9 Hz, 2H), 7.49 (m, 2H), 7.37 (m, 2H), 7.36 (m, 1H), 7.36 (m, 1H), 7.31 (m, 1H), 6.88 (d, J=8.9 Hz, 2H), 5.60 (s, 2H), 4.42-4.28 (m, 4H), 3.98 (t, J=6.3 Hz, 2H), 1.96 (m, 2H), 1.78 (m, 2H), 1.52 (m, 2H), 1.43 (m, 2H), 1.37 (t, J=7.1 Hz, 3H) ppm. $^{13}$C NMR (126 MHz, $CDCl_3$) δ 166.4, 162.7, 137.5, 133.1, 131.5, 129.5, 129.4, 129.0, 122.8, 121.9, 121.7, 114.0, 67.7, 60.6, 53.3, 50.0, 30.1, 28.8, 25.9, 25.4, 14.4 ppm. HRMS (ESI) $[M]^+$ calcd. for $C_{25}H_{31}N_2O_3$ 407.2329, found 407.2302.

Synthesis of 1-benzyl-3-(6-(4-carboxyphenoxy) hexyl)-1H-imidazol-3-ium bromide S33

In a 10 ml round bottom flask charged with Teflon-coated magnetic stir bar, 1-benzyl-3-(6-(4-(ethoxycarbonyl)phenoxy)hexyl)-1H-imidazol-3-ium bromide S32 (487 mg, 1 mmol) was taken in 2 ml of water. Next, trifluoroacetic acid (0.918 ml, 12 mmol) was added slowly and the flask was sealed with condenser. The reaction mixture was refluxed (bath temperature 200° C.) for 24 h and cooled to room temperature. The solvent was concentrated under reduced pressure to deliver a yellow oil. To this, diethyl ether was added (3×3 ml) and stirred for overall 30 min at room temperature. The crashed out white precipitate is isolated and dried under reduced pressure to deliver 1-benzyl-3-(6-(4-carboxyphenoxy)-hexyl)-1H-imidazol-3-ium bromide S33 (366 mg, 84% yield). $^1H$ NMR (500 MHz, $CD_3OD$) δ 7.95 (d, J=8.9 Hz, 2H), 7.67 (d, J=2.0 Hz, 1H), 7.63 (d, J=2.0 Hz, 1H), 7.47-7.38 (m, 5H), 6.95 (d, J=8.9 Hz, 2H), 5.41 (s, 2H), 4.24 (t, J=7.3 Hz, 2H), 4.04 (t, J=6.3 Hz, 2H), 1.93 (m, 2H), 1.81 (m, 2H), 1.55 (m, 2H), 1.41 (m, 2H) ppm (1 exchangeable proton in addition to carboxylic acid). $^{13}C$ NMR (126 MHz, $CD_3OD$) δ 168.4, 163.0, 133.8, 131.4, 129.1, 129.0, 128.2, 122.7, 122.6, 122.5, 113.7, 67.5, 52.7, 49.5, 29.6, 28.5, 25.5, 25.1 ppm. HRMS (ESI) $[M]^+$ calcd. for $C_{23}H_{27}N_2O_3$ 379.2016, found 379.1995.

Synthesis of (S)-1-(6-(4-((2-((1-amino-1-oxo-3-phenylpropan-2-yl)amino)-2-oxoethyl)carbamoyl) phenoxy)hexyl)-3-benzyl-1H-imidazol-3-ium bromide 2i In a 5 ml vial charged with magnetic stir bar, N-hydroxysuccinimide S2 (23.0 mg, 0.2 mmol) and N-ethyl-N'-(3-dimethylaminopropyl)carbodiimide hydrochloride (38.3 mg, 0.2 mmol) were taken in 1 ml of dichloromethane. Next, 1-benzyl-3-(6-(4-carboxyphenoxy)hexyl)-1H-imidazol-3-ium bromide S33 (19.0 mg, 0.05 mmol) was added and the reaction mixture was stirred at room temperature for 2 h to result sensitivity booster S58. The progress of reaction was followed by thin layer chromatography. The reaction mixture was diluted with dichloromethane (9 ml) and extracted with water (2×8 ml). The organic layer was dried over $Na_2SO_4$, concentrated, and the crude reagent was transferred into 5 ml vial charged with magnetic stir bar. It was re-diluted with acetonitrile (0.2 ml) followed by addition of Gly-Phe-$NH_2$ 1 (4.42 mg, 0.02 mmol) and triethyl amine (2.76 μl, 0.02 mmol). The reaction mixture was stirred at room temperature for 2 h. It was diluted to 500 μl by acetonitrile and subjected to preparative HPLC to render (S)-1-(6-(4-((2-((1-amino-1-oxo-3-phenylpropan-2-yl) amino)-2-oxoethyl)carbamoyl)phenoxy)hexyl)-3-benzyl-1H-imidazol-3-ium bromide 2i (3.03 mg, 26% yield). $^1H$ NMR (500 MHz, $D_2O$) δ 8.78 (s, 1H), 7.72 (d, J=8.8 Hz, 2H), 7.46 (m, 1H), 7.43-7.41 (m, 4H), 7.33-7.31 (m, 2H), 7.23-7.15 (m, 5H), 7.01 (d, J=8.9 Hz, 2H), 5.30 (s, 2H), 4.62 (dd, J=8.6, 5.6 Hz, 1H), 4.18 (t, J=6.8 Hz, 2H), 4.07 (t, J=6.3 Hz, 2H), 4.04-3.95 (m, 2H), 3.17 (dd, J=14.0, 5.6 Hz, 1H), 2.99 (dd, J=14.0, 8.6 Hz, 1H), 1.86 (m, 2H), 1.74 (m, 2H), 1.44 (m, 2H), 1.27 (m, 2H) ppm. $^{13}C$ NMR ($D_2O$, 126 MHz) δ 175.7, 171.6, 170.0, 161.6, 136.1, 133.6, 131.0, 129.4, 129.3, 129.2, 129.1, 128.7, 128.3, 127.1, 124.9, 122.5, 122.4, 114.6, 68.2, 54.2, 52.7, 49.5, 43.0, 36.9, 28.8, 27.7, 24.7, 24.3 ppm. HRMS (ESI) $[M]^+$ calcd. for $C_{34}H_{40}N_5O_4$ 583.3153, found 583.3123.

6.11 Procedure for Synthesis of Sensitivity Booster 4-(dimethylamino)-1-(6-(4-(((2,5-dioxopyrrolidin-1-yl)oxy)carbonyl)phenoxy)hexyl)pyridin-1-ium bromide (S59) and (S)-1-(6-(4-((2-((1-amino-1-oxo-3-phenylpropan-2-yl)amino)-2-oxoethyl) carbamoyl) phenoxy)hexyl)-4-(dimethylamino)pyridin-1-ium bromide 2j

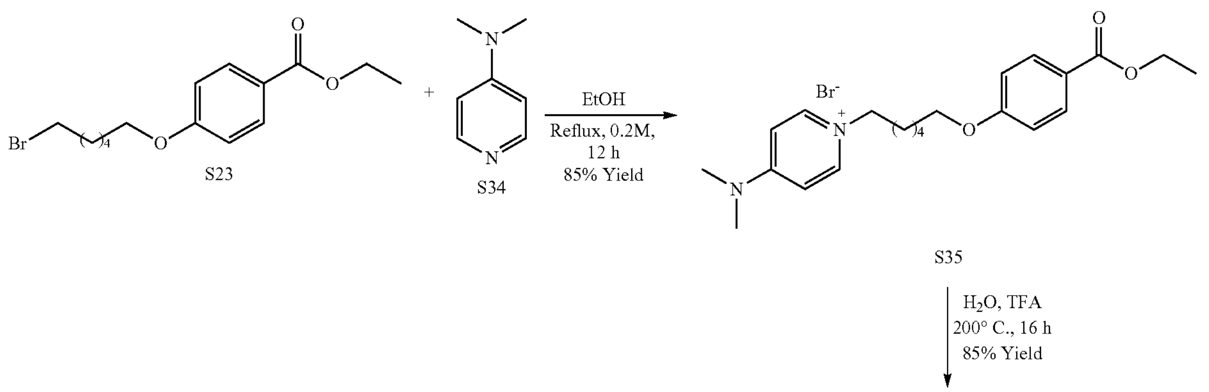

S23 S34 S35

-continued

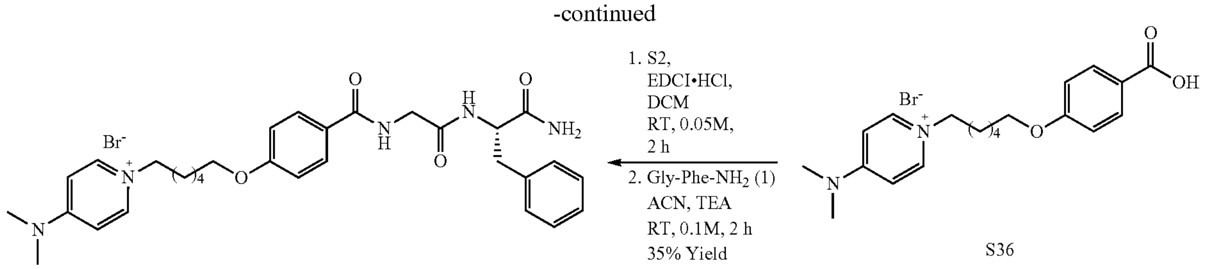

2j

S36

Synthesis of 1-(6-(4-(ethoxycarbonyl)phenoxy) hexyl))-4-(dimethylamino)pyridin-1-ium bromide S35

In a 10 ml round bottom flask charged with Teflon-coated magnetic stir bar, 4-(dimethylamino)pyridine S34 (0.122 g, 1 mmol) was taken in 5 ml of ethanol. Next, ethyl 4-((6-bromohexyl)oxy)benzoate S23 (329 mg, 1 mmol) was added, sealed by the condenser, and refluxed for 12 h. The reaction mixture was concentrated under reduced pressure and triturated with ether (5 ml) to give the title compound of 1-(6-(4-(ethoxycarbonyl)phenoxy)hexyl))-4-(dimethylamino)pyridin-1-ium bromide S35 (360 mg, 80% yield) as a white solid. $^{1}$H NMR (500 MHz, $CDCl_3$) δ 8.53 (d, J=7.8 Hz, 2H), 7.96 (d, J=8.9 Hz, 2H), 6.98 (d, J=7.8 Hz, 2H), 6.88 (d, J=8.9 Hz, 2H), 4.40 (t, J=7.2 Hz, 2H), 4.34 (q, J=7.1 Hz, 2H), 3.99 (t, J=6.2 Hz, 2H), 3.25 (s, 6H), 1.93 (m, 2H), 1.79 (m, 2H), 1.52 (m, 2H), 1.43 (m, 2H), 1.37 (t, J=7.1 Hz, 3H) ppm. $^{13}$C NMR (126 MHz, $CDCl_3$) δ 166.4, 162.7, 156.2, 142.5, 131.5, 122.7, 114.0, 108.3, 67.7, 60.6, 58.0, 40.5, 31.0, 28.8, 25.7, 25.5, 14.4 ppm. HRMS (ESI) $[M]^+$ calcd. for $C_{22}H_{31}N_2O_3$ 371.2329, found 371.2355.

Synthesis of 1-(6-(4-carboxyphenoxy)hexyl)-4-(dimethylamino)pyridin-1-ium bromide S36

In a 5 ml round bottom flask charged with Teflon-coated magnetic stir bar, 1-(6-(4-(ethoxycarbonyl)phenoxy) hexyl))-4-(dimethylamino)pyridin-1-ium bromide S35 (423 mg, 1 mmol) was taken in 2 ml of water. Next, trifluoroacetic acid (0.918 ml, 12 mmol) was added slowly and the flask was sealed by condenser. The reaction mixture was refluxed (bath temperature 200° C.) for 24 h and cooled to room temperature. The solvent was concentrated under reduced pressure delivering a yellow oil. To this, diethyl ether was added (3×3 ml) and stirred for overall 30 min at room temperature. The white precipitate is isolated and dried under reduced pressure to deliver 1-(6-(4-carboxyphenoxy) hexyl)-4-(dimethylamino)pyridin-1-ium bromide S36 (355 mg, 84% yield). $^{1}$H NMR (500 MHz, $CD_3OD$) δ 8.06 (d, J=7.8 Hz, 2H), 7.84 (d, J=8.9 Hz, 2H), 6.85 (d, J=7.9 Hz, 2H), 6.85 (d, J=8.9 Hz, 2H), 4.09 (t, J=7.2 Hz, 2H), 3.94 (t, J=6.2 Hz, 2H), 1.80 (m, 2H), 1.71 (m, 2H), 1.45 (m, 2H), 1.31 (m, 2H) ppm. $^{13}$C NMR (126 MHz, $CD_3OD$) δ 168.5, 163.0, 156.5, 141.6, 131.4, 131.1, 113.8, 107.9, 67.5, 57.4, 38.9, 30.4, 28.5, 25.3, 25.1 ppm. HRMS (ESI) $[M]^+$ calcd. for $C_{20}H_{27}N_2O_3$ 343.2016, found 343.2003.

Synthesis of (S)-1-(6-(4-((2-((1-amino-1-oxo-3-phenylpropan-2-yl)amino)-2-oxoethyl) carbamoyl) phenoxy)hexyl)-4-(dimethylamino)pyridin-1-ium bromide 2j In a 5 ml vial charged with Teflon-coated magnetic stir bar, N-hydroxysuccinimide S2 (23.0 mg, 0.2 mmol) and N-ethyl-N'-(3-dimethylaminopropyl)carbodiimide hydrochloride (38.3 mg, 0.2 mmol) were taken in dichloromethane (1 ml). Next, 1-(6-(4-carboxyphenoxy)hexyl)-4-(dimethylamino)pyridin-1-ium bromide S36 (21.1 mg, 0.05 mmol) was added and reaction mixture was stirred at room temperature for 2 h to result sensitivity booster S59. The progress of reaction was followed by thin layer chromatography. The reaction mixture was diluted with dichloromethane (9 ml) and extracted with water (2×8 ml). The organic layer was dried over $Na_2SO_4$, concentrated, and crude reagent was transferred into 5 ml vial charged with magnetic stir bar. It was re-diluted with acetonitrile (0.2 ml) followed by the addition of Gly-Phe-$NH_2$ 1 (4.42 mg, 0.02 mmol) and triethyl amine (2.76 μl, 0.02 mmol). The mixture was stirred at room temperature for 2 h. It was diluted further to 500 μl by addition of acetonitrile and subjected to preparative HPLC to render 1-(6-(4-((2-((1-amino-1-oxo-3-phenylpropan-2-yl)amino)-2-oxoethyl)carbamoyl)phenoxy)hexyl)-4-(dimethylamino)pyridin-1-ium bromide 2j (2.75 mg, 25% yield). $^{1}$H NMR (500 MHz, $D_2O$) δ 7.93 (d, J=7.5 Hz, 2H), 7.74 (d, J=8.7 Hz, 2H), 7.38 (m, 1H), 7.22-7.15 (m, 4H), 7.05 (d, J=8.8 Hz, 2H), 6.72 (d, J=7.6 Hz, 2H), 4.63 (dd, J=8.6, 5.6 Hz, 1H), 4.17-4.09 (m, 4H), 4.02 (m, 2H), 3.19 (dd, J=14.0, 5.6 Hz, 1H), 3.07 (s, 6H), 3.02 (dd, J=14.1, 8.4 Hz, 1H), 1.87 (m, 2H), 1.80 (m, 2H), 1.51 (m, 2H), 1.32 (m, 2H) ppm. $^{13}$C (126 MHz, $D_2O$) δ 178.3, 174.2, 172.5, 164.1, 158.6, 143.7, 131.9, 131.7, 131.6, 131.2, 129.6, 127.4, 117.2, 109.8, 70.7, 59.9, 56.7, 45.5, 41.7, 39.4, 32.0, 30.0, 27.0, 26.9 ppm. HRMS (ESI) $[M]^+$ calcd. for $C_{31}H_{40}N_5O_4$ 546.3075, found 546.3072.

6.12 Synthesis 6-(4-((2-((1-amino-1-oxo-3-phenylpropan-2-yl)amino)-2-oxoethyl)carbamoyl) phenoxy)-N-(bis(dimethylamino)methylene)-N-butylhexan-1-aminium bromide 2k

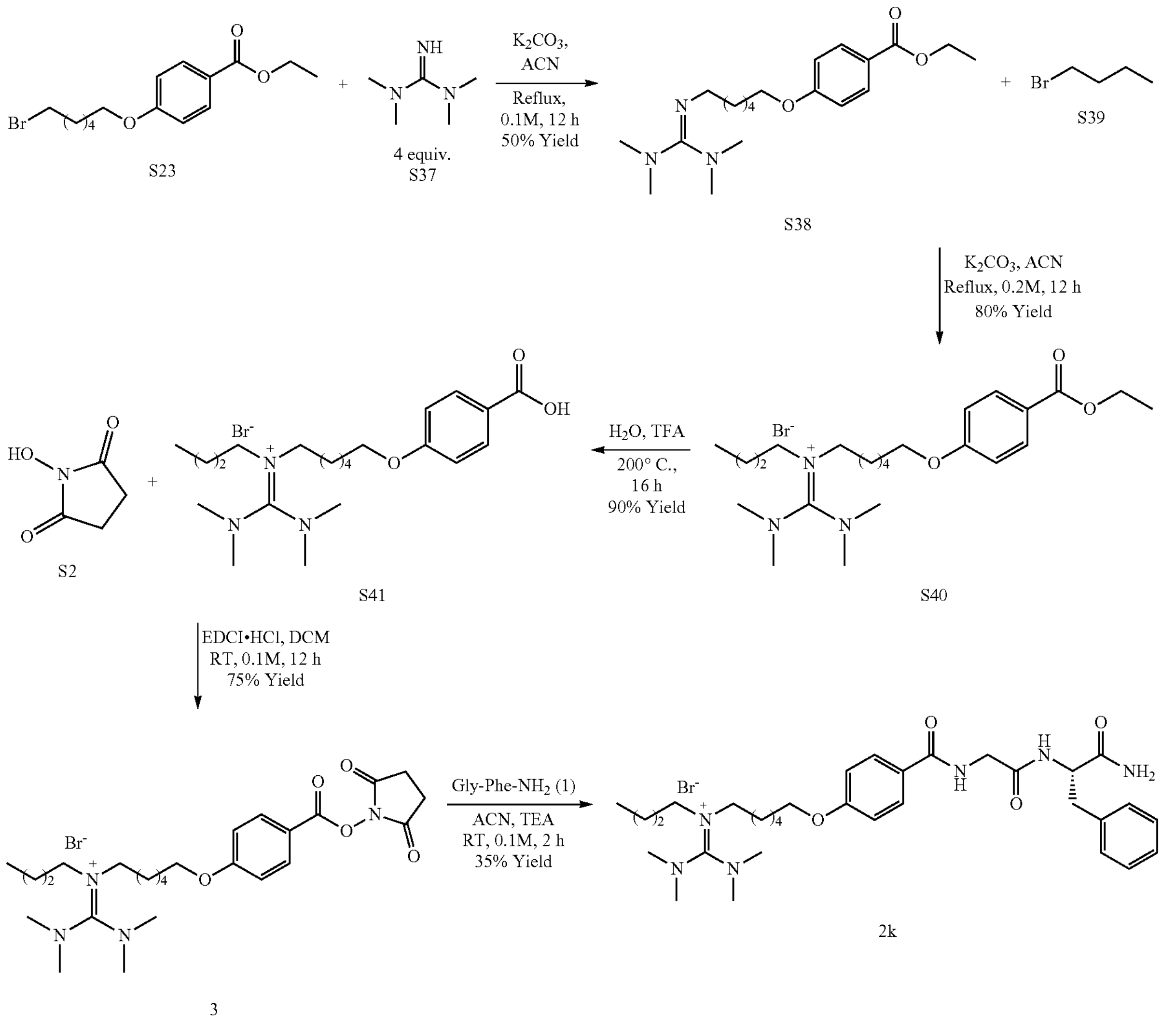

Ethyl 4-(6-((bis(dimethylamino)methylene)amino) hexyl)benzoate S38

In a 10 ml round bottom flask charged with Teflon-coated magnetic stir bar, potassium carbonate (0.68 g, 4.92 mmol) and N,N-tetramethyl guanidine S37 (0.375 ml, 3 mmol) were taken in acetonitrile (5 ml). Next, ethyl 4-(3-bromohexyl) benzoate S23 (0.33 g, 1 mmol) was added and the reaction mixture was refluxed for 12 h. It was concentrated under reduced pressure and the resulting residue was rediluted with dichloromethane (10 ml). The organic layer was extracted with water (3×50 ml) to remove S37 and potassium carbonate. The organic extracts were dried over $Na_2SO_4$ and the solvent was concentrated under reduced pressure. The residue was suspended in diethyl ether (15 ml) and stirred for 1 h. The process was repeated twice to extract all the product in ether layer. The ether fractions were combined and concentrated under reduced pressure to afford the pure ethyl 4-(6-((bis(dimethylamino)methylene)amino) hexyl)benzoate S38 (181.5 mg, 50% yield) as slightly yellow colour liquid. $^{1}H$ NMR (500 MHz, $CDCl_3$) δ 7.98 (d, J=8.7 Hz, 2H), 6.89 (d, J=8.7 Hz, 2H), 4.34 (q, J=7.1 Hz, 2H), 4.00 (t, J=6.6 Hz, 2H), 3.11 (t, J=6.9 Hz, 2H), 2.74 (s, 6H), 2.65 (s, 6H), 1.81 (m, 2H), 1.56 (m, 2H), 1.48 (m, 2H), 1.42 (m, 2H), 1.38 (t, J=7.1 Hz, 3H) ppm. $^{13}C$ NMR (126 MHz, $CDCl_3$) δ 166.4, 162.9, 160.1, 131.5, 122.6, 114.0, 68.2, 60.5, 49.2, 39.6, 38.9, 32.5, 29.1, 27.1, 25.8, 14.4 ppm. HRMS (ESI) $[M+H]^+$ calcd. for $C_{20}H_{33}N_3O_3$ 364.2595, found 364.2602.

N-(bis(dimethylamino)methylene)-N-butyl-6-(4-(ethoxycarbonyl)phenoxy)hexan-1-aminium bromide S40

In a 10 ml round bottom flask charged with Teflon-coated magnetic stir bar, potassium carbonate (680 mg, 4.92 mmol)

and n-butyl bromide S39 (0.375 ml, 3 mmol) were taken in acetonitrile (5 ml). Next, ethyl 4-(3-((bis(dimethylamino) methylene)amino)hexyl)benzoate S38 (363 mg, 1 mmol) was added and the reaction mixture was refluxed for 12 h. Subsequently, it was concentrated under reduced pressure and re-diluted with dichloromethane (10 ml). The organic layer was extracted with water (3×50 ml) to remove the base. The organic layer was dried over $Na_2SO_4$ and the solvent was concentrated under reduced pressure. To this, 15 ml diethyl ether was added and stirred for 1 h. The process was repeated twice to extract all the product in ether layer. The ether fractions were combined and concentrated under reduced pressure to afford the pure N-(bis(dimethylamino) methylene)-N-butyl-6-(4-(ethoxycarbonyl)phenoxy)hexan-1-aminium bromide S40 (400 mg, 80% yield) as slightly yellow coloured liquid. $^1$H NMR (500 MHz, $CDCl_3$) δ 7.99 (d, J=8.6 Hz, 2H), 6.90 (d, J=8.6 Hz, 2H), 4.35 (q, J=7.1 Hz, 2H), 4.03 (t, J=6.2 Hz, 2H), 3.35-3.18 (m, 4H), 3.15 (s, 6H), 3.07 (s, 6H), 1.83 (m, 2H), 1.72-1.44 (m, 8H), 1.40-1.32 (m, 5H), 0.96 (t, J=7.3 Hz, 3H) ppm. $^{13}$C NMR (126 MHz, $CDCl_3$) δ 168.3, 163.3, 163.1, 131.5, 122.5, 113.8, 67.6, 65.5, 49.4, 49.2, 39.2, 39.0, 29.4, 28.6, 27.3, 26.1, 25.3, 19.6, 14.0, 12.6 ppm. HRMS (ESI) $[M]^+$ calcd. for $C_{24}H_{42}N_3O_3$ 420.3221, found 420.3209.

N-(bis(dimethylamino)methylene)-N-butyl-6-(4-carboxyphenoxy)hexan-1-aminium bromide S41

In a 5 ml round bottom flask charged with Teflon-coated magnetic stir bar, N-(bis(dimethylamino)methylene)-N-butyl-6-(4-(ethoxycarbonyl)phenoxy)hexan-1-aminium bromide S40 (499 mg, 1 mmol) was taken in 2 ml of water. Next, trifluoroacetic acid (0.918 ml, 12 mmol) was added slowly and the flask was sealed with a condenser. The reaction mixture was refluxed (bath temperature 200° C.) for 24 h and cooled to room temperature. The solvent was concentrated under reduced pressure delivering a yellow oil. To this, diethyl ether was added (3×3 ml) and stirred for overall 30 min at room temperature. The white precipitate from this process melts upon drying under reduced pressure, delivering N-(bis(dimethylamino)methylene)-N-butyl-6-(4-carboxyphenoxy)hexan-1-aminium bromide S41 (376 mg, 80% yield) as a yellow coloured liquid. $^1$H NMR (500 MHz, $CD_3OD$) δ 7.96 (d, J=8.9 Hz, 2H), 6.96 (d, J=8.9 Hz, 2H), 4.07 (t, J=6.3 Hz, 2H), 3.27 (m, 2H), 3.18 (m, 2H), 2.97 (s, 6H), 2.95 (s, 6H), 1.82 (m, 2H), 1.67 (m, 2H), 1.59-1.44 (m, 4H), 1.44-1.29 (m, 4H), 0.97 (t, J=7.4 Hz, 3H) ppm. $^{13}$C NMR (126 MHz, $CD_3OD$) δ 168.4, 163.3, 163.1, 131.5, 122.6, 113.7, 67.6, 49.4, 49.3, 39.1, 39.0, 29.4, 28.6, 27.3, 26.1, 25.3, 19.6, 12.6 ppm. HRMS (ESI) $[M]^+$ calcd. for $C_{22}H_{38}N_3O_3$ 392.2908, found 392.2933.

Synthesis of N-(bis(dimethylamino)methylene)-N-butyl-6-(4-(((2,5-dioxopyrrolidin-1-yl)oxy)carbonyl)phenoxy)hexan-1-aminium bromide 3

In a 5 ml vial charged with Teflon-coated magnetic stir bar, N-hydroxysuccinimide S2 (23.0 mg, 0.2 mmol) and N-ethyl-N'-(3-dimethylaminopropyl)carbodiimide hydrochloride (38.3 mg, 0.2 mmol) were taken in dichloromethane (1 ml). Next, N-(bis(dimethylamino)methylene)-N-butyl-6-(4-carboxyphenoxy)hexan-1-aminium bromide S41 (47.1 mg, 0.1 mmol) was added and the reaction mixture was stirred at room temperature for 2 h. The progress of reaction was followed by thin layer chromatography. Next, it was diluted with dichloromethane (9 ml) and extracted with water (2×8 ml). The organic layer was dried over $Na_2SO_4$ and concentrated under reduced pressure. The resulting residue was triturated with ether and pentane (2 ml each) to yield N-(bis(dimethylamino)methylene)-N-butyl-6-(4-(((2,5-dioxopyrrolidin-1-yl)oxy)carbonyl)phenoxy) hexan-1-aminium bromide 3 (397 mg, yield 70%) as colourless liquid. $^1$H NMR (500 MHz, $CDCl_3$) δ 8.07 (d, J=8.8 Hz, 2H), 6.96 (d, J=8.9 Hz, 2H), 4.06 (t, J=6.1 Hz, 2H), 3.26-3.16 (m, 4H), 3.14 (s, 6H), 3.05 (s, 6H), 2.91 (s, 4H), 1.83 (m, 2H), 1.75-1.49 (m, 4H), 1.47-1.25 (m, 6H), 0.95 (t, J=7.3 Hz, 3H) ppm. $^{13}$C NMR (126 MHz, $CDCl_3$) δ 169.5, 164.4, 163.3, 161.5, 132.9, 116.9, 114.7, 68.1, 49.7, 49.3, 41.0, 40.8, 29.8, 28.8, 27.8, 26.5, 25.7, 20.0, 13.7 ppm. HRMS (ESI) $[M]^+$ calcd. for $C_{26}H_{41}N_4O_5$ 489.3071, found 489.3063.

Synthesis of (S)-6-(4-((2-((1-amino-1-oxo-3-phenylpropan-2-yl)amino)-2-oxoethyl) carbamoyl)phenoxy)-N-(bis(dimethylamino)methylene)-N-butylhexan-1-aminium bromide 2k In a 5 ml vial charged with Teflon-coated magnetic stir bar, Gly-Phe-$NH_2$ 1 (4.42 mg, 0.02 mmol) was taken in acetonitrile (200 μl). Next, N-(bis(dimethylamino)methylene)-N-butyl-6-(4-(((2,5-dioxopyrrolidin-1-yl)oxy)carbonyl)phenoxy)hexan-1-aminium bromide S42 (22.4 mg, 0.04 mmol) and triethyl amine (2.76 1, 0.02 mmol) were added and the resulting reaction mixture was stirred at room temperature for 2 h. The reaction mixture was diluted to 500 μl with acetonitrile and purified by preparative HPLC to give pure (S)-6-(4-((2-((1-amino-1-oxo-3-phenylpropan-2-yl) amino)-2-oxoethyl)carbamoyl)phenoxy)-N-(bis(dimethylamino)methylene)-N-butylhexan-1-aminium bromide 2k (3.8 mg, 35% yield) as white solid. $^1$H NMR (500 MHz, $CD_3OD$) δ 7.71 (d, J=8.8 Hz, 2H), 7.13 (m, 2H), 7.12 (m, 2H), 7.06 (m, 1H), 6.87 (d, J=8.9 Hz, 2H), 4.54 (dd, J=8.7, 5.3 Hz, 1H), 3.97 (t, J=6.2 Hz, 2H), 3.90-3.80 (m, 2H), 3.17 (m, 2H), 3.10-3.07 (m, 3H), 2.86 (s, 12H), 2.82 (m, 1H), 1.73 (m, 2H), 1.66-1.51 (m, 2H), 1.50-1.36 (m, 4H), 1.35-1.20 (m, 4H), 0.87 (t, J=7.4 Hz, 3H) ppm. $^{13}$C NMR (126 MHz, $CD_3OD$) δ 174.6, 170.3, 168.7, 163.3, 162.2, 137.0, 129.0, 128.9, 129.0, 126.4, 125.5, 113.8, 67.6, 54.2, 49.4, 49.2, 42.7, 39.1, 38.9, 37.4, 29.4, 28.6, 27.3, 26.1, 25.4, 19.6, 12.6 ppm. HRMS (ESI) $[M]^+$ calcd. For $C_{33}H_{51}N_6O_4$ 595.3966, found 595.3969.

6.13 Procedure for Synthesis of 2,5-dioxopyrrolidin-1-yl benzoate 7 (see Scheme 3a)

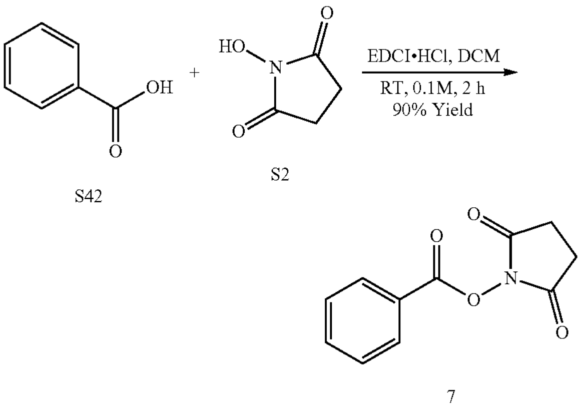

S42 S2

7

Synthesis of 2,5-dioxopyrrolidin-1-yl benzoate 7

In a 5 ml vial charged with Teflon-coated magnetic stir bar, N-hydroxysuccinimide S2 (23.0 mg, 0.2 mmol) and N-ethyl-N'-(3-dimethylaminopropyl)carbodiimide hydrochloride (38.3 mg, 0.2 mmol) were taken in dichloromethane (1 ml). Next, benzoic acid S42 (0.122 g, 0.1 mmol) was added and stirred at room temperature for 2 h. The reaction was followed by thin layer chromatography. After completion, the reaction mixture was diluted with dichloromethane (9 ml) and extracted with water (2×8 ml). The organic layer was dried over $Na_2SO_4$ and concentrated under reduced pressure. The resulting residue was triturated with diethyl ether and pentane (2 ml each) to yield 2,5-dioxopyrrolidin-1-yl benzoate 7 (13.4 mg, yield 90%) as white solid. $^1H$ NMR (500 MHz, $CDCl_3$) δ 8.16 (m, 2H), 7.71 (m, 1H), 7.51 (m, 2H), 2.91 (s, 4H) ppm. $^{13}C$ NMR (126 MHz, $CDCl_3$) δ 169.2, 161.9, 134.9, 130.6, 128.9, 125.2, 25.7. HRMS (ESI) $[M+Na]^+$ calcd. for $C_{11}H_9NO_4$ 242.0424, found 242.0428.

6.14 Procedure for Synthesis of 2,5-dioxopyrrolidin-1-yl 4-(4-formylphenoxy)butanoate 8

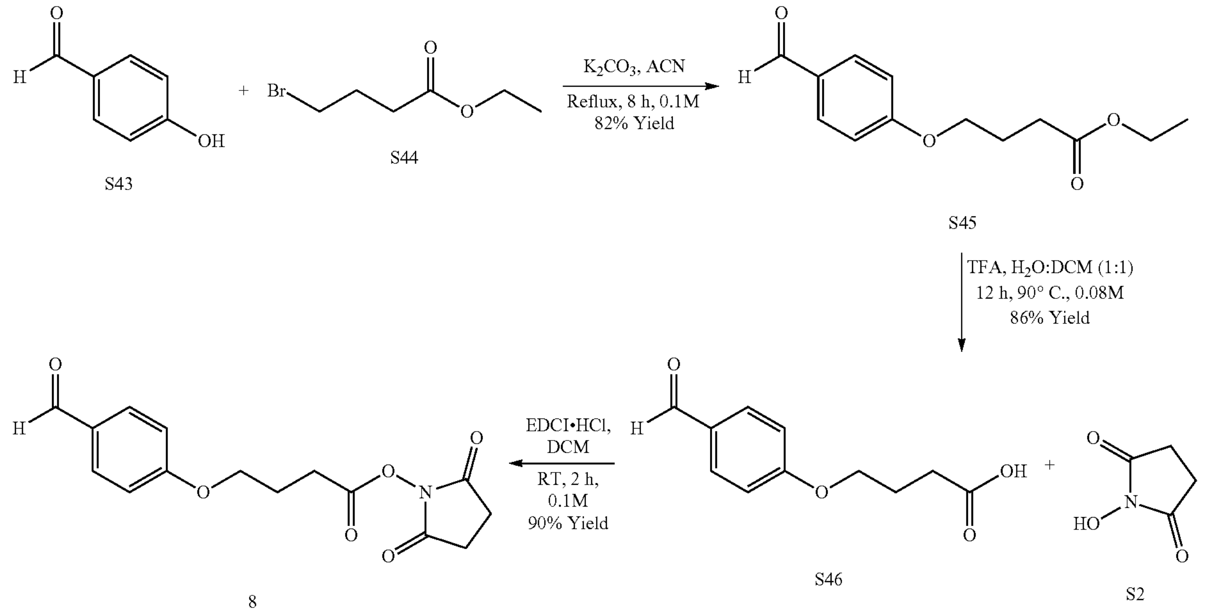

S43 S44 S45 S46 S2 8

Synthesis of ethyl 4-(4-formylphenoxy)butanoate S45[8]

In a 25 ml round bottom flask, p-hydroxybenzaldehyde S43 (122.1 mg, 1 mmol) was dissolved in acetonitrile (10 ml). To this aldehyde solution, $K_2CO_3$ (276.4 mg, 2 mmol) and ethyl 4-bromobutanoate S44 (0.17 ml, 1.2 mmol) were added and reaction mixture was allowed to reflux for 8 h. The reaction progress was monitored by thin layer chromatography (TLC). Upon completion, the reaction mixture was filtered to remove $K_2CO_3$. The solution was concentrated under vacuum and the product was purified using flash column chromatography (ethylacetate:n-hexane 2:98) to afford ethyl 4-(4-formylphenoxy)butanoate S45 (82% yield). $^1H$ NMR (400 MHz, $CDCl_3$) δ 9.88 (s, 1H), 7.83 (d, J=8.6 Hz, 2H), 6.99 (d, J=8.7 Hz, 2H), 4.15 (q, J=7.2 Hz, 2H), 4.11 (t, J=6.2 Hz, 2H), 2.53 (t, J=7.2 Hz, 2H), 2.15 (m, 2H), 1.26 (t, J=7.1 Hz, 3H). $^{13}C$ NMR (101 MHz, $CDCl_3$) δ 190.9, 173.1, 164.0, 132.1, 130.0, 114.8, 67.2, 60.6, 30.7, 24.5, 14.3. MS (ESI) $[MH]^+$ calcd. for $C_{13}H_{16}O_4$ 237.1, found 237.1.

Synthesis of 4-(4-formylphenoxy)butanoic acid S46[8]

The ester derivative S45 (194 mg, 0.82 mmol) was dissolved in water and DCM mixture (10 ml, 1:1). To this solution, trifluoroacetic acid (4 equiv.) was added and reaction temperature was elevated to 90° C. The reaction mixture was stirred for another 12 h and the hydrolysis of ester was monitored by TLC. Subsequently, the precipitated crude product was filtered and subjected to silica-gel flash column chromatography (ethylacetate:n-hexane 35:65) to afford the pure product S46 (86% yield). $^1H$ NMR (500 MHz, DMSO-$d_6$) δ 9.86 (s, 1H), 7.86 (d, J=8.7 Hz, 2H), 7.12 (d, J=8.7 Hz, 2H), 4.11 (t, J=6.4 Hz, 2H), 2.39 (t, J=7.3 Hz, 2H), 1.97 (m, 2H). $^{13}C$ NMR (126 MHz, DMSO-$d_6$) δ 191.7, 174.4, 163.9, 132.3, 130.0, 115.3, 67.6, 30.4, 24.5. MS (ESI) $[MH]^+$ calcd. for $C_{11}H_{13}O_4$ 209.2, found 209.2.

Synthesis of 2,5-dioxopyrrolidin-1-yl 4-(4-formylphenoxy)butanoate 8

In a 5 ml vial charged with Teflon-coated magnetic stir bead, N-hydroxysuccinimide S2 (23.0 mg, 0.2 mmol) and N-ethyl-N'-(3-dimethylaminopropyl)carbodiimide hydrochloride (38.3 mg, 0.2 mmol) were taken in dichloromethane (1 ml). Next, 4-(4-formylphenoxy)butanoic acid S46 (20.8 g, 0.1 mmol) was added and stirred at room temperature for 2 h. The progress of reaction was followed by thin layer chromatography. The reaction mixture was diluted with dichloromethane (9 ml) and extracted with water (2×8 ml). The organic layer was dried over $Na_2SO_4$ and concentrated under reduced pressure. The resulting residue was triturated with ether and pentane (2 ml each) to yield 2,5-dioxopyrrolidin-1-yl 4-(4-formylphenoxy)butanoate 8

(27.4 mg, yield 90%) as white solid. $^{1}$H NMR (500 MHz, $CDCl_3$) δ 9.91 (s, 1H), 7.86 (d, J=8.8 Hz, 2H), 7.04 (d, J=8.8 Hz, 2H), 4.18 (t, J=6.0 Hz, 2H), 2.90 (t, J=6.0 Hz, 2H), 2.87 (s, 4H), 2.29 (m, 2H) ppm. $^{13}$C NMR (126 MHz, $CDCl_3$) δ 190.8, 169.1, 168.2, 163.6, 132.0, 130.1, 114.8, 66.3, 27.7, 25.6, 24.3 ppm. HRMS (ESI) $[MH]^+$ calcd. for $C_{15}H_{15}NO_6$ 306.0972, found 306.0993.

6.15 Procedure for Synthesis of 6-(aminooxy)-N-(bis(dimethylamino)methylene)-N-(6-phenoxyhexyl) hexan-1-aminium bromide 9

Synthesis of 1,1,3,3-tetramethyl-2-(6-phenoxyhexyl)guanidine S48

In a 10 ml round bottom flask charged with Teflon-coated magnetic stir bead, potassium carbonate (680 mg, 4.92 mmol) and N, N-tetramethyl guanidine S37 (0.375 ml, 3 mmol) were taken in acetonitrile (5 ml). Next, 1-(6-bromo-hexyloxy) benzene S23 (257 mg, 1 mmol) was added and reaction mixture was refluxed for 12 h. Subsequently, it was concentrated under reduced pressure and the residue was re-diluted with dichloromethane (10 ml). The organic layer

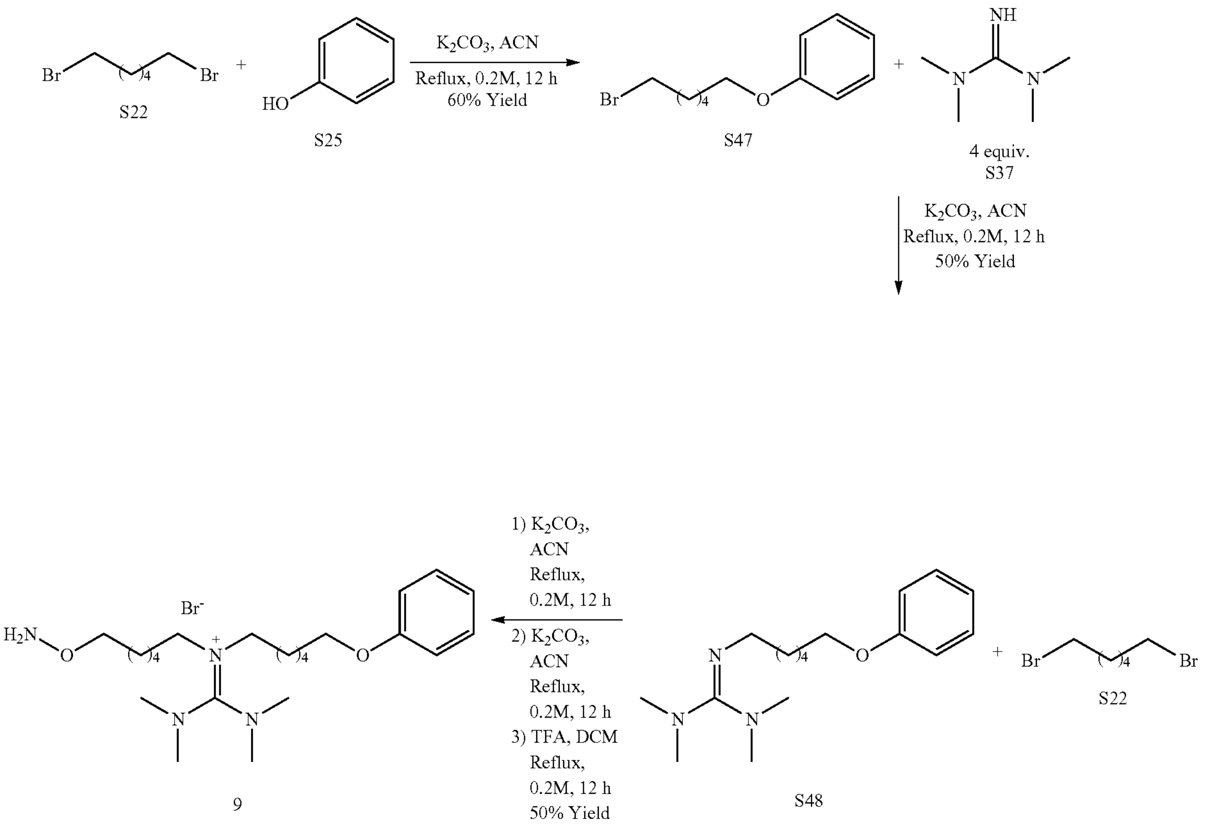

Synthesis of 1-(6-bromohexyloxy) benzene S47[9]

In a 25 ml round bottom flask charged with Teflon-coated magnetic stir bar, phenol S21 (94 mg, 1 mmol) and potassium carbonate (276 mg, 1 mmol) were taken in acetonitrile (5 ml). Next, 1, 6-dibromohexane S22 (0.307 ml, 2 mmol) was added and the flask was sealed with condenser. The reaction mixture was refluxed for 16 h and cooled down to room temperature. The white solid was filtered through celite funnel filter. The filtrate was concentrated under reduced pressure delivering a yellow oil, which was purified by flash chromatography column (n-hexane, Rf=0.1) to obtain 1-((6-bromohexyl)oxy)benzene S47 (171 mg 60% yield) as a pale-yellow oil. $^{1}$H NMR (500 MHz, $CDCl_3$) δ 7.29 (m, 2H), 6.98-6.80 (m, 3H), 3.95 (m, 2H), 3.42 (m, 2H), 1.90 (m, 2H), 1.79 (m, 2H), 1.56-1.48 (m, 4H) ppm. $^{13}$C NMR (126 MHz, $CDCl_3$) δ 159.0, 129.4, 120.6, 114.5, 67.6, 33.8, 32.7, 29.1, 27.9, 25.3 ppm. LRMS (ESI) $[MH]^+$ calcd. for $C_{12}H_{17}BrO$ 257.1, found 257.1.

was extracted with water (3×50 ml) to remove N, N-tetramethyl guanidine S37. The organic layer was dried over $Na_2SO_4$ and the solvent was concentrated under reduced pressure. The residue was mixed with ether (15 ml) and stirred for 1 h. The ether fraction was collected and the process was repeated. The combined ether fractions were concentrated under reduced pressure to afford the pure ethyl 1,1,3,3-tetramethyl-2-(6-phenoxyhexyl)guanidine S48 (117 mg, 40% yield) as slightly yellow colour liquid. $^{1}$H NMR (500 MHz, $CDCl_3$) δ 7.29 (m, 2H), 6.95 (t, J=7.3 Hz, 1H), 6.90 (d, J=7.9 Hz, 2H), 3.97 (t, J=6.3 Hz, 2H), 3.23 (m, 2H), 3.12 (s, 6H), 2.94 (s, 6H), 1.87-1.77 (m, 4H), 1.58-1.48 (m, 2H), 1.42 (m, 2H). $^{13}$C NMR (126 MHz, $CDCl_3$) δ 161.5, 159.0, 129.4, 120.6, 114.5, 67.5, 45.3, 40.6, 39.9, 29.7, 29.1, 26.6, 25.6 ppm. HRMS (ESI) $[M]^+$ calcd. for $C_{17}H_{29}N_3O$ 292.2383, found 292.2356.

Synthesis of 6-(aminooxy)-N-(bis(dimethylamino) methylene)-N-(6-phenoxyhexyl)hexan-1-aminium bromide 9

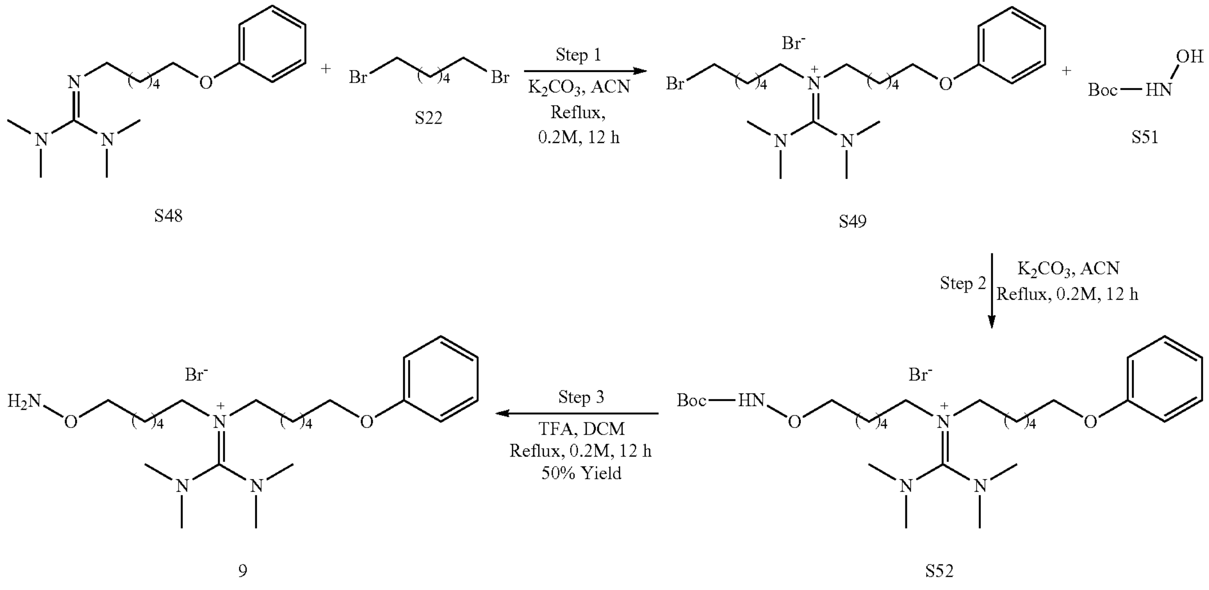

Step 1: In a 10 ml round bottom flask charged with Teflon-coated magnetic stir bead, potassium carbonate (680 mg, 4.92 mmol) and 1,1,3,3-tetramethyl-2-(6-phenoxy-hexyl)guanidine S48 (291 mg, 1 mmol) were mixed in acetonitrile (5 ml). Next, 1,6-dibromohexane S22 (0.307 ml, 2 mmol) was added and the flask was sealed by condenser. The reaction mixture was refluxed for 16 h and concentrated under reduced pressure. The residue was re-dissolved in dichloromethane (10 ml) and the organic layer was extracted with water (3×50 ml) to remove potassium carbonate. The organic layer was dried over $Na_2SO_4$ and the solvent was concentrated under reduced pressure. To this, ether (15 ml) was added and stirred for 1 h. The semi-solid white precipitate (product) observed in the process is subjected to another round of treatment with ether (15 ml) for 1 h. The resultant white precipitate was dried under reduced pressure to get the crude N-(bis(dimethylamino)methylene)-6-bromo-N-(6-phenoxyhexyl)hexan-1-aminium bromide S49.

Step 2: The crude N-(bis(dimethylamino)methylene)-6-bromo-N-(6-phenoxyhexyl)hexan-1-aminium bromide S49 was taken in another 10 ml round bottom flask in acetonitrile (5 ml). Next, tert-butyl hydroxycarbamate S50 (266 mg, 2 mmol) and potassium carbonate (230 mg, 2 mmol) were added and the flask was sealed with condenser. The reaction mixture was refluxed for 16 h and concentrated under reduced pressure. The residue was re-dissolved in dichloromethane (10 ml) and the organic layer was extracted with water (3×50 ml) to remove potassium carbonate. The organic layer was dried over $Na_2SO_4$ and the solvent was removed under reduced pressure. The residue was mixed with ether (15 ml) and stirred for 1 h. The white precipitate was isolated and treated with ether (15 ml) again for 1 h. Further, the white precipitate was dried under reduced pressure to render crude N-(bis(dimethylamino)methylene)-6-(((tert-butoxycarbonyl)amino)oxy)-N-(6-phenoxyhexyl) hexan-1-aminium bromide S51.

Step 3: The crude N-(bis(dimethylamino)methylene)-6-(((tert-butoxycarbonyl)amino)oxy)-N-(6-phenoxyhexyl) hexan-1-aminium bromide S51 was taken in a 5 ml round bottom flask charged with feflon-coated magnetic stir bar in dichloromethane (1 ml). Next, trifluoroacetic acid (0.076 ml, 1 mmol) was added and the reaction mixture was refluxed for 12 h. The reaction mixture was concentrated under reduced pressure. The residue was re-suspended in ether (15 ml) and stirred for 1 h. The white precipitate is isolated and treated again with ether (15 ml, 1 h). The white precipitate was dried under reduced pressure to afford the 6-(aminooxy)-N-(bis(dimethylamino)methylene)-N-(6-phenoxy-hexyl)hexan-1-aminium bromide 9 (218 mg, 45% yield) as a yellow colored liquid. $^{1}$H NMR (500 MHz, $D_2O$) δ 7.41 (m, 2H), 7.05 (m, 3H), 4.10 (m, 2H), 4.02 (m, 2H), 3.4-3.15 (m, 4H), 2.90 (s, 12H), 1.78 (m, 2H), 1.65 (m, 2H), 1.46 (m, 4H), 1.40-1.25 (m, 8H) ppm. $^{13}$C NMR (126 MHz, $D_2O$) δ 163.1, 158.0, 129.9, 121.5, 114.9, 75.6, 68.3, 49.1, 48.9, 39.4, 39.2, 28.0, 26.9, 26.7, 26.6, 25.7, 25.4, 24.6, 24.5. HRMS (ESI) $[M]^+$ calcd. for $C_{23}H_{43}N_4O_2$ 407.3381, found 407.3411.

REFERENCES

E. M. Pelegri-O'Day, E. W. Lin and H. D. Maynard, *J. Am. Chem. Soc.,* 2014, 136, 14323.

V. Chudasama, A. Maruani and S. Caddick, *Nat. Chem.,* 2016, 8, 114.

A. J. Keefe and S. Jiang, *Nat. Chem.,* 2012, 4, 59.

P. Agarwal and C. R. S Bertozzi, *Bioconjugate Chem.,* 2015, 26, 176;

X. Ning, R. P. Temming, J. Dommerholt, J. Guo, D. B. Ania, M. F. Debets, M. A. Wolfert, G.-J. Boons and F. L van Delft, *Angew. Chem., Int. Ed.,* 2010, 49, 3065.

S. R. Adusumalli, D. G. Rawale, U. Singh, P. Tripathi, R. Paul, N. Kalra, R. K. Mishra, S. Shukla and V. Rai, *J. Am. Chem. Soc.,* 2018, 140, 15114;

J. M. Antos and M. B. Francis, *J. Δm. Chem. Soc.,* 2004, 126, 10256;
D. Chen, M. M. Disotuar, X. Xiong, Y. Wang and D. H.-C. Chou, *Chem. Sci.,* 2017, 8, 2717;
C. D. Spicer and B. G. S. Davis, *Nat. Commun.,* 2014, 5, 4740;
G. Chen, A. Heim, D. Riether, D. Yee, Y. Milgrom, M. A. Gawinowicz and D. Sames, *J. Am. Chem. Soc.,* 2003, 125, 8130;
Y. Takaoka, H. Tsutsumi, N. Kasagi, E. Nakata and I. Hamachi, *J. Δm. Chem. Soc.,* 2006, 128, 3273;
M. J. Matos, B. L. Oliveira, N. Martínez-Sáez, A. Guerreiro, P. M. S. D. Cal, J. Bertoldo, M. Maneiro, E. Perkins, J. Howard, M. J. Deery, J. M. Chalker, F. Corzana, G. Jiménez-Osés and
G. J. L. Bernardes, *J. Δm. Chem. Soc.,* 2018, 140, 4004;
R. Aebersold and M. Mann, *Nature,* 2003, 422, 198-207;
A. J. Barrett, N. D. Rawlings and J. F. Woessner, Handbook of Proteolytic Enzymes; Academic Press: San Diego, CA, 1998.
Q. Hu, R. J. Noll, H. Li, A. Makarov, M. Hardman and R. G. Cooks, *J. Mass Spectrom.,* 2005, 40, 430;
H. López-Fernández, H. M. Santos, J. L. Capelo, F. Fdez-Riverola, D. Glez-Peña and M. Reboiro-Jato, *BMC Bioinformatics,* 2015, 16, 318;
P. Stefanowicz, A. Kluczyk and Z. Szewczuk, *Amino Acids. Pept. Proteins,* 2016, 40, 36.
[1] M. R. Wilkins, I. Lindskog, E. Gasteiger, A. Bairoch, J. C. Sanchez, D. F. Hochstrasser and R. D. Appel, *Electrophoresis,* 1997, 18, 403.
[2] A. R. Ramya, M. L. P. Reddy, A. H. Cowley and K. V. Vasudevan, *Inorg. Chem.,* 2010, 49, 2407.
[3] A. V. Pestov, A. E. Permyakov, P. A. Slepukhin, L. K. Neudachina and Yu. G. Yatluk, *Rus. J. Cor. Chem.,* 2010, 36, 769.
[4] Y. Liu, R. Xiang, X. Du, Y. Ding and B. Ma, *Chem. Commun.,* 2014, 50, 12779.
[5] C. K. Sams, F. Somoza, I. Bernal and H. Toftlund, *Inorg. Chim. Acta.,* 2001, 318, 45.
[6] S. Raiguel, J. Thomas, K. Binnemans and W. Dehaen, *Eur. J. Org. Chem.,* 2018, 35, 4850.
[7] M. Xu, C. Kuang, Z. Wang, Q. Yang and Y. Jiang, Synthesis, 2011, 223.
[8] L. Purushottam, S. R. Adusumalli, M. Chilamari and V. Rai, *Chem. Commun.,* 2017, 53, 959
[9] L. Huang, A. Shi, F. He and X. Li, *Bioorg. Med. Chem.,* 2010, 18, 1244.

The invention claimed is:

1. A chemoselective sensitivity booster for tagging a peptide or peptide conjugate for analysis of a peptide, protein, protein bioconjugate, and antibody, wherein the chemoselective sensitivity booster comprises:

sp2 or sp3 nitrogen centers in combination with hydrophobic carbon chains linked with an electrophile or a nucleophile, wherein the chemoselective sensitivity booster is selected from the group consisting of 2,5-dioxopyrrolidin-1-yl picolinate, 2,5-dioxopyrrolidin-1-yl 4-(dibenzylamino)benzoate, 2,5-dioxopyrrolidin-1-yl 3-(benzyl(pyridin-2-ylmethyl)amino)propanoate, 2,5-dioxopyrrolidin-1-yl 3-(bis(pyridin-2-ylmethyl)amino)propanoate, 2,5-dioxopyrrolidin-1-yl 4-(4-((dibenzylamino)methyl)-1H-1,2,3-triazol-1-yl)benzoate, 2,5-dioxopyrrolidin-1-yl-4-((6-(1H-imidazol-1-yl)hexyl)oxy)benzoate, 1-(6-(4-(((2,5-dioxopyrrolidin-1-yl)oxy)carbonyl)phenoxy)hexyl)pyridin-1-ium bromide, 1-benzyl-3-(6-(4-(((2,5-dioxopyrrolidin-1-yl)oxy)carbonyl)phenoxy)hexyl)-1H-imidazol-3-ium bromide, 4-(dimethylamino)-1-(6-(4-(((2,5-dioxopyrrolidin-1-yl)oxy)carbonyl)phenoxy) hexyl)pyridin-1-ium bromide, N-(bis(dimethylamino)methylene)-N-butyl-6-(4-(((2,5-dioxopyrrolidin-1-yl)oxy)carbonyl)phenoxy)hexan-1-aminium bromide, and 6-(aminooxy)-N-(bis(dimethylamino)methylene)-N-(6-phenoxyhexyl)hexan-1-aminium bromide.

2. The chemoselective sensitivity booster as claimed in claim 1, wherein a sensitivity of tagged peptide detection is up to attomolar concentration as measured by mass spectrometry.

3. The chemoselective sensitivity booster as claimed in claim 1, wherein the conjugation of the booster is at either to a polar or a non-polar peptide.

4. The chemoselective sensitivity booster as claimed in claim 1, wherein a signal enhancement of the tagged peptides has a mass shift of $\Delta m=374$ Da with the conjugation of sensitivity booster in mass spectrometry.

5. The chemoselective sensitivity booster as claimed in claim 1, wherein the conjugation of the chemoselective sensitivity booster is at ε-amine of C-terminus Lys in a peptide or with an N-terminus α-amine.

6. The chemoselective sensitivity booster as claimed in claim 1, wherein a sequence coverage of the tagged peptides in peptide mapping is 75-100%.

7. The chemoselective sensitivity booster as claimed in claim 1, wherein a sensitivity and ease of detection of fragments in a tandem mass spectrometry (MS-MS) of peptide is improved.

8. The chemoselective sensitivity booster as claimed in claim 1, wherein the conjugation of sensitivity booster is for peptide detection in proteins, protein bioconjugates, antibodies including monoclonal antibody (mAb), and antibody conjugates.

* * * * *

SEQUENCE LISTING

```
<160> NUMBER OF SEQ ID NOS: 77

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 1

Val Gly Val Ala Pro Gly
1               5


<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Ala Glu Asp Asp Val Glu Asp Tyr
1               5


<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Gly Phe His Lys
1


<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
```

<400> SEQUENCE: 4

Gly Gly Pro Arg Lys
1               5

<210> SEQ ID NO 5
<211> LENGTH: 105
<212> TYPE: PRT
<213> ORGANISM: Equus caballus
<220> FEATURE:
<221> NAME/KEY: misc_feature
<222> LOCATION: (1)..(1)
<223> OTHER INFORMATION: Xaa is any amino acid

<400> SEQUENCE: 5

Xaa Gly Asp Val Glu Lys Gly Lys Lys Ile Phe Val Gln Lys Cys Ala
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Phe Thr
        35                  40                  45

Tyr Thr Asp Ala Asn Lys Asn Lys Gly Ile Thr Trp Lys Glu Glu Thr
    50                  55                  60

Leu Met Glu Tyr Leu Glu Asn Pro Lys Lys Tyr Ile Pro Gly Thr Lys
65                  70                  75                  80

Met Ile Phe Ala Gly Ile Lys Lys Lys Thr Glu Arg Glu Asp Leu Ile
                85                  90                  95

Ala Tyr Leu Lys Lys Ala Thr Asn Glu
            100                 105

<210> SEQ ID NO 6
<211> LENGTH: 449
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 7
<211> LENGTH: 214
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

-continued

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 8
<211> LENGTH: 19
<212> TYPE: PRT
<213> ORGANISM: Homo sapiens

<400> SEQUENCE: 8

Glu Val Gln Leu Val Glu Ser Gly Gly Gly Leu Val Gln Pro Gly Gly
1               5                   10                  15

Ser Leu Arg


<210> SEQ ID NO 9
<211> LENGTH: 11
<212> TYPE: PRT
<213> ORGANISM: Homo sapiens

<400> SEQUENCE: 9

Leu Ser Cys Ala Ala Ser Gly Phe Asn Ile Lys
1               5                   10


<210> SEQ ID NO 10
<211> LENGTH: 8
<212> TYPE: PRT
<213> ORGANISM: Homo sapiens

<400> SEQUENCE: 10

Asp Thr Tyr Ile His Trp Val Arg
1               5


<210> SEQ ID NO 11
<211> LENGTH: 5
<212> TYPE: PRT
<213> ORGANISM: Homo sapiens

<400> SEQUENCE: 11

Gln Ala Pro Gly Lys
1               5


<210> SEQ ID NO 12
<211> LENGTH: 7
<212> TYPE: PRT
<213> ORGANISM: Homo sapiens

<400> SEQUENCE: 12
```

```
Gly Leu Glu Trp Val Ala Arg
1               5


<210> SEQ ID NO 13
<211> LENGTH: 9
<212> TYPE: PRT
<213> ORGANISM: Homo sapiens

<400> SEQUENCE: 13

Ile Tyr Pro Thr Asn Gly Tyr Thr Arg
1               5


<210> SEQ ID NO 14
<211> LENGTH: 6
<212> TYPE: PRT
<213> ORGANISM: Homo sapiens

<400> SEQUENCE: 14

Tyr Ala Asp Ser Val Lys
1               5


<210> SEQ ID NO 15
<211> LENGTH: 9
<212> TYPE: PRT
<213> ORGANISM: Homo sapiens

<400> SEQUENCE: 15

Phe Thr Ile Ser Ala Asp Thr Ser Lys
1               5


<210> SEQ ID NO 16
<211> LENGTH: 11
<212> TYPE: PRT
<213> ORGANISM: Homo sapiens

<400> SEQUENCE: 16

Asn Thr Ala Tyr Leu Gln Met Asn Ser Leu Arg
1               5                   10


<210> SEQ ID NO 17
<211> LENGTH: 11
<212> TYPE: PRT
<213> ORGANISM: Homo sapiens

<400> SEQUENCE: 17

Ala Glu Asp Thr Ala Val Tyr Tyr Cys Ser Arg
1               5                   10


<210> SEQ ID NO 18
<211> LENGTH: 26
<212> TYPE: PRT
<213> ORGANISM: Homo sapiens

<400> SEQUENCE: 18

Trp Gly Gly Asp Gly Phe Tyr Ala Met Asp Tyr Trp Gly Gln Gly Thr
1               5                   10                  15

Leu Val Thr Val Ser Ser Ala Ser Thr Lys
            20                  25


<210> SEQ ID NO 19
<211> LENGTH: 12
<212> TYPE: PRT
<213> ORGANISM: Homo sapiens

<400> SEQUENCE: 19
```

-continued

```
Gly Pro Ser Val Phe Pro Leu Ala Pro Ser Ser Lys
1               5                   10


<210> SEQ ID NO 20
<211> LENGTH: 14
<212> TYPE: PRT
<213> ORGANISM: Homo sapiens

<400> SEQUENCE: 20

Ser Thr Ser Gly Gly Thr Ala Ala Leu Gly Cys Leu Val Lys
1               5                   10


<210> SEQ ID NO 21
<211> LENGTH: 63
<212> TYPE: PRT
<213> ORGANISM: Homo sapiens

<400> SEQUENCE: 21

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
            20                  25                  30

Tyr Ser Leu Ser Ser Val Val Thr Val Pro Ser Ser Ser Leu Gly Thr
        35                  40                  45

Gln Thr Tyr Ile Cys Asn Val Asn His Lys Pro Ser Asn Thr Lys
    50                  55                  60


<210> SEQ ID NO 22
<211> LENGTH: 4
<212> TYPE: PRT
<213> ORGANISM: Homo sapiens

<400> SEQUENCE: 22

Val Glu Pro Lys
1


<210> SEQ ID NO 23
<211> LENGTH: 4
<212> TYPE: PRT
<213> ORGANISM: Homo sapiens

<400> SEQUENCE: 23

Ser Cys Asp Lys
1


<210> SEQ ID NO 24
<211> LENGTH: 26
<212> TYPE: PRT
<213> ORGANISM: Homo sapiens

<400> SEQUENCE: 24

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25


<210> SEQ ID NO 25
<211> LENGTH: 7
<212> TYPE: PRT
<213> ORGANISM: Homo sapiens

<400> SEQUENCE: 25
```

-continued

Asp Thr Leu Met Ile Ser Arg
1 5

<210> SEQ ID NO 26
<211> LENGTH: 19
<212> TYPE: PRT
<213> ORGANISM: Homo sapiens

<400> SEQUENCE: 26

Thr Pro Glu Val Thr Cys Val Val Val Asp Val Ser His Glu Asp Pro
1 5 10 15

Glu Val Lys

<210> SEQ ID NO 27
<211> LENGTH: 14
<212> TYPE: PRT
<213> ORGANISM: Homo sapiens

<400> SEQUENCE: 27

Phe Asn Trp Tyr Val Asp Gly Val Glu Val His Asn Ala Lys
1 5 10

<210> SEQ ID NO 28
<211> LENGTH: 4
<212> TYPE: PRT
<213> ORGANISM: Homo sapiens

<400> SEQUENCE: 28

Thr Lys Pro Arg
1

<210> SEQ ID NO 29
<211> LENGTH: 9
<212> TYPE: PRT
<213> ORGANISM: Homo sapiens

<400> SEQUENCE: 29

Glu Glu Gln Tyr Asn Ser Thr Tyr Arg
1 5

<210> SEQ ID NO 30
<211> LENGTH: 16
<212> TYPE: PRT
<213> ORGANISM: Homo sapiens

<400> SEQUENCE: 30

Val Val Ser Val Leu Thr Val Leu His Gln Asp Trp Leu Asn Gly Lys
1 5 10 15

<210> SEQ ID NO 31
<211> LENGTH: 4
<212> TYPE: PRT
<213> ORGANISM: Homo sapiens

<400> SEQUENCE: 31

Val Ser Asn Lys
1

<210> SEQ ID NO 32
<211> LENGTH: 8
<212> TYPE: PRT
<213> ORGANISM: Homo sapiens

<400> SEQUENCE: 32

-continued

Ala Leu Pro Ala Pro Ile Glu Lys
1               5

<210> SEQ ID NO 33
<211> LENGTH: 4
<212> TYPE: PRT
<213> ORGANISM: Homo sapiens

<400> SEQUENCE: 33

Thr Ile Ser Lys
1

<210> SEQ ID NO 34
<211> LENGTH: 4
<212> TYPE: PRT
<213> ORGANISM: Homo sapiens

<400> SEQUENCE: 34

Gly Gln Pro Arg
1

<210> SEQ ID NO 35
<211> LENGTH: 11
<212> TYPE: PRT
<213> ORGANISM: Homo sapiens

<400> SEQUENCE: 35

Glu Pro Gln Val Tyr Thr Leu Pro Pro Ser Arg
1               5                   10

<210> SEQ ID NO 36
<211> LENGTH: 5
<212> TYPE: PRT
<213> ORGANISM: Homo sapiens

<400> SEQUENCE: 36

Glu Glu Met Thr Lys
1               5

<210> SEQ ID NO 37
<211> LENGTH: 10
<212> TYPE: PRT
<213> ORGANISM: Homo sapiens

<400> SEQUENCE: 37

Asn Gln Val Ser Leu Thr Cys Leu Val Lys
1               5                   10

<210> SEQ ID NO 38
<211> LENGTH: 22
<212> TYPE: PRT
<213> ORGANISM: Homo sapiens

<400> SEQUENCE: 38

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 39
<211> LENGTH: 17
<212> TYPE: PRT
<213> ORGANISM: Homo sapiens

<400> SEQUENCE: 39

-continued

```
Thr Thr Pro Pro Val Leu Asp Ser Asp Gly Ser Phe Phe Leu Tyr Ser
1               5                   10                  15

Lys


<210> SEQ ID NO 40
<211> LENGTH: 5
<212> TYPE: PRT
<213> ORGANISM: Homo sapiens

<400> SEQUENCE: 40

Leu Thr Val Asp Lys
1               5


<210> SEQ ID NO 41
<211> LENGTH: 23
<212> TYPE: PRT
<213> ORGANISM: Homo sapiens

<400> SEQUENCE: 41

Trp Gln Gln Gly Asn Val Phe Ser Cys Ser Val Met His Glu Ala Leu
1               5                   10                  15

His Asn His Tyr Thr Gln Lys
            20


<210> SEQ ID NO 42
<211> LENGTH: 7
<212> TYPE: PRT
<213> ORGANISM: Homo sapiens

<400> SEQUENCE: 42

Ser Leu Ser Leu Ser Pro Gly
1               5


<210> SEQ ID NO 43
<211> LENGTH: 18
<212> TYPE: PRT
<213> ORGANISM: Homo sapiens

<400> SEQUENCE: 43

Asp Ile Gln Met Thr Gln Ser Pro Ser Ser Leu Ser Ala Ser Val Gly
1               5                   10                  15

Asp Arg


<210> SEQ ID NO 44
<211> LENGTH: 6
<212> TYPE: PRT
<213> ORGANISM: Homo sapiens

<400> SEQUENCE: 44

Val Thr Ile Thr Cys Arg
1               5


<210> SEQ ID NO 45
<211> LENGTH: 18
<212> TYPE: PRT
<213> ORGANISM: Homo sapiens

<400> SEQUENCE: 45

Ala Ser Gln Asp Val Asn Thr Ala Val Ala Trp Tyr Gln Gln Lys Pro
1               5                   10                  15

Gly Lys
```

-continued

<210> SEQ ID NO 46
<211> LENGTH: 15
<212> TYPE: PRT
<213> ORGANISM: Homo sapiens

<400> SEQUENCE: 46

Leu Leu Ile Tyr Ser Ala Ser Phe Leu Tyr Ser Gly Val Ser Arg
1 5 10 15

<210> SEQ ID NO 47
<211> LENGTH: 5
<212> TYPE: PRT
<213> ORGANISM: Homo sapiens

<400> SEQUENCE: 47

Phe Ser Gly Ser Arg
1 5

<210> SEQ ID NO 48
<211> LENGTH: 37
<212> TYPE: PRT
<213> ORGANISM: Homo sapiens

<400> SEQUENCE: 48

Ser Gly Thr Asp Phe Thr Leu Thr Ile Ser Ser Leu Gln Pro Glu Asp
1 5 10 15

Phe Ala Thr Tyr Tyr Cys Gln Gln His Tyr Thr Thr Pro Pro Thr Phe
20 25 30

Gly Gln Gly Thr Lys
35

<210> SEQ ID NO 49
<211> LENGTH: 4
<212> TYPE: PRT
<213> ORGANISM: Homo sapiens

<400> SEQUENCE: 49

Val Glu Ile Lys
1

<210> SEQ ID NO 50
<211> LENGTH: 17
<212> TYPE: PRT
<213> ORGANISM: Homo sapiens

<400> SEQUENCE: 50

Thr Val Ala Ala Pro Ser Val Phe Ile Phe Pro Pro Ser Asp Glu Leu
1 5 10 15

Lys

<210> SEQ ID NO 51
<211> LENGTH: 16
<212> TYPE: PRT
<213> ORGANISM: Homo sapiens

<400> SEQUENCE: 51

Ser Gly Thr Ala Ser Val Val Cys Leu Leu Asn Asn Phe Tyr Pro Arg
1 5 10 15

<210> SEQ ID NO 52
<211> LENGTH: 4
<212> TYPE: PRT
<213> ORGANISM: Homo sapiens

<400> SEQUENCE: 52

Val Gln Trp Lys
1

<210> SEQ ID NO 53
<211> LENGTH: 20
<212> TYPE: PRT
<213> ORGANISM: Homo sapiens

<400> SEQUENCE: 53

Val Asp Asn Ala Leu Gln Ser Gly Asn Ser Gln Glu Ser Val Thr Glu
1 5 10 15

Gln Asp Ser Lys
20

<210> SEQ ID NO 54
<211> LENGTH: 14
<212> TYPE: PRT
<213> ORGANISM: Homo sapiens

<400> SEQUENCE: 54

Asp Ser Thr Tyr Ser Leu Ser Ser Thr Leu Thr Leu Ser Lys
1 5 10

<210> SEQ ID NO 55
<211> LENGTH: 5
<212> TYPE: PRT
<213> ORGANISM: Homo sapiens

<400> SEQUENCE: 55

Ala Asp Tyr Glu Lys
1 5

<210> SEQ ID NO 56
<211> LENGTH: 17
<212> TYPE: PRT
<213> ORGANISM: Homo sapiens

<400> SEQUENCE: 56

Val Tyr Ala Cys Glu Val Thr His Gln Gly Leu Ser Ser Pro Val Thr
1 5 10 15

Lys

<210> SEQ ID NO 57
<211> LENGTH: 4
<212> TYPE: PRT
<213> ORGANISM: Homo sapiens

<400> SEQUENCE: 57

Ser Phe Asn Arg
1

<210> SEQ ID NO 58
<211> LENGTH: 6
<212> TYPE: PRT
<213> ORGANISM: Equus caballus
<220> FEATURE:
<221> NAME/KEY: misc_feature
<222> LOCATION: (1)..(1)
<223> OTHER INFORMATION: Xaa is any amino acid

<400> SEQUENCE: 58

Xaa Gly Asp Val Glu Lys 1 5

<210> SEQ ID NO 59
<211> LENGTH: 5
<212> TYPE: PRT
<213> ORGANISM: Equus caballus

<400> SEQUENCE: 59

Ile Phe Val Gln Lys
1 5

<210> SEQ ID NO 60
<211> LENGTH: 9
<212> TYPE: PRT
<213> ORGANISM: Equus caballus

<400> SEQUENCE: 60

Cys Ala Gln Cys His Thr Val Glu Lys
1 5

<210> SEQ ID NO 61
<211> LENGTH: 11
<212> TYPE: PRT
<213> ORGANISM: Equus caballus

<400> SEQUENCE: 61

Thr Gly Pro Asn Leu His Gly Leu Phe Gly Arg
1 5 10

<210> SEQ ID NO 62
<211> LENGTH: 14
<212> TYPE: PRT
<213> ORGANISM: Equus caballus

<400> SEQUENCE: 62

Thr Gly Gln Ala Pro Gly Phe Thr Tyr Thr Asp Ala Asn Lys
1 5 10

<210> SEQ ID NO 63
<211> LENGTH: 5
<212> TYPE: PRT
<213> ORGANISM: Equus caballus

<400> SEQUENCE: 63

Gly Ile Thr Trp Lys
1 5

<210> SEQ ID NO 64
<211> LENGTH: 12
<212> TYPE: PRT
<213> ORGANISM: Equus caballus

<400> SEQUENCE: 64

Glu Glu Thr Leu Met Glu Tyr Leu Glu Asn Pro Lys
1 5 10

<210> SEQ ID NO 65
<211> LENGTH: 6
<212> TYPE: PRT
<213> ORGANISM: Equus caballus

<400> SEQUENCE: 65

Tyr Ile Pro Gly Thr Lys
1 5

-continued

```
<210> SEQ ID NO 66
<211> LENGTH: 7
<212> TYPE: PRT
<213> ORGANISM: Equus caballus

<400> SEQUENCE: 66

Met Ile Phe Ala Gly Ile Lys
1               5


<210> SEQ ID NO 67
<211> LENGTH: 8
<212> TYPE: PRT
<213> ORGANISM: Equus caballus

<400> SEQUENCE: 67

Glu Asp Leu Ile Ala Tyr Leu Lys
1               5


<210> SEQ ID NO 68
<211> LENGTH: 4
<212> TYPE: PRT
<213> ORGANISM: Equus caballus

<400> SEQUENCE: 68

Ala Thr Asn Glu
1


<210> SEQ ID NO 69
<211> LENGTH: 11
<212> TYPE: PRT
<213> ORGANISM: Equus caballus
<220> FEATURE:
<221> NAME/KEY: misc_feature
<222> LOCATION: (1)..(1)
<223> OTHER INFORMATION: Xaa is any amino acid

<400> SEQUENCE: 69

Xaa Gly Asp Val Glu Lys Gly Lys Lys Ile Phe
1               5                   10


<210> SEQ ID NO 70
<211> LENGTH: 26
<212> TYPE: PRT
<213> ORGANISM: Equus caballus

<400> SEQUENCE: 70

Val Gln Lys Cys Ala Gln Cys His Thr Val Glu Lys Gly Gly Lys His
1               5                   10                  15

Lys Thr Gly Pro Asn Leu His Gly Leu Phe
            20                  25


<210> SEQ ID NO 71
<211> LENGTH: 10
<212> TYPE: PRT
<213> ORGANISM: Equus caballus

<400> SEQUENCE: 71

Gly Arg Lys Thr Gly Gln Ala Pro Gly Phe
1               5                   10


<210> SEQ ID NO 72
<211> LENGTH: 11
<212> TYPE: PRT
<213> ORGANISM: Equus caballus
```

-continued

```
<400> SEQUENCE: 72

Thr Asp Ala Asn Lys Asn Lys Gly Ile Thr Trp
1               5                   10


<210> SEQ ID NO 73
<211> LENGTH: 8
<212> TYPE: PRT
<213> ORGANISM: Equus caballus

<400> SEQUENCE: 73

Lys Glu Glu Thr Leu Met Glu Tyr
1               5


<210> SEQ ID NO 74
<211> LENGTH: 7
<212> TYPE: PRT
<213> ORGANISM: Equus caballus

<400> SEQUENCE: 74

Leu Glu Asn Pro Lys Lys Tyr
1               5


<210> SEQ ID NO 75
<211> LENGTH: 8
<212> TYPE: PRT
<213> ORGANISM: Equus caballus

<400> SEQUENCE: 75

Ile Pro Gly Thr Lys Met Ile Phe
1               5


<210> SEQ ID NO 76
<211> LENGTH: 15
<212> TYPE: PRT
<213> ORGANISM: Equus caballus

<400> SEQUENCE: 76

Ala Gly Ile Lys Lys Lys Thr Glu Arg Glu Asp Leu Ile Ala Tyr
1               5                   10                  15


<210> SEQ ID NO 77
<211> LENGTH: 7
<212> TYPE: PRT
<213> ORGANISM: Equus caballus

<400> SEQUENCE: 77

Leu Lys Lys Ala Thr Asn Glu
1               5
```